(12) United States Patent  
Rashidi

(10) Patent No.: US 7,881,809 B2  
(45) Date of Patent: Feb. 1, 2011

(54) ELECTROPHYSIOLOGY/ABLATION CATHETER AND REMOTE ACTUATOR THEREFOR

(75) Inventor: Rassoll Rashidi, Cleveland, OH (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 1092 days.

(21) Appl. No.: 11/633,593

(22) Filed: Dec. 5, 2006

(65) Prior Publication Data

US 2007/0078455 A1    Apr. 5, 2007

Related U.S. Application Data

(60) Continuation of application No. 10/260,242, filed on Sep. 30, 2002, which is a division of application No. 09/232,866, filed on Jan. 15, 1999, now abandoned, which is a continuation-in-part of application No. 08/880,080, filed on Jun. 20, 1997, now Pat. No. 5,861,024.

(51) Int. Cl.  
*A61N 1/05* (2006.01)

(52) U.S. Cl. .............. 607/122; 607/99; 607/119; 606/129; 600/374; 600/585

(58) Field of Classification Search .................. None  
See application file for complete search history.

(56) References Cited

U.S. PATENT DOCUMENTS

| | | | |
|---|---|---|---|
| 3,190,286 A | 6/1965 | Stokes | |
| 3,416,531 A | 12/1968 | Edwards | |
| 3,521,620 A | 7/1970 | Cook | |
| 3,605,725 A | 9/1971 | Bentov | |
| 3,906,938 A | 9/1975 | Fleischhacker | |
| 4,456,017 A * | 6/1984 | Miles | 600/585 |
| 4,920,980 A | 5/1990 | Jackowski | |
| 4,960,134 A | 10/1990 | Webster, Jr. | |
| 5,108,368 A | 4/1992 | Hammerslag et al. | |
| 5,125,896 A | 6/1992 | Hojeibane | |
| 5,156,151 A | 10/1992 | Imran | |
| 5,170,803 A | 12/1992 | Hewson et al. | |
| 5,203,772 A | 4/1993 | Hammerslag et al. | |
| 5,254,088 A | 10/1993 | Lundquist et al. | |
| 5,273,535 A | 12/1993 | Edwards et al. | |
| 5,279,299 A | 1/1994 | Imran | |
| 5,318,525 A | 6/1994 | West et al. | |
| 5,325,845 A | 7/1994 | Adair | |
| 5,342,299 A | 8/1994 | Snoke et al. | |

(Continued)

*Primary Examiner*—Kennedy J Schaetzle  
(74) *Attorney, Agent, or Firm*—Wiley Rein LLP

(57) ABSTRACT

A cardiac catheter for minimally invasive diagnostic and/or ablation procedures includes an elongated cylindrical, electrically non-conductive exterior tube with surface electrodes disposed on its distal portion and a handle on its proximal end. The distal portion can be curved into a curvature retained by a single action on a manual actuator. An electromechanical drive system may be incorporated into the handle. An electrical heating element may be incorporated within the distal electrode for ablation procedures. A removable, disposable blood contacting segment may be provided. The non-blood contacting actuator is thus reusable. The catheter includes two tension/compression members, which are wires with circular cross-sections that are integrally formed into ribbon-like configurations at their distal portions, for curvature formation. The handle includes a pivoted member movable in one direction by the thumb of the user's hand grasping the handle and in the opposite direction by the other fingers of the same hand.

29 Claims, 43 Drawing Sheets

U.S. PATENT DOCUMENTS

| | | |
|---|---|---|
| 5,383,852 A | 1/1995 | Stevens-Wright |
| 5,396,902 A * | 3/1995 | Brennen et al. .............. 600/585 |
| 5,397,304 A * | 3/1995 | Truckai ....................... 604/528 |
| 5,415,633 A | 5/1995 | Lazarus et al. |
| 5,454,370 A | 10/1995 | Avitall |
| 5,462,527 A | 10/1995 | Stevens-Wright et al. |
| 5,465,717 A | 11/1995 | Imran et al. |
| 5,478,330 A | 12/1995 | Imran et al. |
| 5,487,757 A | 1/1996 | Truckai et al. |
| 5,492,131 A | 2/1996 | Galel |
| 5,531,676 A | 7/1996 | Edwards et al. |
| 5,549,542 A | 8/1996 | Kovalcheck |
| 5,562,619 A | 10/1996 | Mirarchi et al. |
| 5,588,964 A | 12/1996 | Imran et al. |
| 5,611,777 A | 3/1997 | Bowden et al. |
| 5,656,030 A | 8/1997 | Hunjan et al. |
| 5,658,029 A | 8/1997 | Franko |
| 5,662,606 A | 9/1997 | Cimino et al. |
| 5,702,433 A | 12/1997 | Taylor et al. |
| 5,715,817 A | 2/1998 | Stevens-Wright et al. |
| 5,735,846 A | 4/1998 | Panescu et al. |
| 5,807,249 A | 9/1998 | Qin et al. |
| 5,853,409 A | 12/1998 | Swanson et al. |
| 5,861,024 A | 1/1999 | Rashidi |
| 5,877,529 A | 3/1999 | So et al. |
| 5,891,095 A | 4/1999 | Eggers et al. |
| 5,935,102 A | 8/1999 | Bowden et al. |
| 5,944,690 A | 8/1999 | Falwell et al. |
| 5,987,344 A | 11/1999 | West |
| 6,066,125 A | 5/2000 | Webster |
| 6,123,699 A | 9/2000 | Webster |
| 6,183,463 B1 | 2/2001 | Webster, Jr. |
| 6,221,070 B1 | 4/2001 | Tu et al. |
| 6,272,371 B1 | 8/2001 | Shlomo |
| 6,500,167 B1 | 12/2002 | Webster |

* cited by examiner

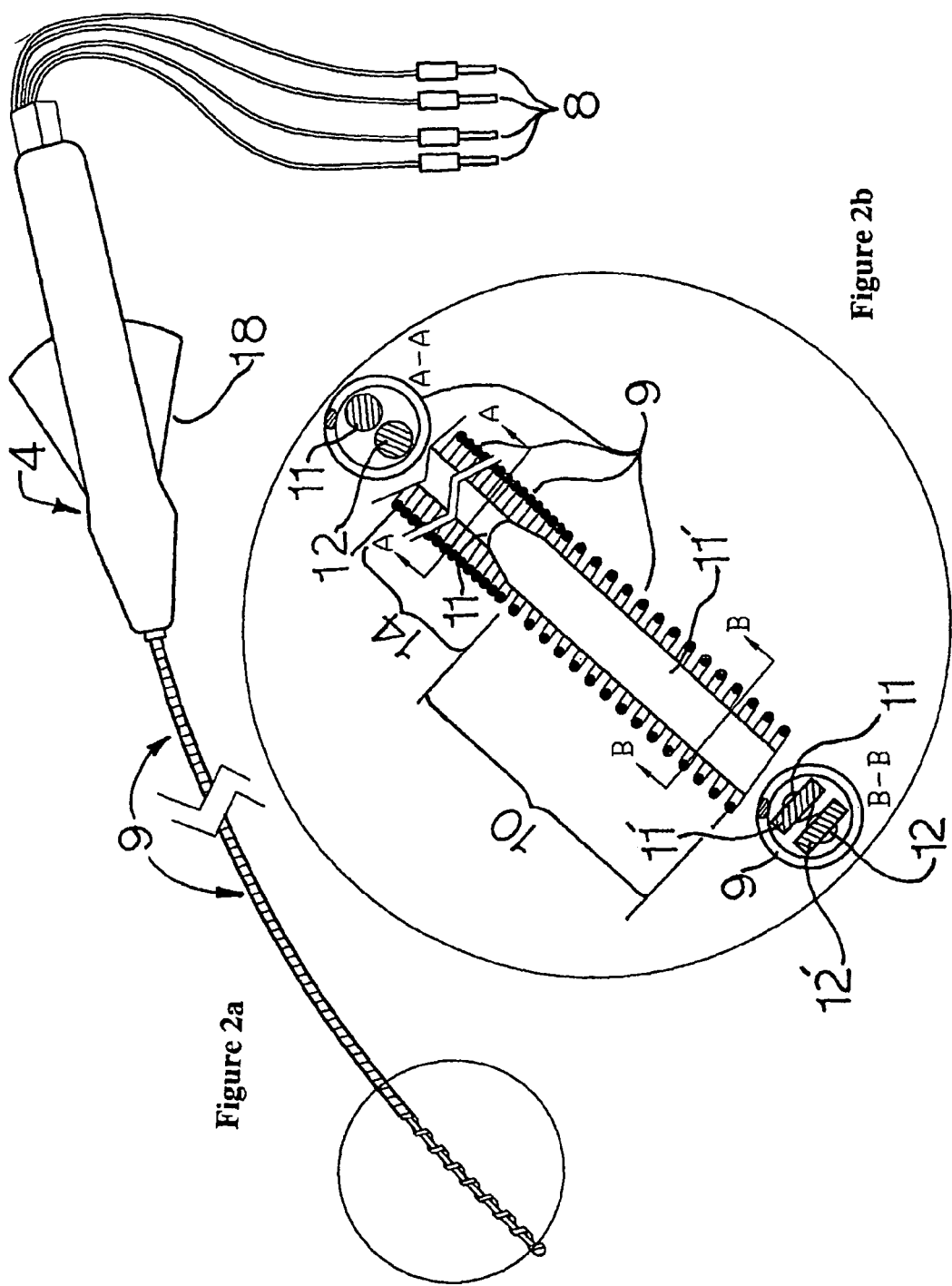

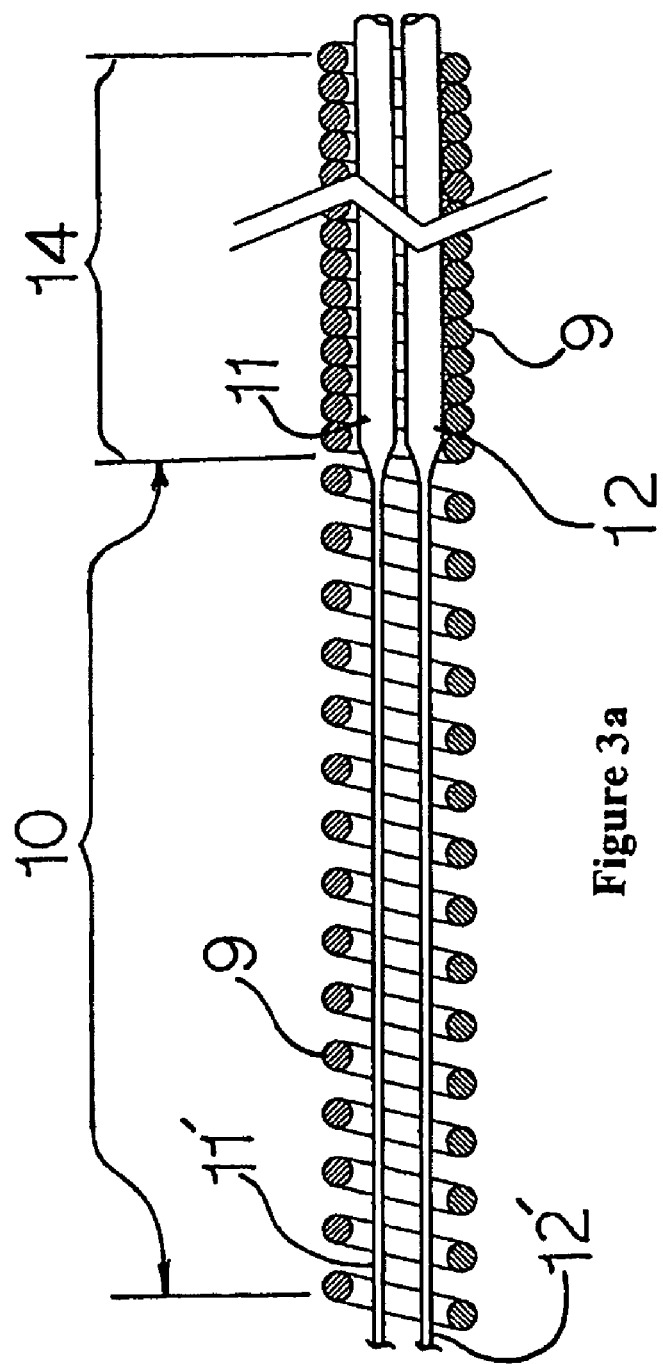
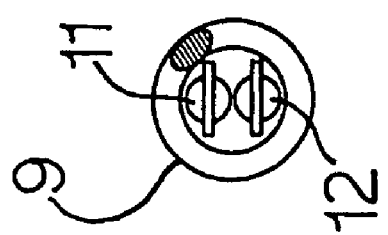
Figure 3a
Figure 3b

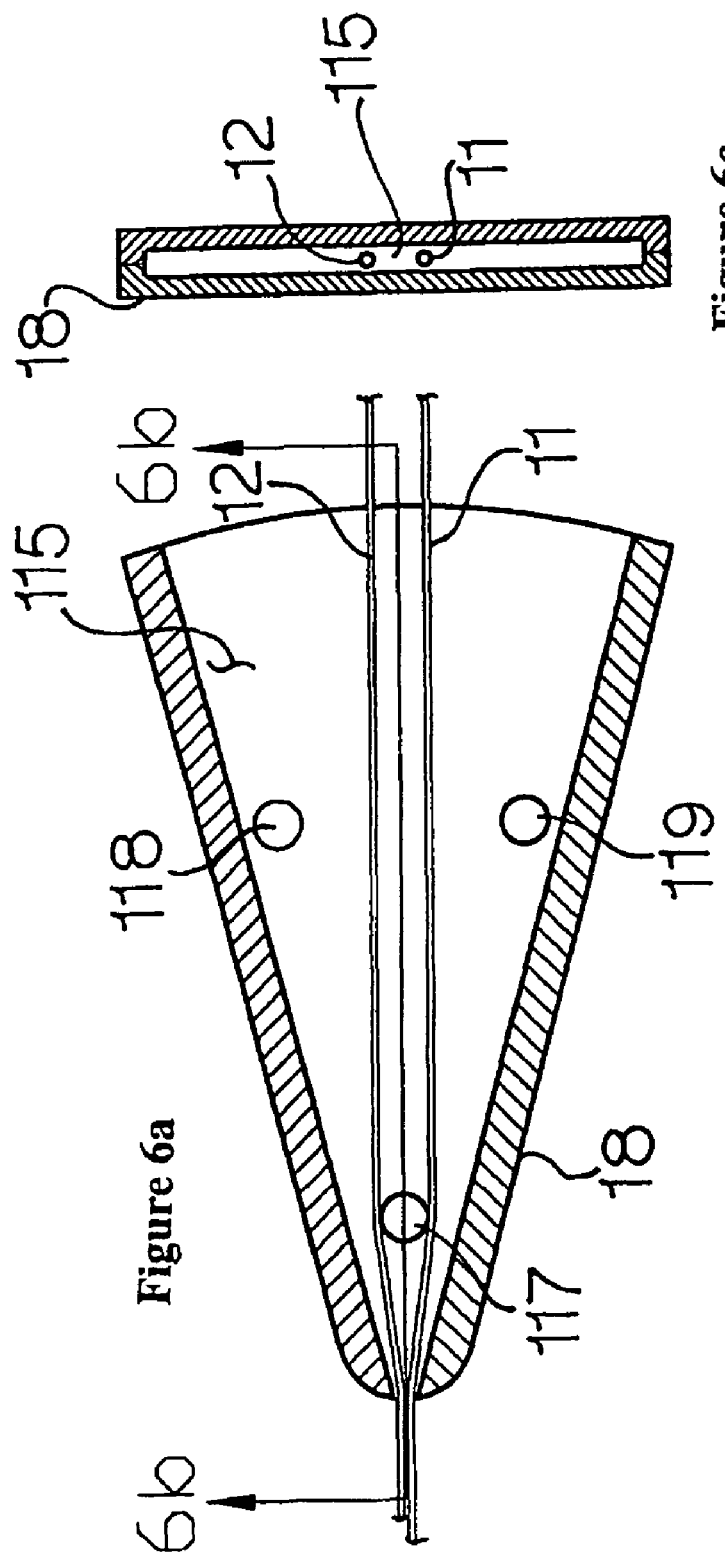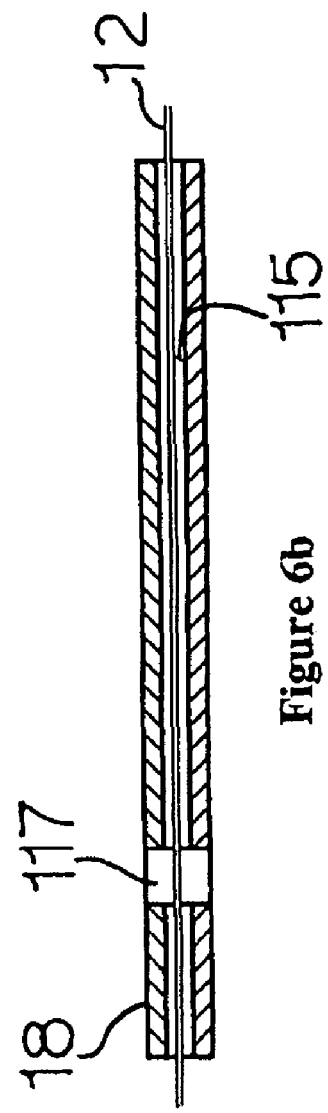
Figure 6a
Figure 6b
Figure 6c

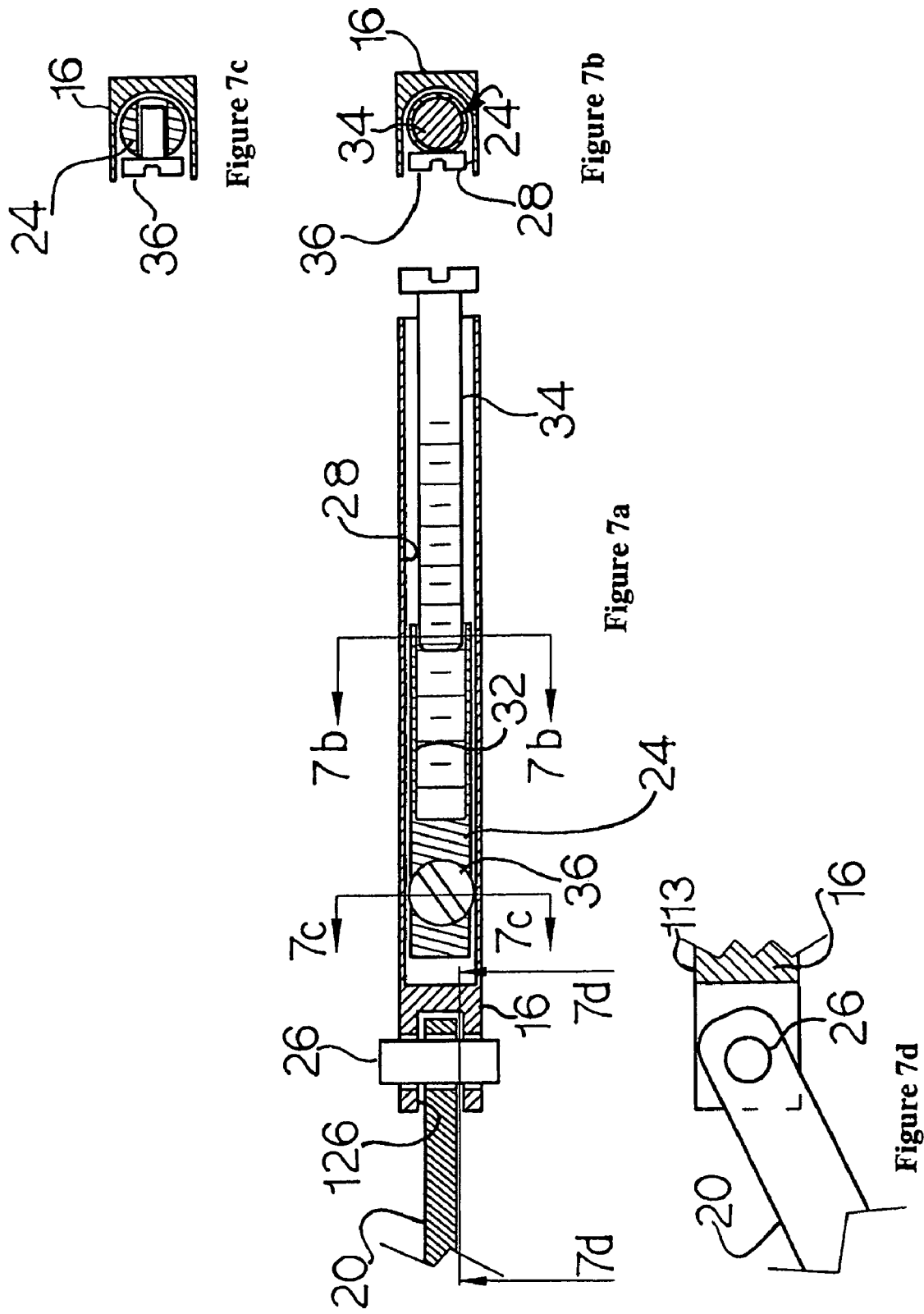

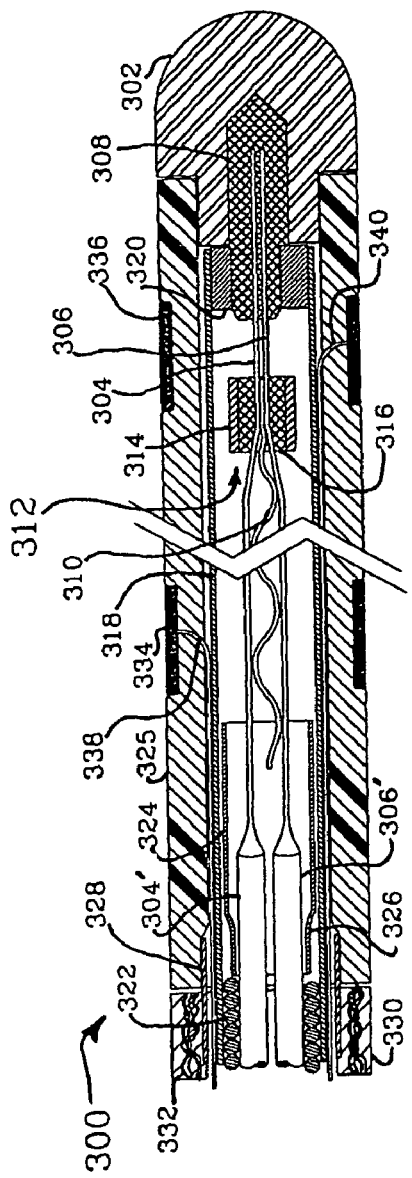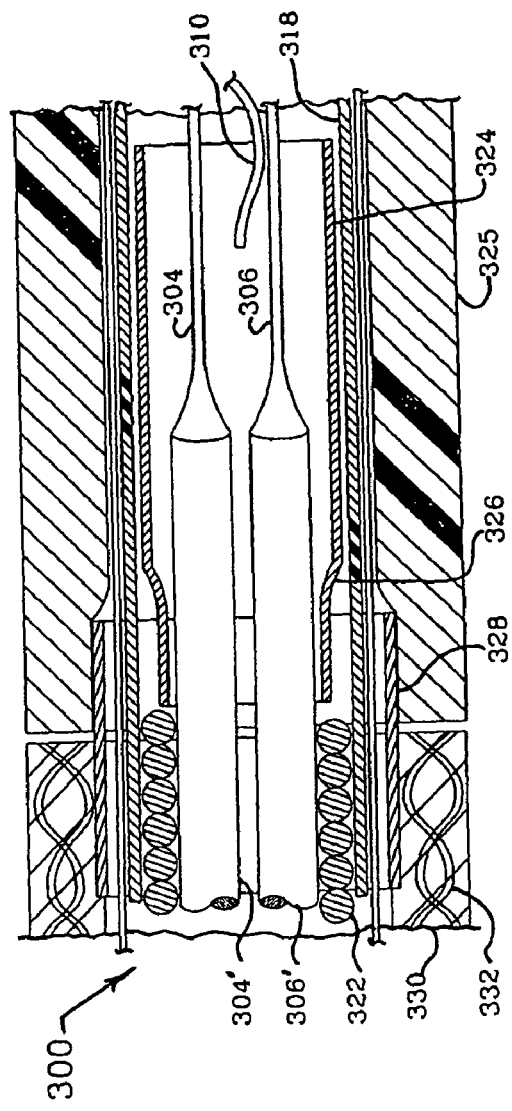
Figure 31
Figure 32

ELECTROPHYSIOLOGY/ABLATION CATHETER AND REMOTE ACTUATOR THEREFOR

CROSS-REFERENCE TO RELATED APPLICATIONS

This application is a continuation of U.S. application Ser. No. 10/260,242, filed 30 Sep. 2002, now pending (the '242 application), which is a divisional of U.S. application Ser. No. 09/232,866, filed 15 Jan. 1999, now abandoned (the '866 application), which is a continuation-in-part of U.S. application Ser. No. 08/880,080, filed 20 Jun. 1997, now U.S. Pat. No. 5,861,024 (the '080 application). The '242 application, the '866 application, and the '080 application are hereby expressly incorporated by reference in their entirety as though fully set forth herein.

BACKGROUND OF THE INVENTION a. Field of the Invention

The present invention relates to a catheter employed for diagnostic and/or therapeutic procedures in medicine, more specifically in minimally invasive cardiac electrophysiology studies and/or cardiac ablation procedures.

b. Description of the Prior Art

The primary device for an intra-cardiac electrophysiology study is a catheter with conductive electrodes at its distal portion [U.S. Pat. Nos. 5,156,151, 5,279,299, 5,415,633, 5,454,370, 5,465,717]. The distal portion of the catheter, where the electrodes are located, is commonly placed transvenously into the heart to monitor and/or record the intra-cardiac electrical signals during electrophysiology studies, or during intra-cardiac mapping. The function of these electrodes on the catheter is to conduct cardiac electrical signals to appropriate monitoring and recording devices.

During the diagnostic procedures, the catheter is also used as a medium to deliver low energy electrical pulses from a cardiac stimulator to the heart in order to evaluate the heart's response to the cardiac stimulator signals.

During therapeutic (cardiac ablation) procedures, electrical energy in the form of radio-frequency, microwave or high-voltage pulses is delivered from an appropriate energy source to the heart commonly via the catheter's distal electrode. The intent of this energy delivery is to destroy the site of the cardiac tissue that causes abnormality (arrhythmia) to the normal rhythm of the heart.

During such a minimally invasive cardiac ablation procedure the distal portion of a catheter, which usually comprises a plurality of spaced annular cylindrical electrodes and a distal electrode, is transvenously placed into the heart. The proximal end of the catheter, remote from the electrodes, has electrical leads which are connected to an appropriate recording and/or monitoring device. The intra-cardiac electrical signals can then be monitored and recorded.

A surface electrocardiogram, obtained from patient's skin, is concurrently compared with the intra-cardiac electrical signals. Typically, when a known catheter is employed for ablation procedures, an electrically conductive self adhesive skin patch is also placed on the patient's body. An electrical lead from this patch is connected to an electrical energy source. As the abnormal site of the cardiac tissue is detected with the catheter's distal electrode, its corresponding electrical lead is switched from the monitoring/recording device to the electrical energy source for ablation. At this time, electrical energy can be delivered to the heart from the catheter tip that is in contact with abnormal heart tissue. The self adhesive patch on the patient's body is the return path of the electrical energy to the energy source. This known ablation procedure, using a self-adhesive patch as the return path of electrical energy to the energy source, may result in a significant level of electrical "noise" that is generated by the energy source during the energy delivery period. This "noise" superimposes itself to both surface electrocardiograms and intra-cardiac signals obtained from the catheter. Cardiac signals contaminated with such "noise" have been found difficult to monitor during energy delivery period.

Intra-cardiac signals are commonly acquired for electrophysiology studies via a selected pair of a catheter's electrodes. The catheter is said to be used as a bi-polar probe when a cardiac signal is obtained between any pair of its electrodes. In some electrophysiology studies or cardiac mapping, however, the catheter is used as a uni-polar probe. When catheters of the prior art have been employed as a uni-polar probe, an additional reference electrode, that is not a part of the inserted catheter, is needed to complete the electrical circuit path. In such an arrangement, a second catheter is transvenously placed into the heart and this second catheter electrode functions as the reference electrode. U.S. Pat. No. 4,920,980 describes uni-polar and bio-polar application of cardiac catheters.

Currently most widely used and commercially available cardiac diagnostic and ablation catheters are sold for "one-time-use-only", and the entire catheter is discarded after a single use. Catheters of this type are relatively expensive. The catheter price and the convention of its "one-time-use-only" have an impact on the overall cost of cardiac electrophysiology and ablation procedures.

Typically, known catheters have a generally cylindrical electrically non-conductive body which has a plurality of spaced annular surface electrodes on the distal end with a hemispherically-shaped tip electrode. Each electrode has a relatively fine electrically conductive wire attached thereto and embedded in the catheter's main body (tube) and extending from the distal end to the proximal end (catheter handle) where the electrical connectors such as plugs or jacks are provided to be plugged into a corresponding sockets provided in recording and monitoring devices.

Typically, the main body of these catheters comprises a flexible tube constructed from polyurethane, nylon or some other electrically non-conductive flexible material with braided steel wires or other non metallic fibers in its wall as re-enforcing elements. An early example of such construction is that shown and described in U.S. Pat. No. 3,416,531 issued to M. L. Edwards. Catheters of this type are available in two general categories: a) those having a non-deflectable distal portion, an example of which is shown and described in U.S. Pat. No. 3,190,286 issued to R. W. Stokes, and b) those having a deflectable distal portion, as for example the catheter shown and described in U.S. Pat. No. 3,605,725 issued to I. E. Bentov. The distal portion of deflectable type catheters is typically made from non-braided flexible tube. This portion can be deformed into a variety of curved configurations with different radii of curvature by means of user input to a manual actuator on the catheter handle. The actuator is commonly internally linked to the catheter distal portion or the tip electrode by at least one steel tension or pull wire.

The proximal end of the tension or pull wire(s) is connected to a tensioning or puller mechanism in the handle. The distal end of the tension or pull wire(s) is fixed to the catheter distal electrode or anchored to a point on the catheter distal portion.

Catheters of this type also commonly comprise a flexible guide tube within the main body (tube) for bearing, in longitudinal or axial direction, the thrust or compression reaction of the flexible pull wire(s). An example of this latter type of configuration is shown and described in U.S. Pat. No. 3,906,938 issued to J. J. Fleischhacker and U.S. Pat. No. 3,521,620 issued to W. A. Cook. In the catheters of the prior art, such as those described in the aforesaid Cook and Fleischhacker patents, the inner flexible guide tube is formed by winding a tight coil of spring wire with the adjacent turns in contacting or closed relationship so that the inner guide tube will not compress longitudinally, but is freely flexible in bending. The tension wire(s) slides freely through this guide or coil spring type inner tube. The proximal end of the inner guide tube, in the aforesaid type catheters, is fixed to the catheter handle. The distal end of the inner guide tube is disposed in the distal portion of the catheter tubular main body. In one known catheter construction, one end of a bendable compression strut is seated on the distal end of the inner guide tube; and, the distal end of the pull wire(s) is fixed to the distal end of a bendable strut. Catheters employing such a strut are shown and described in the aforementioned Cook and Fleischhacker patents. See also U.S. Pat. No. 5,108,368 issued to Hammerslag for a catheter with a strut. In such known catheters, as tension is applied to the pull wire by the manual actuator on the catheter handle, the catheter distal portion assumes a curved configuration.

One of the distinctive parts of deflectable distal portion catheters is the pull wire mechanism that is commonly located in the proximal end (handle) of the catheter. This mechanism usually includes a manual actuator by which the catheter distal portion can be deflected. The primary difference among the designs of deflectable distal portion catheters is in the catheter handle, more specifically, the tension or pull wire mechanism. This mechanism transmits the manual force applied to the actuator on the handle to the catheter distal portion via the pull wire(s), for formation of a desirable radius of curvature at the distal portion of the catheter. A catheter employing a partially rotating "wheel" or "cam" mechanism for pull wire(s) is disclosed in U.S. Pat. No. 5,273,535 issued to S. D. Edwards et al. A rectilinearly moving arrangement for the pull wire is disclosed in U.S. Pat. No. 4,960,134 issued to W. W. Webster, Jr. A shapeable or bendable catheter handle for curvature formation on the distal portion of the catheter is disclosed in U.S. Pat. No. 5,318,525 issued to Scott West et al. A rotating collar or thumb-wheel type actuator is disclosed in U.S. Pat. No. 3,416,531, issued to M. L. Edwards.

The primary desirable performance features of the deflectable distal portion catheters are:

Ease of operation: ergonomic design to provide for the best use of physician's hand anatomy for catheter handling and usage;

A relatively low force requirement on the manual actuator of the catheter handle for formation of curvature at the catheter distal portion;

A comfortable range of displacement of the manual actuator to provide for a full range of curvature formation at the distal portion of the catheter; and, A simultaneous curvature formation and curvature retention at the distal portion of the catheter by a single action of the physician's finger(s).

The above desirable performance features for the catheters with deflectable distal portion have not been met by known commercially available catheters. The catheters of the prior art referenced in this document have not satisfied all of the desirable performance features mentioned above. For example, in the aforesaid U.S. Pat. No. 4,960,134, issued to Webster Jr., the sliding pull wire arrangement does not satisfy the low force requirement on the manual actuator of the catheter handle for formation of curvature at the catheter distal portion.

In the aforesaid U.S. Pat. No. 5,273,535, issued to Edward et al, a catheter is disclosed with two manual actuators on the catheter handle; one actuator is employed for formation of curvature at the distal portion of the catheter; and, the other actuator is used for retention of curvature or locking. This catheter requires two independent manual actions on both actuators in order to form and retain a desirable radius of curvature on the distal portion of the catheter. Therefore, the Catheter of U.S. Pat. No. 5,273,535 (Edwards et al) fails to satisfy a simultaneous curvature formation and curvature retention at the distal portion of the catheter by a single action of the operators hand.

Attempts have been made in the prior art catheters to provide a relatively laterally flexible distal portion for ease of its navigation through the vascular branches of the heart. In U.S. Pat. No. 5,203,772, issued to Gary R. Hammerslag et al, a steerable tip guide wire is disclosed for percutaneous transluminal insertion into the coronary vascular branches. The structure of the guide wire of the '772 Hammerslag et al, catheter comprises a spring coil wherein adjacent loops of the spring coil are "closed" or normally in contact with each other, except the loops that form the deflectable distal portion of the guide wire. The closed or contacting loops and the open or non-contacting loops of the guide wire of the '772 Hammerslag et al construction provide an axially relatively non-compressible structure in the region of the stacked loops, with a relatively laterally flexible distal portion formed in the region of the open loops.

U.S. Pat. No. 3,521,620 issued to William Cook discloses a similar guide wire structure having contacting and non-contacting portions with a deflectable tip for the same intended use as the aforementioned Hammerslag '772 guide wire.

The cardiac catheters of the prior art are not only expensive but are solely for "one-time-use-only". The catheter price and the convention of "one-time-use-only" increases the overall cost of electrophysiology and ablation procedures.

Presently employed known methods of cardiac ablation procedure and presently employed known ablation catheters have the disadvantage of requiring an electrically conductive patch on the patient skin during the procedure. The function of this patch is to return the delivered electrical charge, from the catheter electrode inside the heart, to the ablation energy source.

BRIEF SUMMARY OF THE INVENTION

It is an objective of the present invention to provide an electrophysiology catheter with a deflectable distal portion having the following features:

An ergonomically comfortable range of motion of the manual actuator for a full range of curvature formation at the distal portion of the catheter;

A low manual force requirement, applied by a single hand of the user, on the handle actuator for formation of curvature at the distal portion of the catheter;

A simultaneous curvature formation and curvature retention capability at the distal portion of the catheter by a single action of the operator's hand;

It is another objective of this invention to provide a catheter with a manual actuator on the catheter handle that is operated with the joint actions of index finger and the thumb in order to make the most efficient use of the anatomy of the operator's hand.

A further objective of this invention is to provide an electrophysiology and/or ablation catheter incorporating a sensor in the catheter handle to detect the longitudinal displacement of the pull/push wires and which can be correlated to the radius of curvature at the distal portion of the catheter for monitoring purposes.

Another objective of this invention is to provide an electromechanical drive system in the catheter handle to substitute the manual effort for formation of curvature at the distal portion of the catheter. The electromechanical drive system can also be controlled and manipulated via tele-communicated commands. The electromechanical system can also be over-ridden manually in the event of the failure of the drive unit.

A further objective of this invention is to provide an electrophysiology catheter having a disposable blood contacting portion comprising the catheter main body and electrodes with a deflectable distal segment. A re-useable portion comprising the actuator handle with its associated tip deflecting mechanism which is easily attachable/detachable from the blood contacting portion.

Another objective of the present invention is to provide an electrophysiology catheter incorporating an extra electrode on the catheter's exterior tube that can be employed as a reference electrode if desired for a uni-polar application of the catheter.

A further objective of this invention is to provide an electrophysiology catheter having a deflectable distal portion with a self contained heating element within its distal electrode that can be employed for ablation procedures Another objective of this invention is to provide a stand-alone electrophysiology catheter having deflectable distal portion with a self contained heating element within its distal electrode and a self contained power supply in its proximal handle portion that can be employed for cardiac mapping and cardiac ablation procedures.

A further objective of this invention is to provide an electrophysiology and/or ablation catheter with deflectable distal portion that can easily be manufactured in smallest possible size that can offer desirable bending characteristics at the catheter distal portion.

A further objective of this invention is to provide an electrophysiology catheter having independent pull/push wire length adjuster units for each pull/push wire in the catheter handle for independent removal of slack from each individual pull/push wire.

This invention provides a catheter employed for cardiac electrophysiology studies and/or cardiac ablation procedure. The catheter of this invention comprises of two main sub-structures. The first sub-structure is the blood contacting segment that includes: a) the catheter elongated tubular body, and b) the electrodes. The second sub-structure is the mechanism for formation of curvatures at the distal portion of the catheter. This mechanism includes: the catheter handle and its associated components.

The catheter presented in this invention offers the following desirable features:

A simultaneous curvature formation and curvature retention at the distal portion of the catheter by a single action of one hand of the user.

An ergonomic handle for curvature formation at the distal portion of the catheter that makes the most comfortable and efficient use of the user's hand anatomy.

A sensing unit within the catheter handle to be employed for displaying the radius of curvature at the catheter distal portion.

In one embodiment of the present invention the blood contacting portion is disposable, i.e. used only once, thereby maintaining all safety and effectiveness requirements, yet the overall catheter use cost is significantly reduced by allowing re-use of the non-blood contacting portions.

In one embodiment of this invention an ablation catheter with a self-heating element at its distal electrode is disclosed. Ablation with this catheter eliminates the need for a self-adhesive patch on the patient's body.

In one embodiment of the present invention an additional electrode, that can be employed as a reference electrode, is incorporated in the catheter for enabling uni-polar application of the catheter, thereby eliminating the need for the placement of a second catheter in the patient's heart.

The present invention offers the following additional attribute:

An electromechanical battery operated drive system in the catheter handle as an alternative for the manual drive components of the distal portion curvature formation mechanism.

The present invention utilizes a novel catheter construction which eliminates the compression loading of the inner guide tube and provides design flexibility and economies in construction.

BRIEF DESCRIPTION OF THE DRAWINGS

FIG. 2a is a overall view of the non-blood contacting segments of the catheter of FIG. 1;

FIG. 2b is an enlarged view of the encircled distal portion of the non-blood contacting segment of the catheter of FIG. 1;

FIG. 3a is an enlarged cross-section through the axis of inner guide tube of the catheter of FIG. 1;

FIG. 3b is a left end view of FIG. 3a;

FIG. 6a is a plan view of the delta-shaped actuator of the catheter of FIG. 1;

FIG. 6b is a section view taken along section-indicating line 6b-6b of FIG. 6a;

FIG. 6c is a right end view of FIG. 6a;

FIG. 7a Shows an enlarged view of the slider block and the length adjuster of the pull/push wire mechanism of the catheter of FIG. 1;

FIG. 7b is a section view taken along section-indicating lines 7b-7b of FIG. 7a;

FIG. 7c is a section view taken along section-indicating lines 7c-7c of FIG. 7a;

FIG. 7d is a section view taken along section-indicating lines 7d-7d of FIG. 7a;

FIG. 16b is a view similar to FIG. 16a showing the disk actuator rotated in a counterclockwise direction from the position of FIG. 16a;

FIG. 31 is a longitudinal cross-section of the distal portion of another embodiment of the electrophysiology/ablation catheter of the present invention;

FIG. 32 is an enlarged view of a portion of FIG. 31;

DETAILED DESCRIPTION OF THE INVENTION

Figure 1:
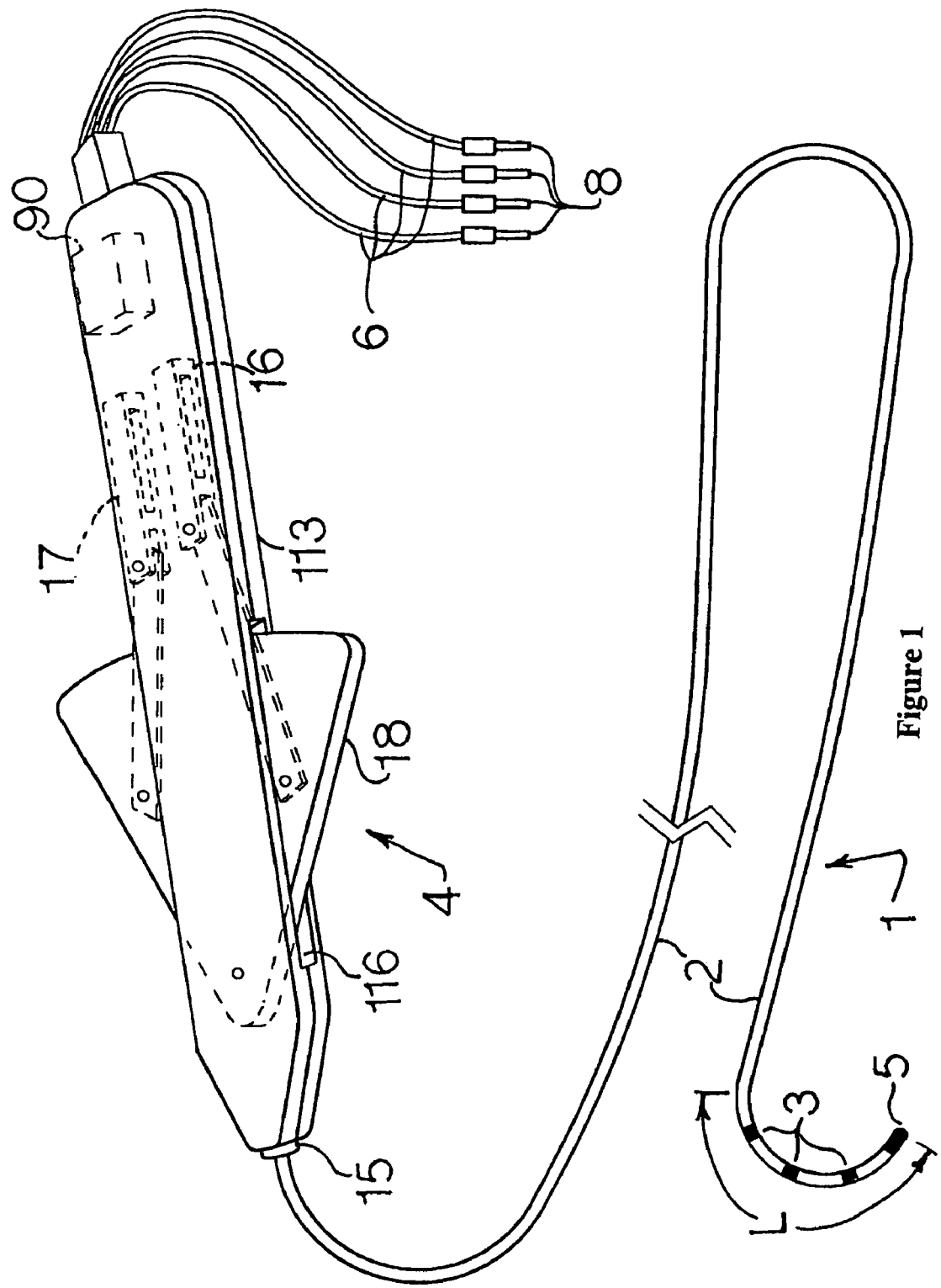
FIG. 1 is a perspective view of the cardiac catheter presented in this invention.

Referring now to the drawings, which are not intended to limit the invention, FIG. 1 illustrates a perspective view of one embodiment of the catheter assembly including the elongated flexible main body indicated generally at 1. The catheter of this invention is comprised of two main components: i) a blood contacting segment that includes the catheter elongated exterior tubular body 2 with a plurality of spaced electrodes 3 and a distal electrode 5; and ii) a sub-assembly comprising the actuator mechanism for affecting the catheter distal curvature which includes a catheter handle and its associated components which is indicated generally at 4. The blood contacting segment 2 comprises of an elongated cylindrical electrically non-conducting preferably braided main exterior tube 2 with a plurality of spaced annular surface electrodes 3 on its distal portion and a hemispherically shaped solid or hollow cup-shaped distal electrode 5. The distal portion of the catheter denoted by the reference character "L" is a non-braided tube that is significantly more flexible or softer than the rest of main exterior tube 2. Each of the electrodes 3,5 has a fine electrical conductor wire 6 attached thereto, which extends within the length of the catheter and through handle 4 and outwardly to a corresponding one of the plugs/jacks 8 disposed at the proximal end of the catheter handle sub-assembly 4.

FIG. 2a shows the catheter assembly 1 of the present invention with the tubular body 2 removed, thereby exposing the non-blood contacting segment of the catheter generally denoted by reference numeral 9.

When the first sub-structure 2 is assembled over the inner guide tube 9 of the catheter handle 4, the distal portion 10 of the inner guide tube 9 is situated or disposed in the distal non-braided portion of the catheter exterior tube 2. The catheter distal portion L of FIG. 1 assumes the same curved configurations as that of the distal portion 10 of the inner guide tube 9 in response to the user manipulations of the actuator 18 on the catheter handle 4.

Referring to FIGS. 2a and 2b the non-blood contacting segment of the catheter of this invention includes:

an inner guide tube indicated generally at 9, a pair of tension/compression members 11, 12 comprising flattened portions 11' and 12', a catheter handle 4, and a plurality of electrical plugs 8

Referring to FIG. 2b, the entire length of the inner guide tube 9 and its distal portion along the length 10 is disposed within the tubular body 2 of FIG. 1. FIGS. 3a and 3b show the area of FIG. 2b in further enlargement wherein the inner guide tube 9 is a flexible body made from spring wire in the region denoted by reference numeral 14; and, is preferably formed as a tightly wound spring with adjacent coils contacting or closed windings. The inner guide tube 9 has disposed therein at least two tension/compression members in the form of wires 11 and 12. The tension/compression members 11, 12 have a generally circular cross-section and extend preferably along the length of the elongated inner guide tube 9 and have a generally flattened ribbon-like configuration 11', 12' in the region 10 of guide tube 9. The inner guide tube 9 is formed to have generally circular cross-section. The windings of the distal portion 10 of the inner guide tube 9 are permanently stretched or wound in the opened condition to provide an easily bendable structure.

Figure 4:
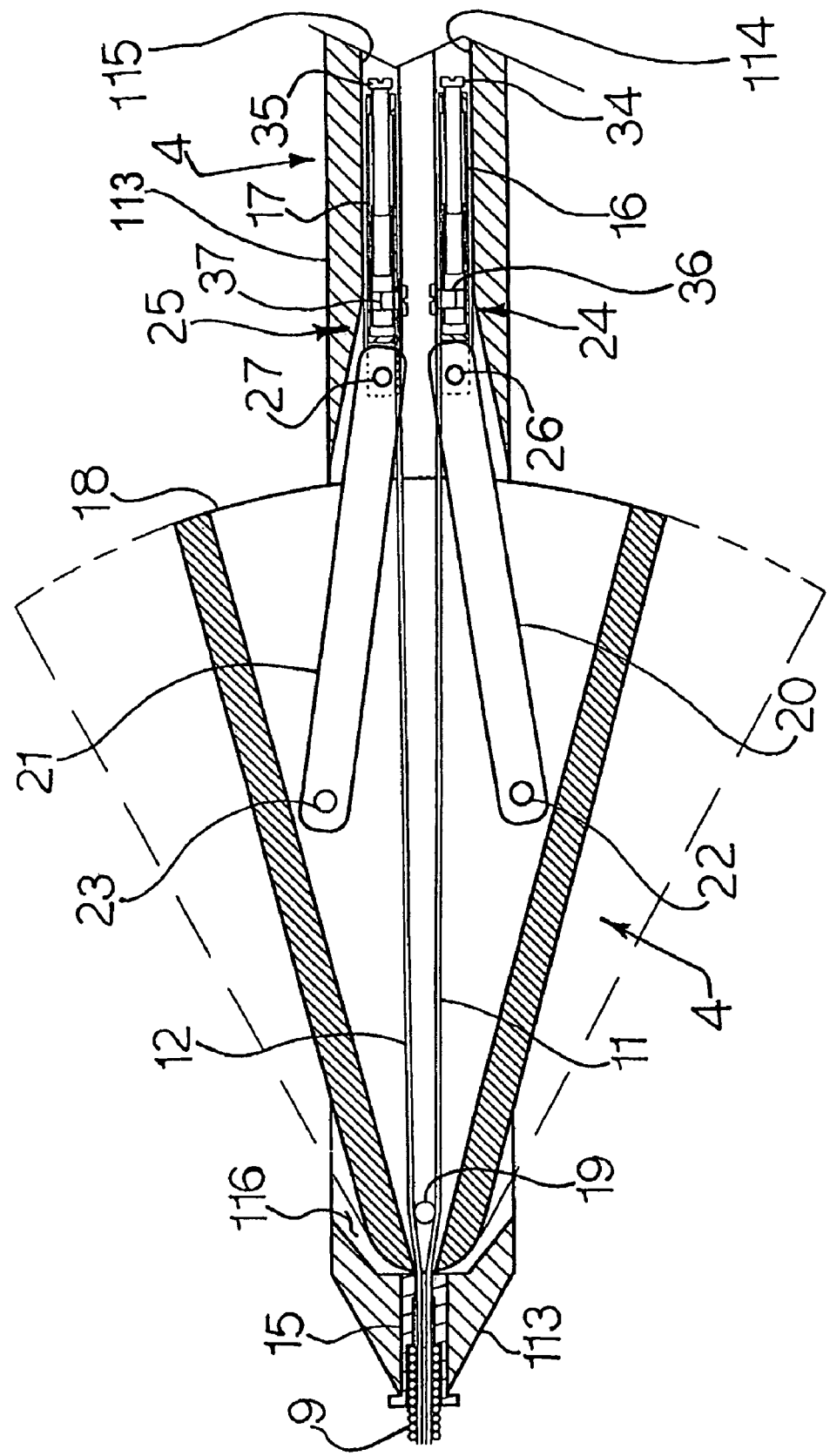
FIG. 4 Shows a top sectional view of the slider-crank pull/push wire mechanism of the catheter handle of FIG. 1.

FIG. 4 shows an enlarged sectional view of the pull/push mechanism of the catheter handle 4. The proximal end of the inner guide tube 9 is seated on the catheter handle nose 15 which is attached to an end of block or body 113 of handle 4. The tension/compression members 111 and 12 are each fixed at one end to the distal end of the guide tube 9 in the region 10. The other end of each of the tension/compression members 11 and 12 is attached to one of the pull/push length adjuster units 16 and 17 which are slidingly mounted in grooves or slots 114, 115 mounted in block 113. With this arrangement, the distal portion 10 of the inner guide tube 9 can be formed into a curved configuration by user movement of the manual actuator member 18 in either transverse direction as indicated by the dashed outline in FIG. 4 about pivot pin 19 by which actuator 18 is mounted to block 113 in a through-slot 116.

Figure 5:
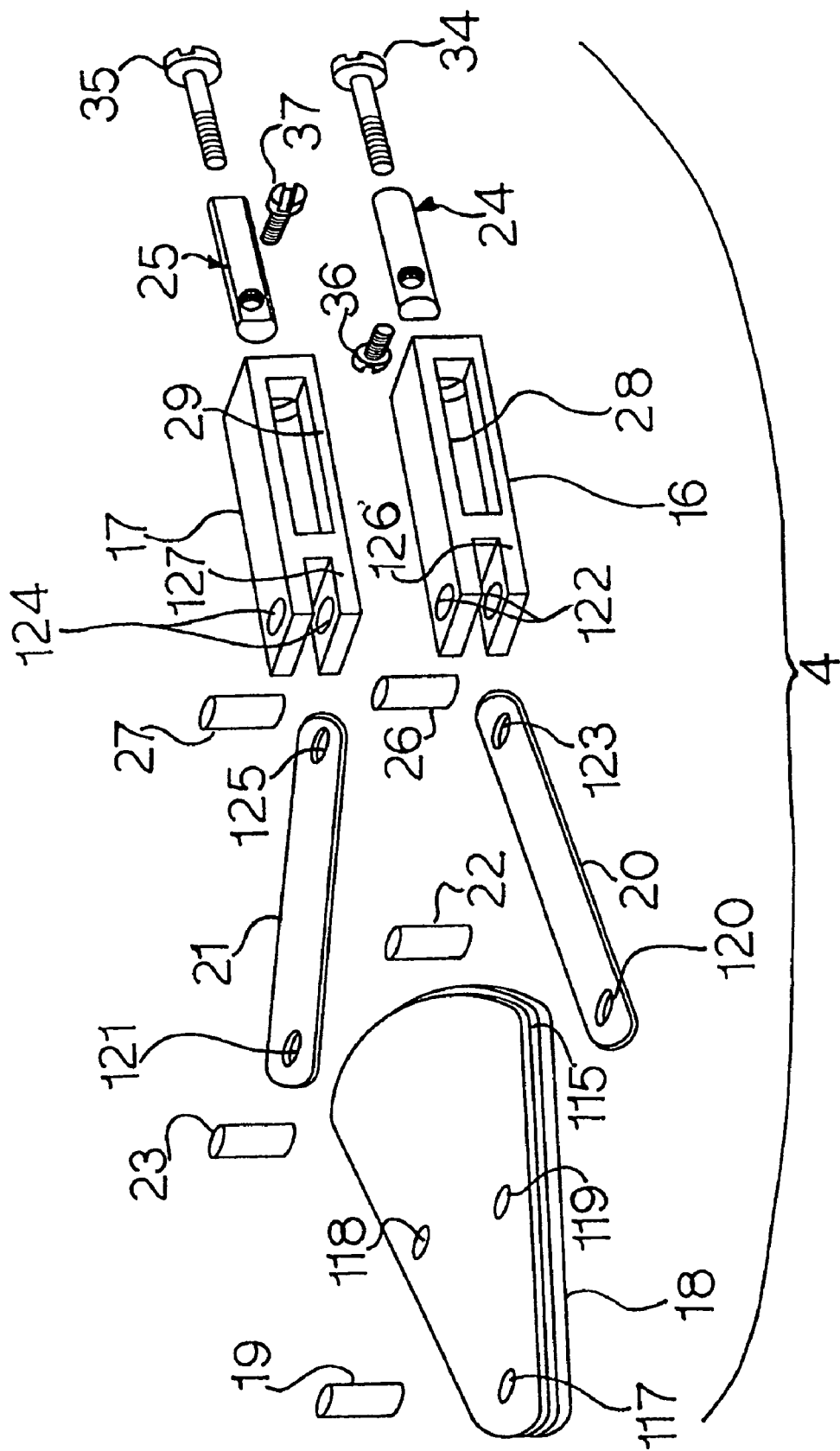
FIG. 5 Shows an exploded view of the slider-crank pull/push wire mechanism of the catheter of FIG. 1.

FIG. 5 shows an exploded view of the pull/push mechanism removed from the catheter handle block 113. Upon movement of actuator 18 the mechanism 4 is operative for applying tension to one of the tension/compression members 11, 12, and thereby affecting curvature formation at the distal portion L of the catheter of this invention. In one embodiment, this pull/push mechanism comprises two symmetrically coupled slider-crank linkages, hereinafter described, that share the actuator member 18 which is preferably formed into a circular segment or delta shape with a hollowed out portion 115 formed therearound.

Referring to FIGS. 4 and 5, the actuator 18 is disposed freely within slot 116 of the handle block 113. The proximal apex of this actuator 18 is hinged within the proximal front end of the handle housing block 113 by a pin 19 received through aperture 117 in actuator 18. A pair of connecting rods 20 and 21 are received in the hollowed-out portion 115 formed in actuator 18 and are independently and symmetrically hinged each at one end through aperture 120, 121 respectively to the actuator 18 by pins 22 and 23 respectively, received through aperture 118, 119 formed in actuator 18. The opposite ends of the connecting rods 20 and 21 are each independently hinged each to an end of two separate and identical slider links 16 and 17 by pins 26 and 27 respectively. Pin 26 is received in aperture 122 in slider 16, with pin 26 passing through aperture 123 in rod 20; and, pin 27 is received in aperture 124 in slider 17, and pin 27 passes through aperture 125 in rod 21. The end of rod 20 pivoted by pin 26 is received and articulated in a slot 126 formed in slider 16; and, the end of rod 21 pivoted about pin 27, is received and articulated in a slot 127 formed in slider 17.

Referring to FIGS. 4 and 5 the slider links 16 and 17 each contain a pull/push member length adjuster unit indicated generally at 24 and 25 respectively.

Referring to FIGS. 4, 6b, and 6c, one of the pull/push or tension/compression members 12 is shown as extending through hollow 115 in actuator 18 and is connected to slider 17; and, pull/push member 11 extends through hollow or slot 115 and is connected to slider 16.

Referring to FIGS. 7a 7b, 7c, and 7d, one of the slider blocks 16 is illustrated with its associated pull/push member length adjuster unit 24 and its sub-components. The pull/push member length adjuster 24 is disposed in a slider block 16 having a longitudinally extending blind cylindrical cavity 28.

A generally cylindrical rod or adjusting member indicated generally at 24 with an internally threaded hole or bore 32 formed in the right end thereof is slidingly disposed freely within the cavity 28 formed therein. The longitudinal position of rod 24 with respect to the slider block 16 can be adjusted by the adjusting screw 34 threaded into bore 32. A pull/push member fastener 36 fixes the proximal end of a pull/push member 12 (not shown in FIGS. 7a-7d) to rod 24. FIG. 7d shows an enlarged view of the typical hinged attachment between one end of the connecting rod 20 and slider block 16 by pin 26. The function of each individual and independent pull/push member length adjusters such as adjuster 24 is to independently remove the slack from the corresponding pull/push member 11, 12 that extends from catheter distal portion to the catheter handle 4.

Figure 8:
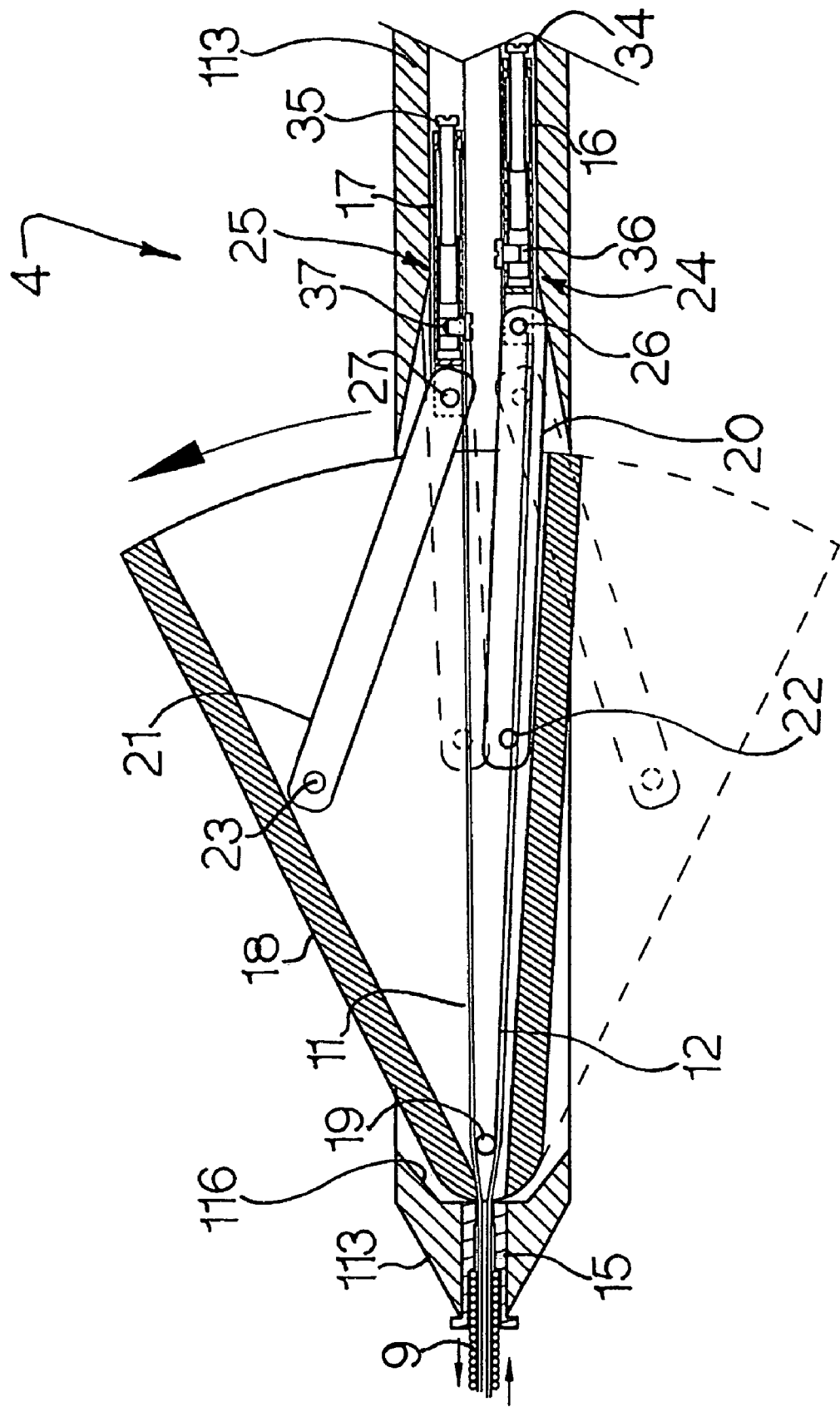
FIG. 8 Shows a plan sectional view of the catheter handle with the actuator partially rotated counterclockwise, thereby pulling one tension/compression member and pushing the other tension/compression member.

Referring to FIG. 8, actuator member 18 is shown in solid outline and moved counterclockwise from the neutral position of FIGS. 1 and 4. In the position shown in FIG. 8, rod 20 has moved slider 16 rightward pulling on tension/compression member 12. Rod 21 has moved slider 17 leftward pushing on member 11. The distal portion of the catheter of this invention can simultaneously be curved to different radii of curvature and retained at the desired curvature by a single action of the operator's finger. The slider-crank pull/push mechanism of the catheter handle of this invention operates near its "top-dead-center" or aligned position. An inherent property of a slider-crank mechanism operating near its top-dead-center position is a high-gain force amplification between the input force on the crank link or actuator 18, and the output force on the slider link. Therefore, catheter of this invention requires a low actuating force on the actuator 18, transmitted through the crank link, for assuming a full range of pull on one of the members 11, 12 for affecting curvature at the distal portion of the catheter. Any curvature formed at the catheter distal portion by this mechanism will retain its configuration. This is because the elastic potential energy stored in the deflected distal portion of the catheter cannot provide a sufficient pull on the tensioned members 11 or 12 as the case may be to move the crank link and thus actuator 18 to disturb the assumed configuration of the slider-crank mechanism which is near the "top-dead-center".

The geometric shape and dimensions of the delta-shaped actuator 18 are designed to comfortably fit between the thumb and index fingers of an operator's hand. The relative magnitudes of these geometric dimensions, crank length (distance between pin 19 and pins 22, 23) and the length of the connecting rods 20 and 21 are determined such that a comfortable range of actuator 18 rotation in two opposite directions results in formation of the full range of curvature, in opposite directions, at the distal portion of the catheter. It will be understood that rotation of actuator 18 in one direction is affected by the user's thumb of the hand grasping the handle 113; and, rotation of actuator 18 in the opposite direction is affected by at least one other finger of the same grasping hand.

Referring to FIG. 8 the rotation of link 18 in a counter-clockwise direction to the position shown in solid outline has caused the rectilinear displacements of slider blocks 16 and 17 in two opposite directions, i.e. slider 17 has moved to the left and slider 16 has moved to the right. The movement of actuator 18 by the user to the position shown in solid outline FIG. 8 affects formation of a curvature in a counterclockwise direction, at the distal portion of the catheter, as the result of tension in the pull/push member 12. It will be understood that a clockwise curvature formation can be achieved at the distal portion of the catheter when the manual actuator 18 is rotated in a clockwise direction to the position shown in dashed outline in FIG. 8 which causes slider block 16 to be moved to the left and slider block 17 to be moved to the right when links or rods 21, 20 are moved to the positions shown respectively in dashed line.

Referring to FIGS. 9, 10, 11, 12, and 13 an alternative embodiment 4' of the catheter handle is shown with a cam-follower type pull/push mechanism for affecting formation of curvature at the distal portion of the catheter upon movement of actuator 128. The pivoted delta shaped actuator 128 is disposed to pivot freely about pin 43 within the handle 113'.

Figure 10:
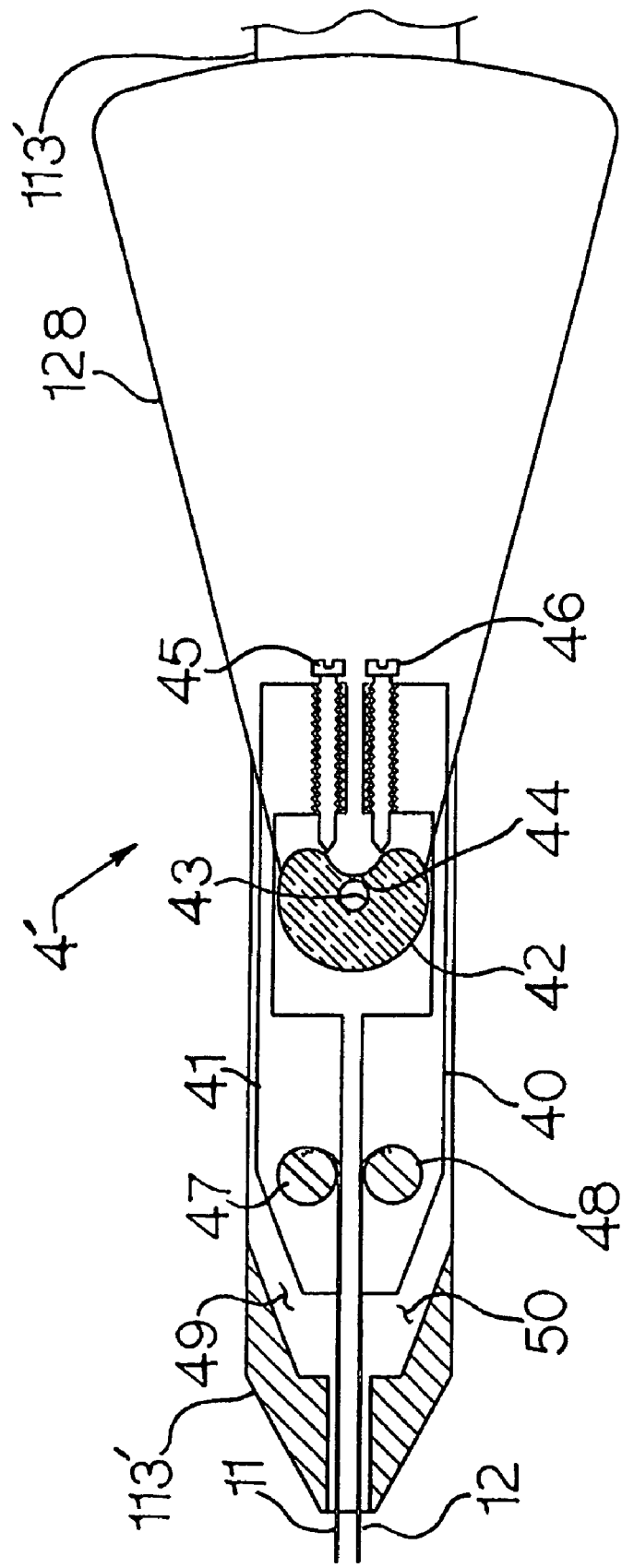
FIG. 10 Shows an enlarged view of the cam-follower mechanism of FIG. 9.

Referring to FIG. 10, the mechanism of handle 4' comprises two symmetrically coupled followers 40 and 41 disposed for sliding movement on block 113' and with a single rotating cam 42 as the driver. The cam 42 is rigidly attached to the apex of the delta-shaped actuator 128 for rotation therewith. The center 44 of cam 42 is pivoted within the catheter handle body 113' about a pin 43.

The two sliding followers 40 and 41 are driven by cam 42. Each of the sliding followers 40 and 41 includes an adjusting screw 45 and 46 respectively. The tip of each of these adjusting screws 45, 46 are anchored to the cam profile and provides the contacting point between the followers 40 and 41 and the profile of the cam 42. The distal ends of pull/push members 11 and 12 are individually fastened to the corresponding followers 40 and 41 respectively by the screws 47, 48 threaded respectively into followers 41, 40. The slack in each pull/push member can independently be removed by adjusting the screws 47 and/or 48.

Each of the two followers 40 and 41 slides freely, in one of the straight grooves 49 and 50 respectively, provided in the catheter handle 113'.

Figure 11:
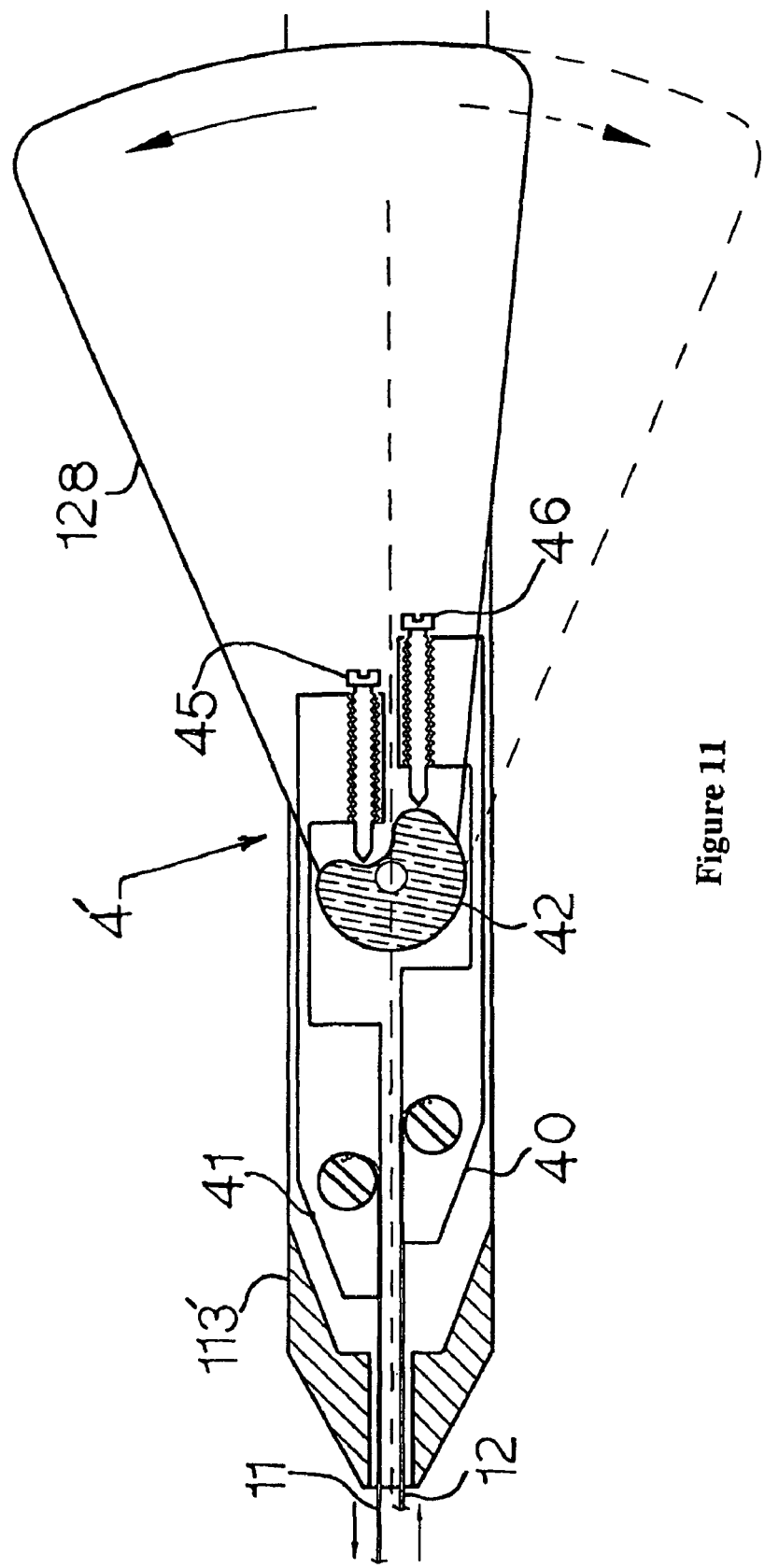
FIG. 11 Shows a plan sectional view of the catheter handle with the cam-follower mechanism and the actuator partially rotated counterclockwise, thereby pulling one tension/compression member and pushing the other tension/compression member.

Referring to FIG. 11 the actuator member 128 is shown rotated counterclockwise from the position shown in FIG. 10, wherein cam 42 has caused rectilinear displacements of the two followers 40 and 41 in opposite directions. Follower 40 has been moved rightward tensioning pull/push member 12; and follower 41 has been moved leftward pushing on pull/push member 11. This movement of followers 40, 41 results in formation of a curvature, in a counterclockwise direction, at the distal portion of the catheter. It will be understood that a clockwise curvature formation can be achieved at the distal portion of the catheter when the manual actuator 128 is rotated in a clockwise direction to the position shown in dashed outline in FIG. 11.

Figure 12:
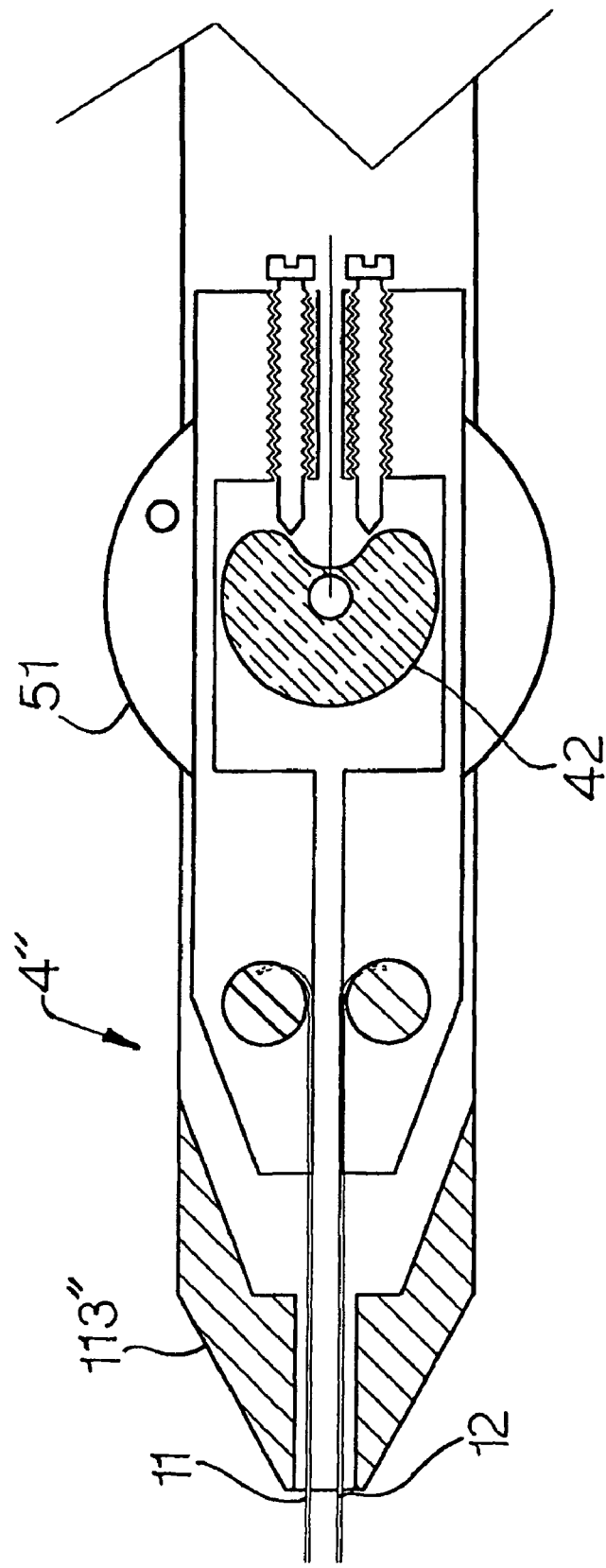
FIG. 12 Shows a plan sectional view of the cam-follower mechanism with a circular disc actuator.

Referring to FIG. 12 an alternative arrangement of the actuator handle is shown generally at 4", having a handle 113" and wherein the user actuator member comprises a circular disk-shaped actuator 51 which is attached to cam 42 in a torque-transmitting arrangement. Cam 42 is shown in the neutral position in FIG. 12. It will be understood that user rotation of actuator disk 51 rotates cam 42.

Figure 13:
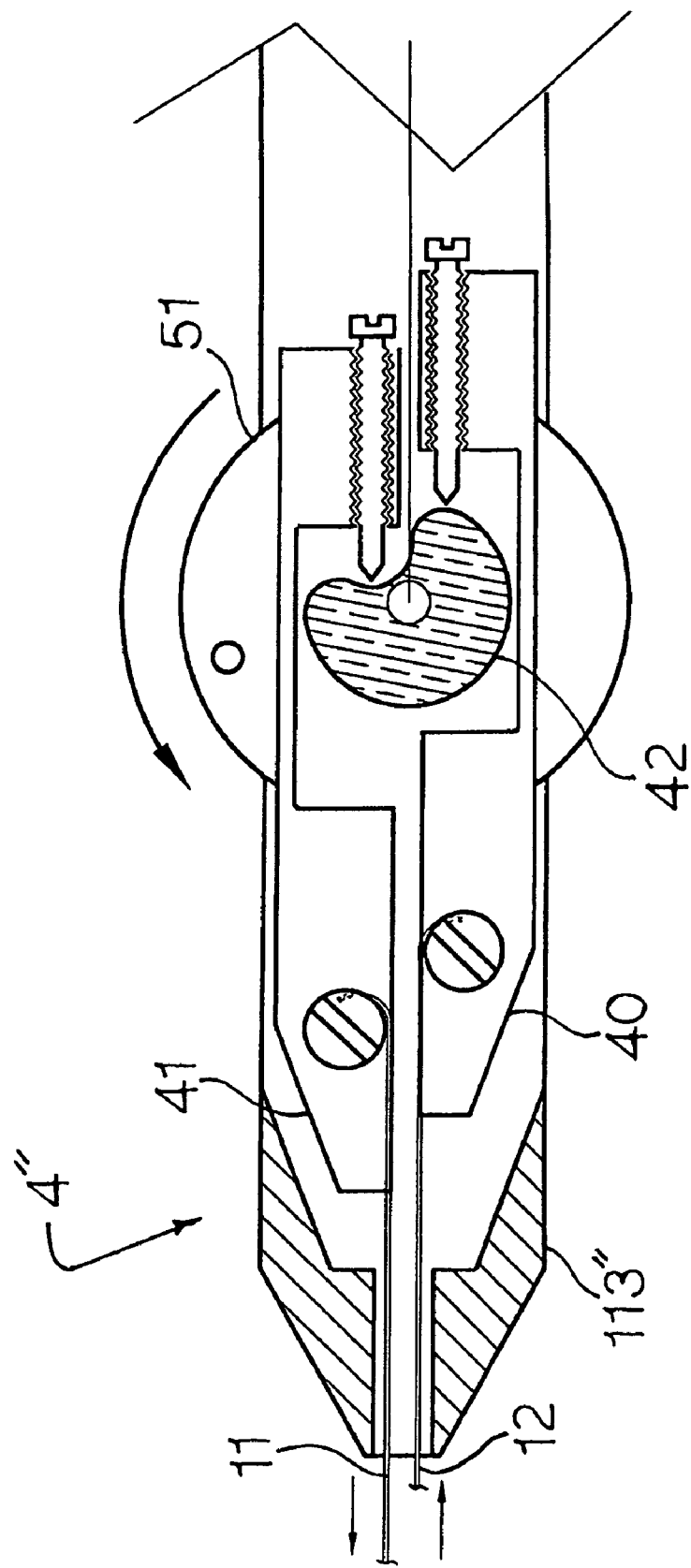
FIG. 13 Shows the cam-follower mechanism with a circular disc actuator partially rotated counterclockwise, thereby pulling one tension/compression member and pushing the other tension/compression member.

Referring to FIG. 13, the actuator disk 51 has been rotated in a counterclockwise direction as indicated by the arrow to place cam 42 in the position shown in solid outline in FIG. 13. In FIG. 13, follower 40 has been moved rightward from the position of FIG. 12, tensioning or pulling member 12; and follower 41 has been moved leftward from the FIG. 12 position, resulting in pushing on member 11.

Figure 14:
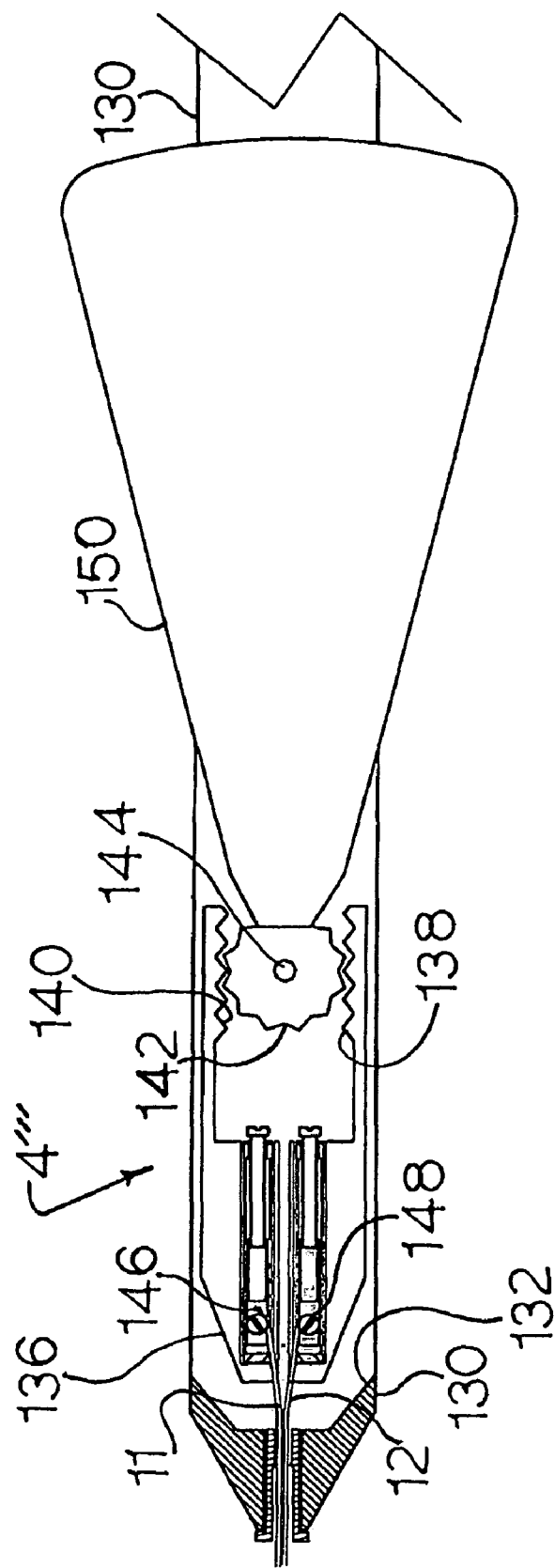
FIG. 14 Shows a plan sectional view of a further embodiment of a rack-pinion mechanism of the catheter handle.

Referring to FIG. 14 a further alternative embodiment of the actuator handle is shown generally at 4'41 for the catheter of this invention wherein handle or body 130 has a groove or through-slot 132 with a pair of parallel oppositely disposed sliders 134, 136, disposed therein, each having a rack gear formed thereon as denoted respectively by reference numerals 138, 140. Rack gears 138, 140 are engaged on opposite sides of a common pinion gear 142. Pinion 142 rotates freely within the catheter handle 130 about pin 144 secured through body 130. Each slider 134, 136 includes a pull/push member anchoring or attachment screw 146, 148 to which one end of pull/push members 11, 12 are attached respectively. The apex of a delta-shaped manual actuator 150 is fixed to the pinion 142 in torque transmitting arrangement and is shown in the neutral position in FIG. 14.

Figure 15:
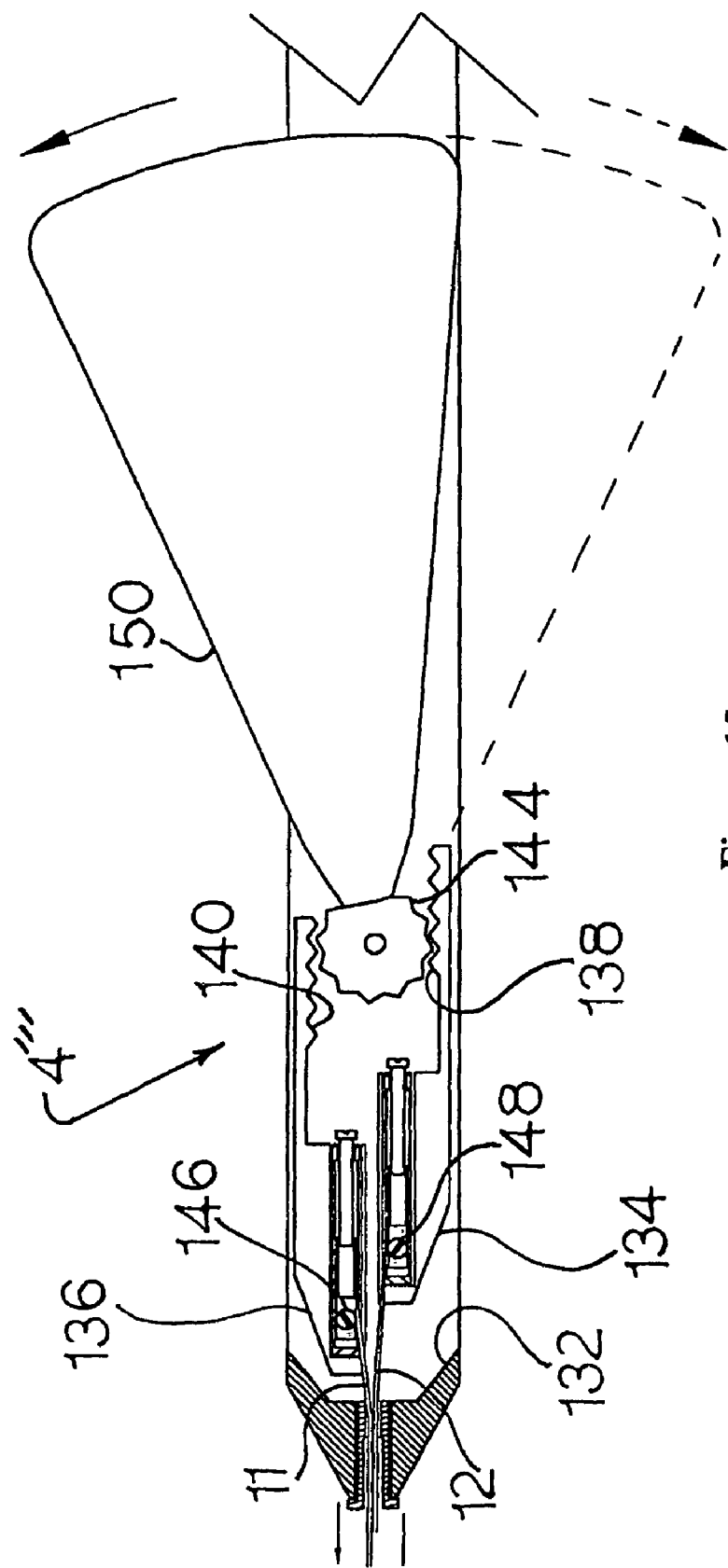
FIG. 15 Shows a plan sectional view of the catheter handle with the rack-pinion mechanism and the actuator partially rotated counterclockwise, thereby pulling one tension/compression member and pushing the other tension/compression member.

Referring to FIG. 15 the manual actuator 150 is shown rotated counterclockwise from the position of FIG. 14, resulting in the rectilinear displacements of the slider 136 to the left and slider 134 to the right, pulling on pull/push member 12 and pushing on pull/push member 11. The proximal ends of the pull/push member 11 and 12 are fixed to the sliders 136, 134 respectively by fasteners such as screws 146 and 148. It will be understood that the distal end of the pull/push members 11 and 12 are fixed to the distal ends of the elongated inner guide tube 9. It will be also understood that the actuator 150 may also be moved in the clockwise direction to the position shown in dashed outline in FIG. 15, resulting in opposite movement of slider 134, 136. With either counterclockwise or clockwise rotations of actuator 150 the rectilinear displacement of the slider racks 134, 136 is in opposite directions and results in formation of curvature at the distal portion of the catheter.

Figure 16A:
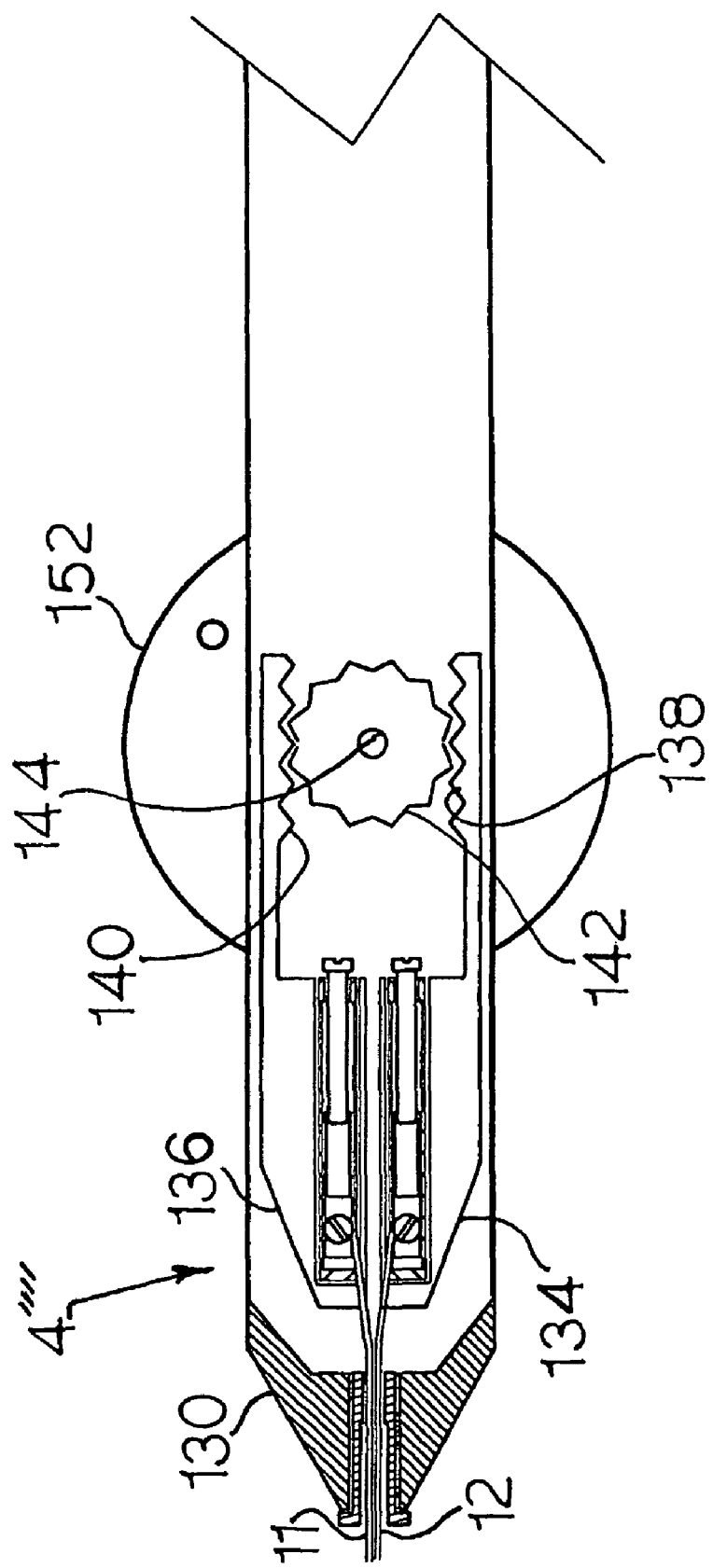
FIG. 16a Shows a plan sectional view of the catheter handle with rack-pinion mechanism having a circular disc actuator.

Referring to FIG. 16(a), another embodiment of the actuator handle is indicated generally at 4"", wherein pinion gear 142 is attached to a circular actuator 152 in torque transmitting arrangement.

Figure 16B:
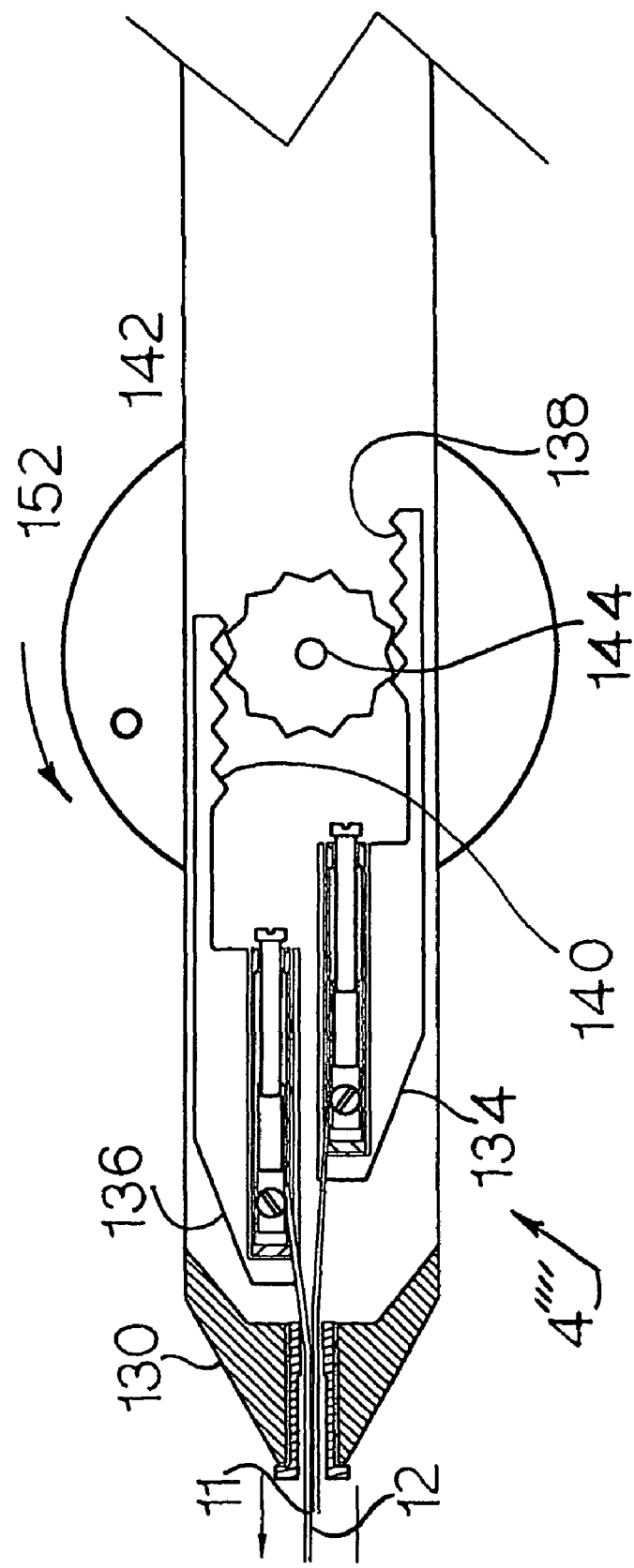

Referring to FIG. 16(b), as the user rotates actuator disk 152 in a counterclockwise direction as shown by the arrow slider 136 is moved leftward, and slider 134 is moved rightward from the neutral position shown in FIG. 16(a).

Figure 17:
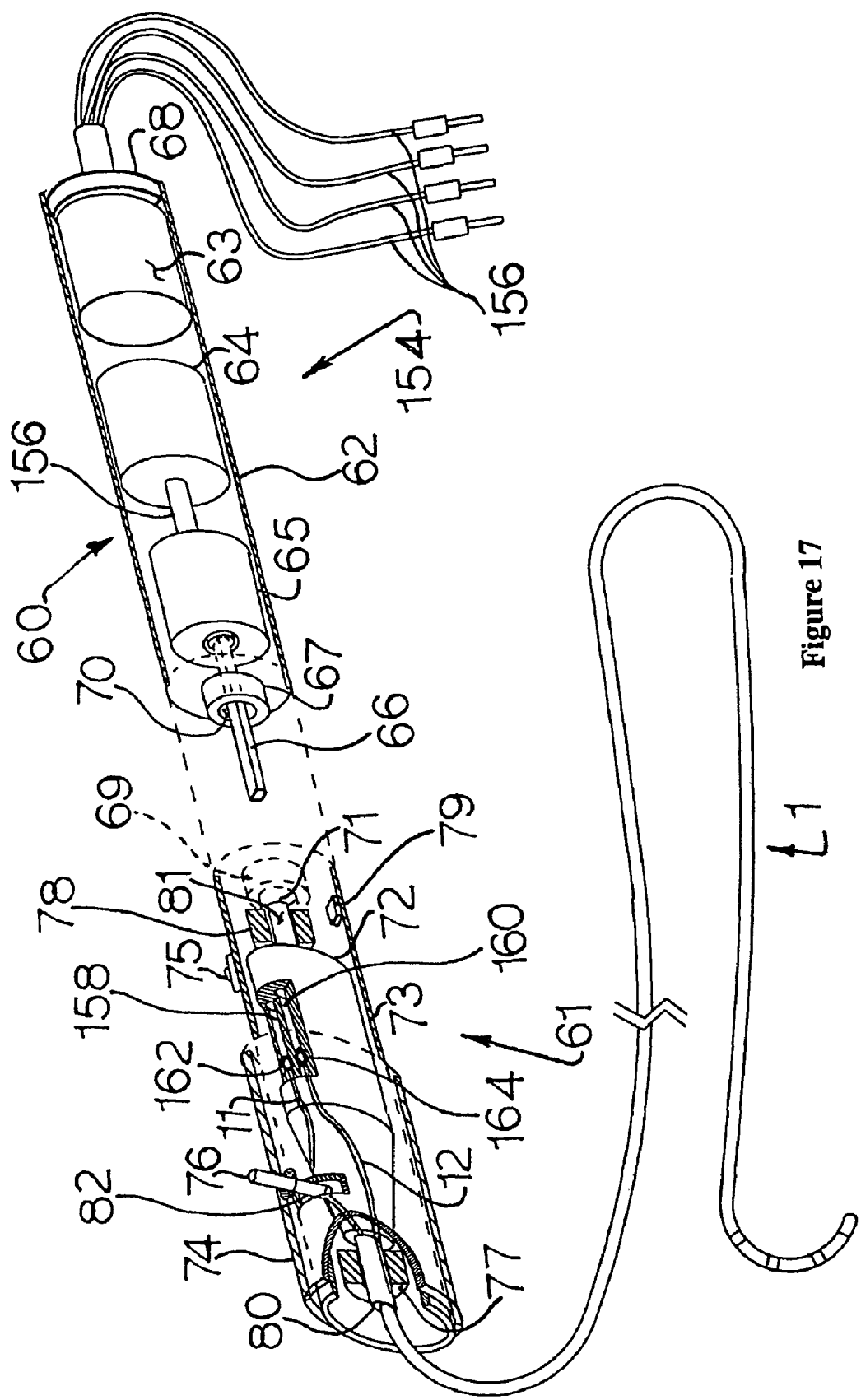
FIG. 17 Shows a perspective view of yet another embodiment of the catheter handle with an electromechanical drive system and associated control components in two main segments 60 and 61.

Referring to FIG. 17, another alternative embodiment has the handle assembly that is indicated generally at 154. Handle assembly 154 includes an electromechanical battery operated drive system that is substituted for the manually actuated pull/push mechanism of the embodiments 4-4"". The embodiment 154 comprises two main subsystems indicated generally at 60 and 61. The first sub-system 60 of the embodiment 154 is the "lower" portion of the catheter handle that includes:

a cylindrical housing 62, having disposed therein a battery 63;

an electrical motor 64, which is connected to battery 63 disposed at the right hand end of housing 62;

a speed reduction gear box 65, driven by motor shaft 156, and which has an output drive shaft 66;

a multi connector junction plug 67 is disposed on the front end of the housing 62; and, an electronic module 68 is provided on this end of housing 62 adjacent to battery 63 for receiving computer and/or tele-communication signals. Battery 63 can either be disposable or re-chargeable.

The second sub-system 61 has a multi connector proximal end jack 69 disposed in the right hand end of housing 73. All electrical wires of the catheter, including the electrode conductors are terminated to the terminals (not shown) of jack 69. The corresponding electrical leads of sub-system 60 are terminated at terminals (not shown) of plug 67.

The electrical motor 64 and motor speed reduction gear box 65 are disposed within the cylindrical housing 60 adjacent the left hand end. The coupling drive shaft 66 extends from the gear box 65 through a cylindrical collar 70 in the left end of the housing 62. The drive shaft 66 can freely rotate within the front end collar 70 of the housing 62. The end of the drive shaft 66 is coupled to the left hand end 71 of the core 72 of the sub-system 61. In operation either clockwise or counterclockwise rotation of the drive shaft 66 results in driving core mechanism 72 and a corresponding curvature formation respectively at the catheter distal portion.

The second sub-system 61 of the embodiment 154 comprises the front or left hand portion of the catheter handle end and includes:

a cylindrical housing 73;

a manual back-up actuator 74 in the form of a tubular member disposed concentrically over housing 73;

a motor control switch 75;

the multi connector junction jack 69 is disposed inside the right hand end of the cylindrical housing 73;

a connecting rod or pin 76 interconnects manual drive actuator 74 to core 72 through a slot 82 formed in housing 73;

a front bearing support 77 is disposed in housing 73 adjacent the left end thereof;

a rear bearing support 78 is disposed in housing 73 adjacent the right hand end thereof; and, an angular displacement sensor 79 is disposed in housing 73 and located at the right hand end thereof for sensing rotation of core 72 with respect to housing 73 of sub-system 61.

The core 72 of sub-system 61 includes two identical pull/push member length adjusters 158, 160 which are each respectively connected to one of the pull/push members 11, 12 of the catheter 1. These adjusters are disposed, side-by-side, and parallel to the longitudinal axis of the housing 73, within and near the surface of the cylindrical solid portion of the core 72. The core 72 of the sub-system 61 has a left end shaft 80 extending therefrom and a right end shaft 81 extending therefrom in a direction opposite shaft 80 and aligned therewith. Shaft 80, 81 are supported by rotary bearings 77 and 78 respectively disposed in housing 73; and thus, the core 72 can freely rotate within the housing 73 about its longitudinal axis.

A backup manual actuator 74 comprises a short cylindrical tube that is disposed over the front portion of the housing 73 and can freely rotate about the longitudinal axis of the housing 73. An actuator slot 82, extending circumferentially and perpendicular to the longitudinal axis of housing 73, is provided on the upper half of the housing 73. The backup manual actuator 74 is linked to the front portion of the core 72 with connecting rod or pin 76 through slot 82. The width of the slot 82 is chosen to guide but permit free movement of pin 76. The core 72 can thus be rotated about its longitudinal axis with respect to housing 73 of sub-system 61 by the rotation of the backup manual actuator about the same axis.

It will be understood that the proximal end of each pull/push member 11 and 12 is fastened to a corresponding one of the pull/push member length adjusters 158, 160 by screws 162, 164 respectively.

Rotation of core 72 about its longitudinal axis will pull one of the pull/push members 11 or 12, and compresses the other one, resulting in formation of curvature at the distal portion of the catheter 1.

The multi connector junction jack 69 and multi connector junction plug 67 serve as both the mechanical and electrical coupling between the sub-systems 60 and 61.

When sub-systems 60 is connected to sub-system 61, the left end of the drive shaft 66 is engaged with the right hand end of core 72. The motor can be energized and controlled for forward and reverse rotation by a switch 75 provided on the exterior of housing 73. As the motor 64 is activated, the drive shaft 66 will rotate the core 72 which results in formation of curvature at the distal portion of the catheter. Angular displacement sensor 79, disposed in the housing 61, is employed to provide predetermined limits for the angular rotation of core 72 as an indication of the radius of curvature at the distal portion of the catheter. The actuator or servomotor driven cardiac catheter handle 154 of FIG. 17 can also be controlled remotely via computer and/or tele-communication systems and thus has application for various other cardiac catheter procedures.

Figure 18:
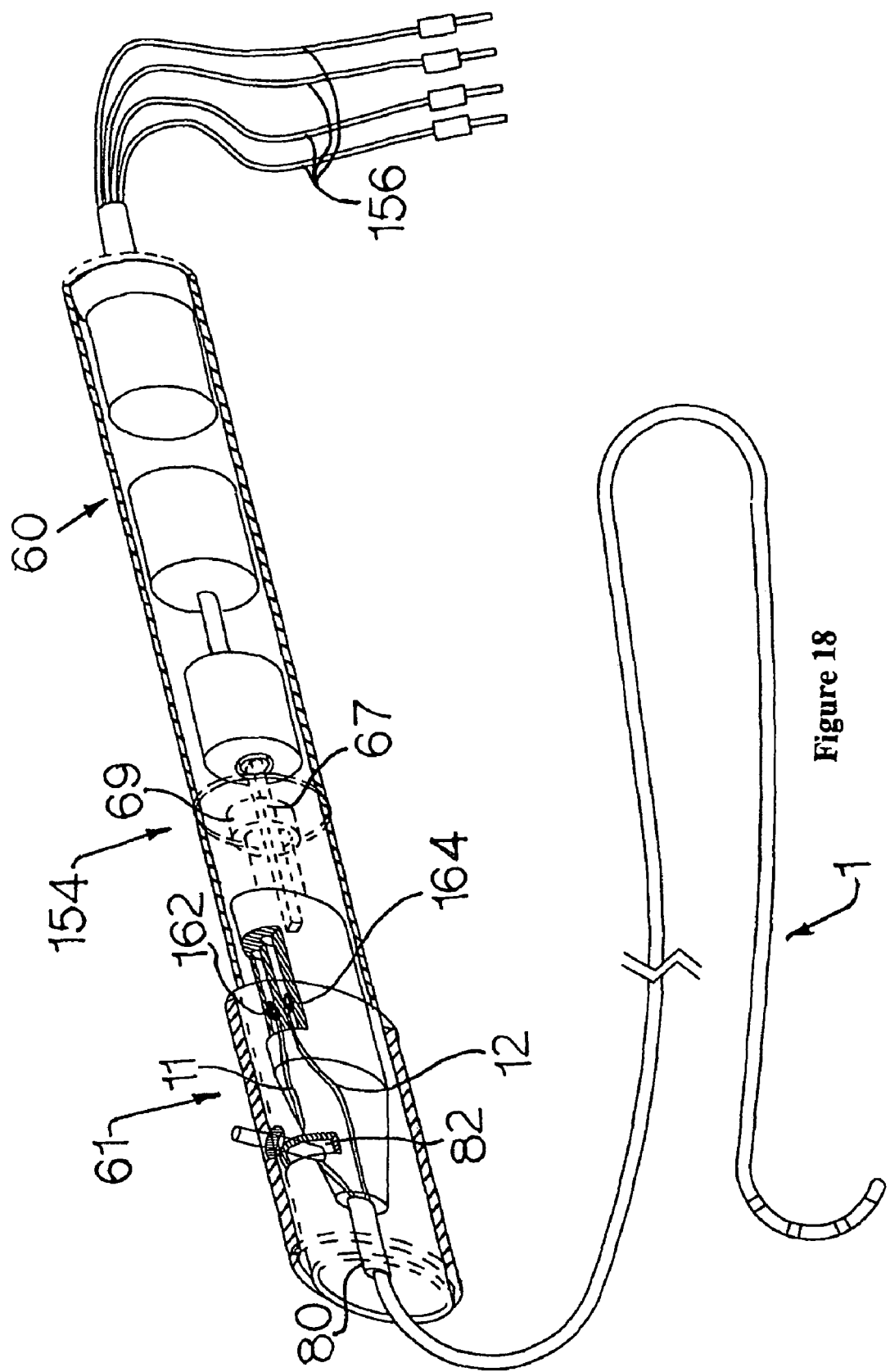
FIG. 18 Shows a perspective view of catheter handle of FIG. 17 with the two main segments attached together.

Referring to FIG. 18 the servomotor operated electromechanical catheter handle 154 is shown as a complete assembly with its two subassemblies 60 and 61 connected together with plug 67 engaging jack 69 as shown in dashed line.

Figure 19:
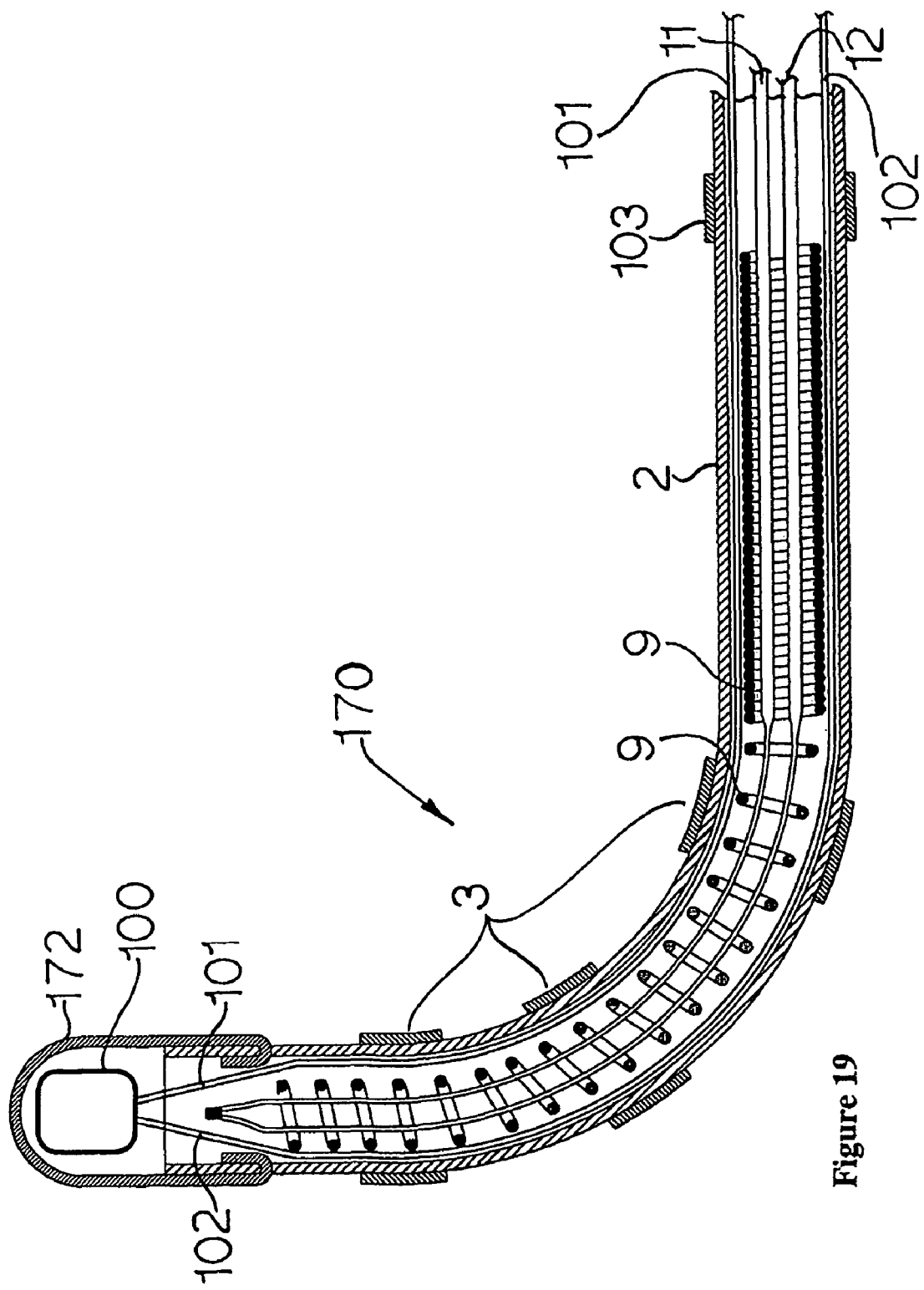
FIG. 19 Shows a sectional view of the ablation catheter with a heating element within its distal electrode.

Referring to FIG. 19 the distal portion of a further embodiment of the catheter of this invention indicated generally at 170 and is shown in the curved condition. The embodiment of FIG. 19 is configured such that it can be employed for cardiac ablation and intra-cardiac mapping procedures.

This embodiment indicated generally at 170 in FIG. 19 is a modified version of the catheter 1 presented in FIG. 1 of this invention. The modification is applied on the catheter distal tip electrode 5 of the FIG. 1 embodiment and is described as follows.

Referring to FIG. 19 an electrical heating element 100 is disposed within the distal tip cup-shaped electrode 172. The heating element 100 is energized by a battery disposed in the catheter handle 4 or by an external electrical power supply (not shown). The temperature of the distal electrode is controlled by adjusting the electrical current flow through the heating element 100. Electrical lead wires 101 and 102 are connected to the heating element 100 and extend from the heating element 100 within the interior of tubular body 2 to the proximal end and outwardly to the power supply and temperature control switch (not shown).

The embodiment 170 includes an additional annular reference electrode 103 on the catheter main exterior tube 2 for a uni-polar application of the catheter during intra-cardiac mapping procedures. In addition, the catheter 170 may include a blood-clot sensor or detector (not shown) and a temperature indicator (not shown) in the catheter handle 4. The purpose of blood clot sensor is to stop or reduce the delivery of electrical energy to the heating element during ablation procedures.

Referring to FIGS. 20a through 20d a further embodiment 180 of the catheter of the present invention is illustrated and has the feature that the blood contacting portions are disposable; and, thus, the embodiment 180 is particularly suitable for cardiac electrophysiology/ablation procedures. The embodiment 180 is a modified version of the catheter presented in FIG. 1 of this invention. The modification is applied in two parts. The first modification pertains to the shape of the distal tip electrode 176 and its connection to the main exterior tube 172 of the catheter which, along with a proximal end connector 181 having internal connector rings 188 comprises the blood contacting components or sub-assembly indicated generally at 166. The second modification involves the method of connecting the subassembly 166 of blood contacting components i.e. a main exterior tube 172, spaced electrodes 174 and distal electrode 176 to the non-blood contacting components indicated generally at 168 comprising an inner guide tube 178 and catheter handle indicated generally at 182.

Figures 20A, 20B:
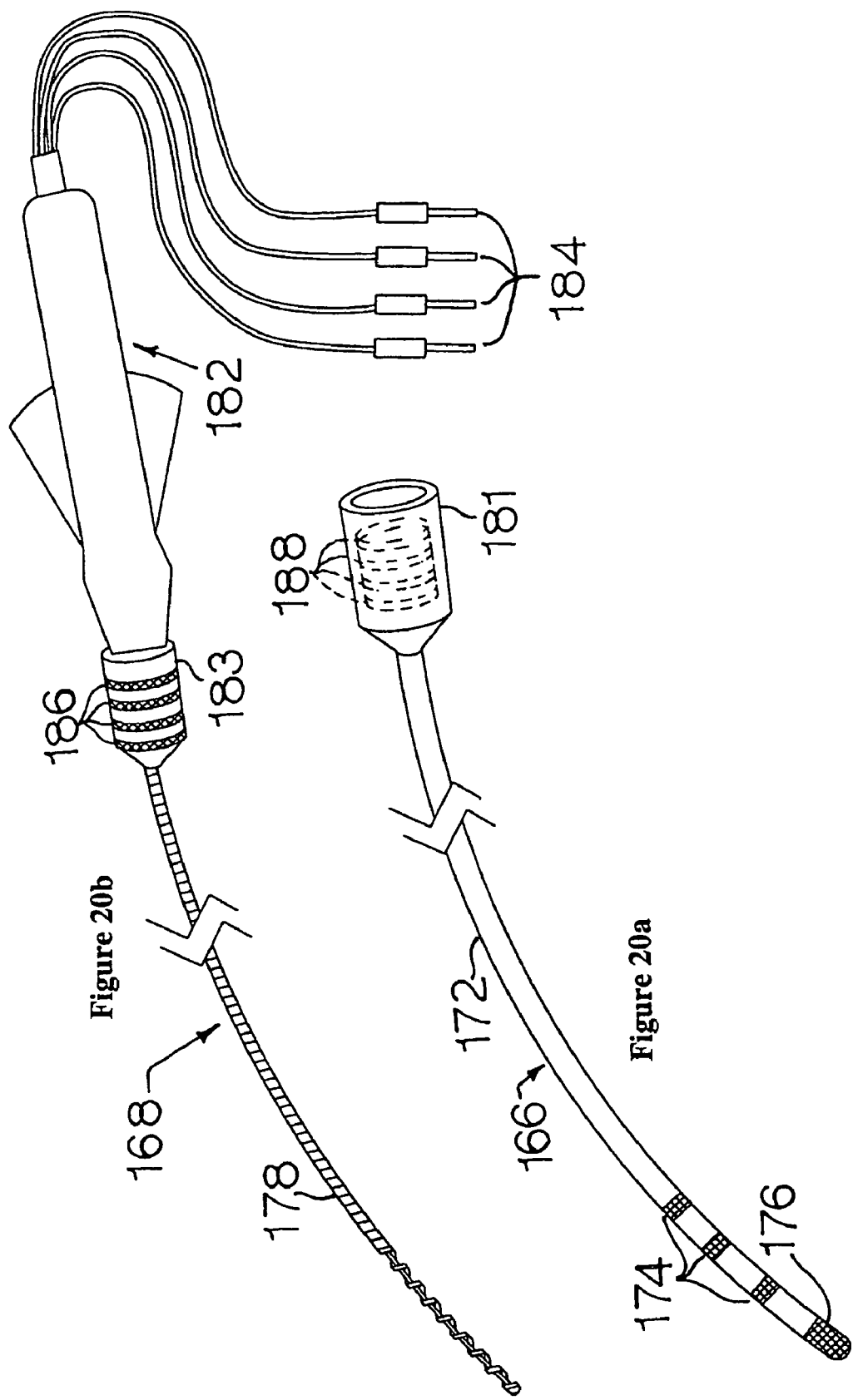
FIG. 20a Shows the blood contacting segment of the partially disposable catheter with a quick attachment/detachment plug.
FIG. 20b is a view of the non-blood contacting segments of the catheter with a quick attachment/detachment jack.
Figure 24:
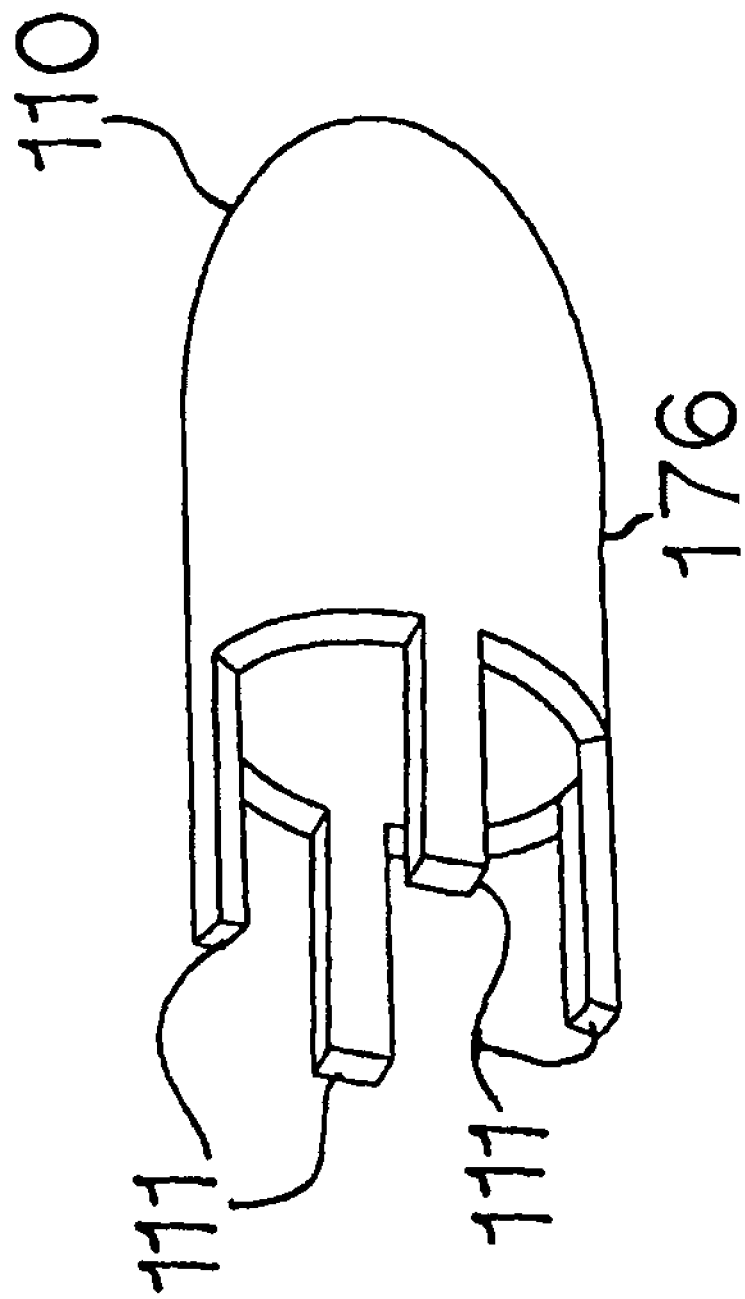
FIG. 24 Shows a perspective view of a cup-shaped distal electrode.

The first modification is illustrated in FIG. 20a. FIG. 24 shows the modified distal electrode 176 employed in the FIG. 20a embodiment as having a cup-shaped configuration. The distal electrode 176 is formed as a cylindrical shell with a hemispheric dome 110 on the closed end and a plurality, preferably four, of circumferentially spaced prongs 111 extend outwardly in an axial direction from the other open end of the cup-shaped distal electrode 176.

Figure 25:
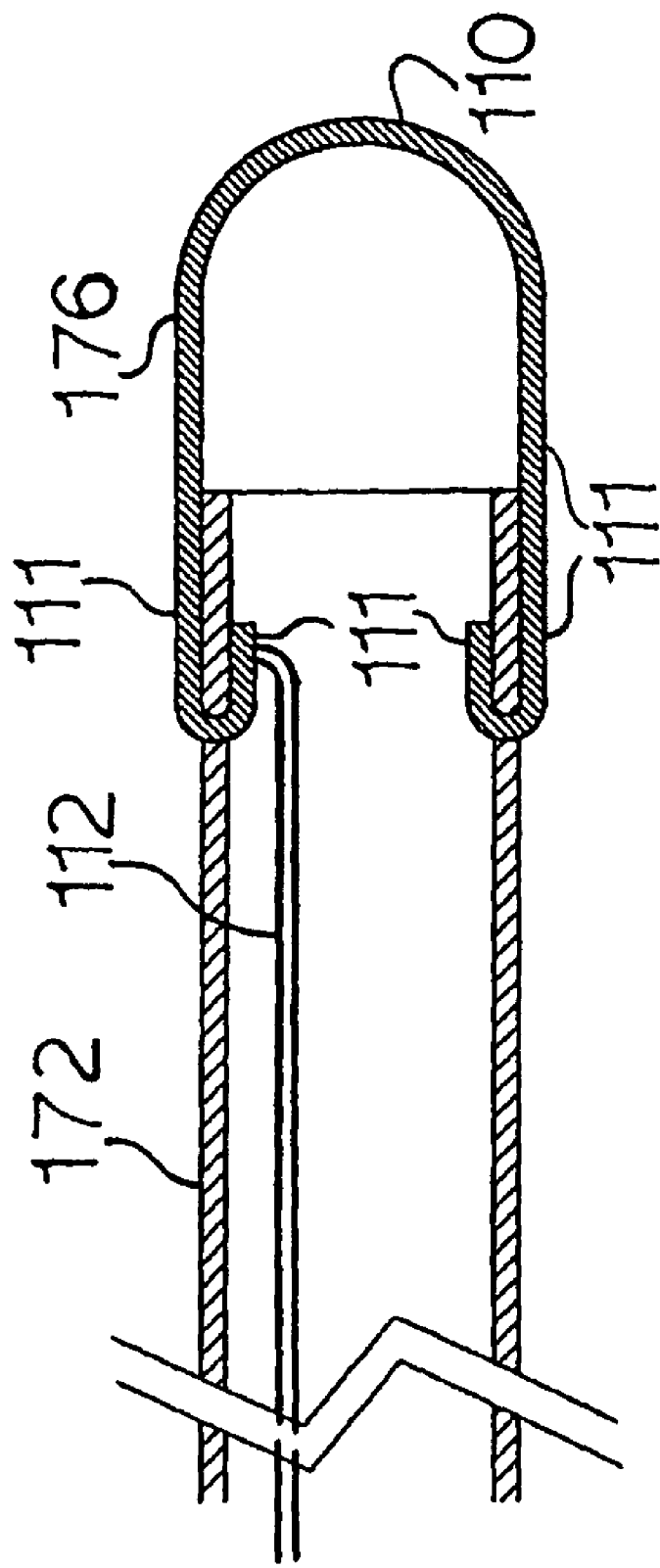
FIG. 25 Shows a sectional view of the distal portion of the catheter main body and its connection to the cup-shaped distal electrode.

Referring to FIG. 25 the cup-shaped electrode 176 is sleeved partially over the distal portion of the main exterior tube 172 of the catheter. The prongs 111 are bent inwardly perforating the wall of the main exterior tube 172, extending inwardly and again bent over the inner wall of the main exterior tube 172 to form a "stapled-type" connection between the cup-shaped distal electrode 176 and the main exterior tube 172. At least one wire 112 is wrapped around one of the prongs 111 and secured to the inner wall of the main exterior tube 172 to provide electrical connection to electrode 176 and also provides a redundant securement to tube 172.

Referring to FIGS. 20a-20d, the second modification for the disposable catheter 180 is described as follows. The two sub-assemblies, namely the blood contacting subassembly 166 and non-blood contacting sub-assembly 168 of catheter 180 of this invention are individually fabricated such that they can function independently as intended.

Referring to FIG. 20a, the first sub-assembly or blood contacting unit 166 of this embodiment 180 comprises of the main exterior tube 172 of the catheter, the spaced surface electrodes 174 and distal electrode 176, the electrical wires of the surface electrodes and the combined electric coupling and structural connector 181. All electrical wires of the catheter tip electrodes 174, 176 terminate to the coupling 181.

Referring to FIG. 20b the second non-blood contacting sub-assembly 168 of embodiment 180 is illustrated. Second sub-assembly 168 comprises the inner guide tube 178, a combination electrical connector and structural coupling 183, a catheter handle indicated generally at 182 and catheter electrical lead connector end plugs 184. The non blood contacting sub-assembly 168 can readily be coupled to the blood contacting subassembly 166; and, the two can be locked together by the couplings 181 and 183 which may be threaded or quick-lock type to form a assembly 180 that can function as a complete catheter.

Figure 20C:
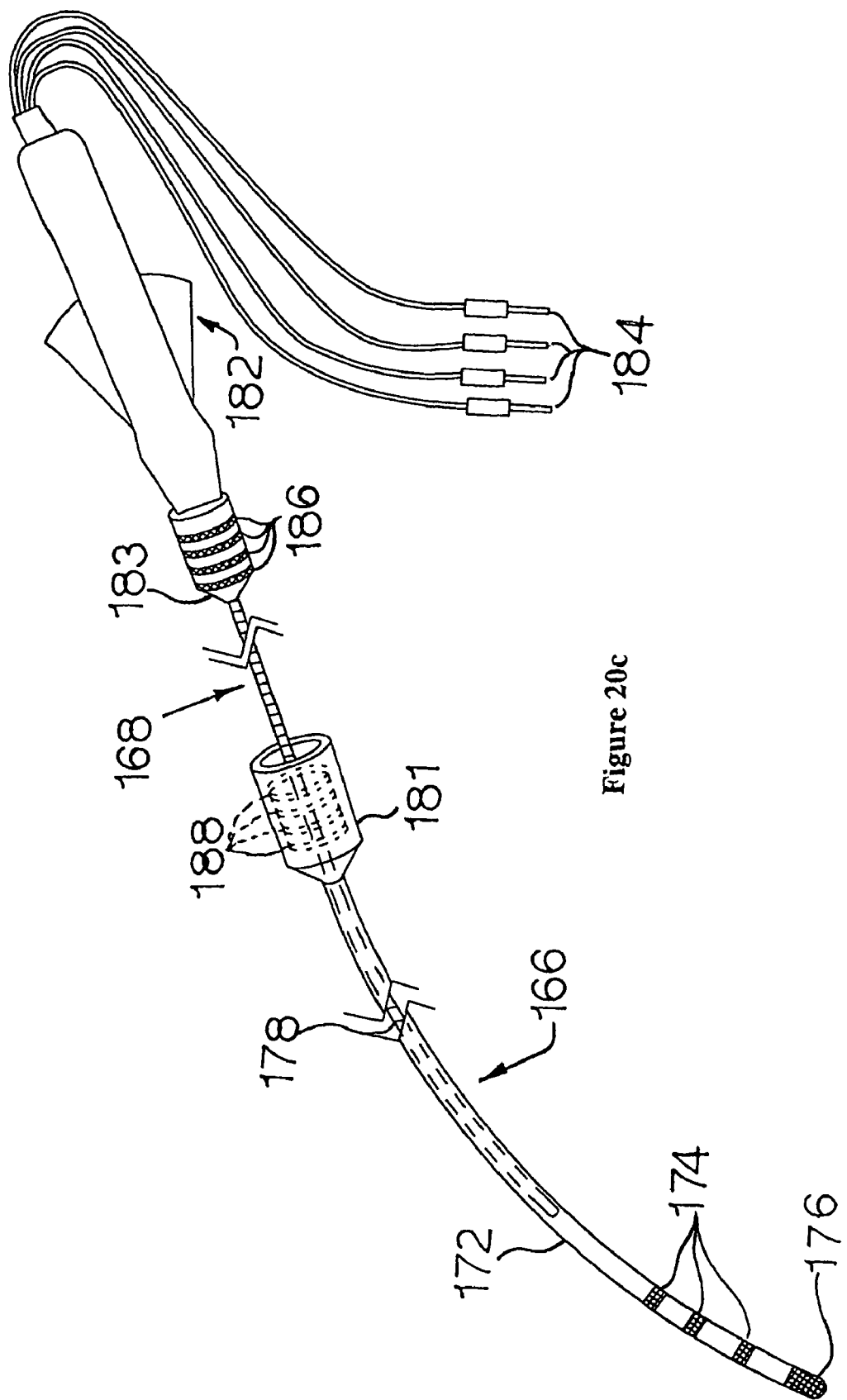
FIG. 20c Shows the process of attachment/detachment of the blood contacting and non-blood contacting segments of the partially disposable catheter.

Referring to FIG. 20c the coupling of the two sub-assemblies of the catheter of this invention is shown with guide inner tube 178 of subassembly 168 partially inserted into tubular casing 172 of sub-assembly 166. The coupling action of the two sub-assemblies 166, 168 can also be done during the cardiac electrophysiology/ablation procedures by the physician. This allows the physician to select from variety of second non-blood contacting actuator sub-assemblies 168 that offer different distal portion curvature configurations for the same blood contacting sub-assembly 166. In the embodiment 180, the disposable segment of the catheter comprises only the blood contacting sub-assembly 166 shown respectively in FIG. 20a.

Figure 20D:
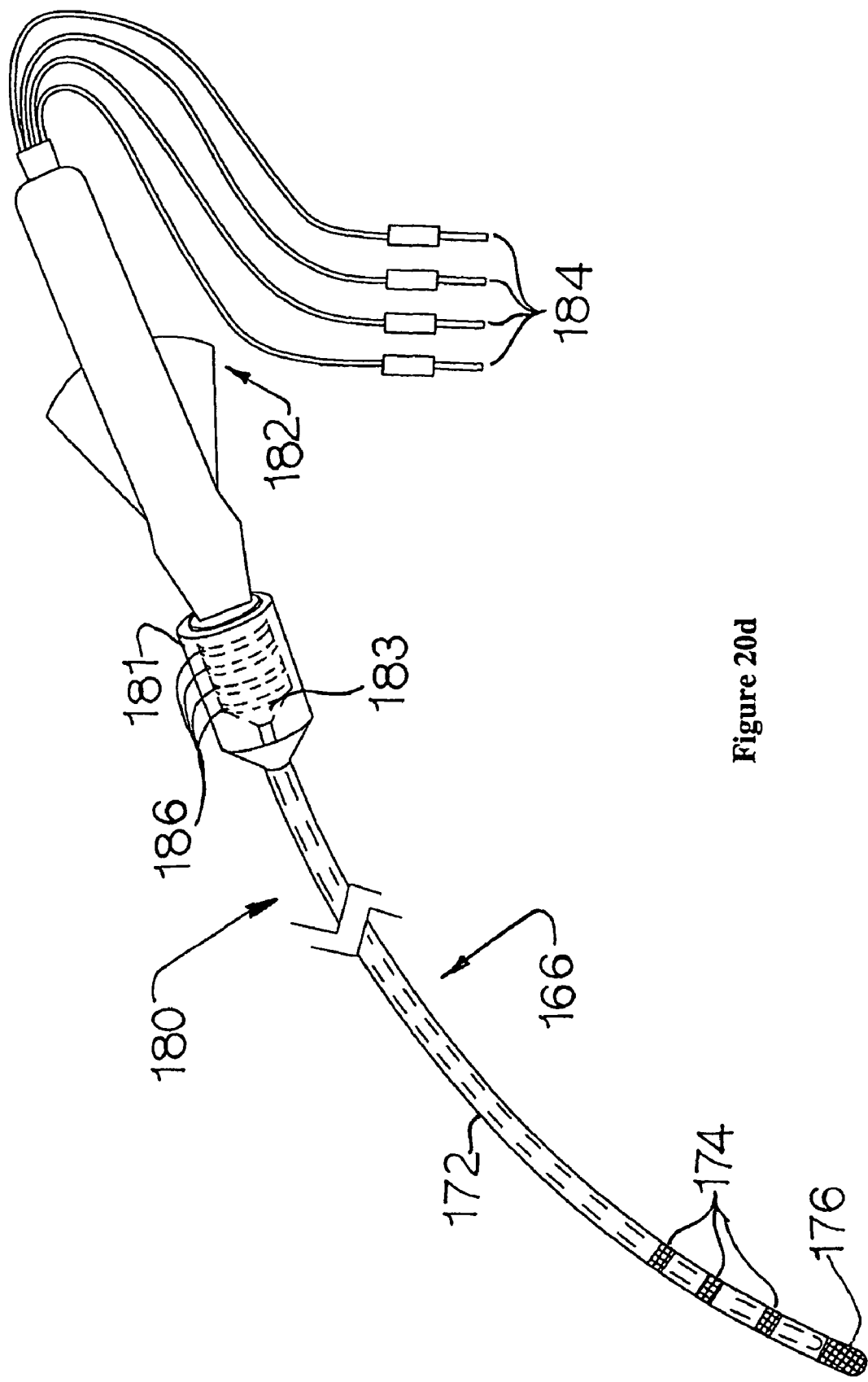
FIG. 20d Shows the segments of FIG. 20c fully assembled.

Referring to FIG. 20d, the catheter of embodiment 180 is fully assembled with connector 181 engaged with connector 183. It will be understood that the electrical lead from each of the electrodes 174, 176 is connected to one of the electrical terminal rings 186 on connector 183. Each of the rings 186 makes electrical contact with a correspondingly located terminal annular 188 provided in connector 181 of sub-assembly 166.

The catheter of this embodiment 180 can thus significantly reduce the price of cardiac catheters and thus an overall cost reduction of the cardiac electrophysiology and ablation procedures.

Figure 21:
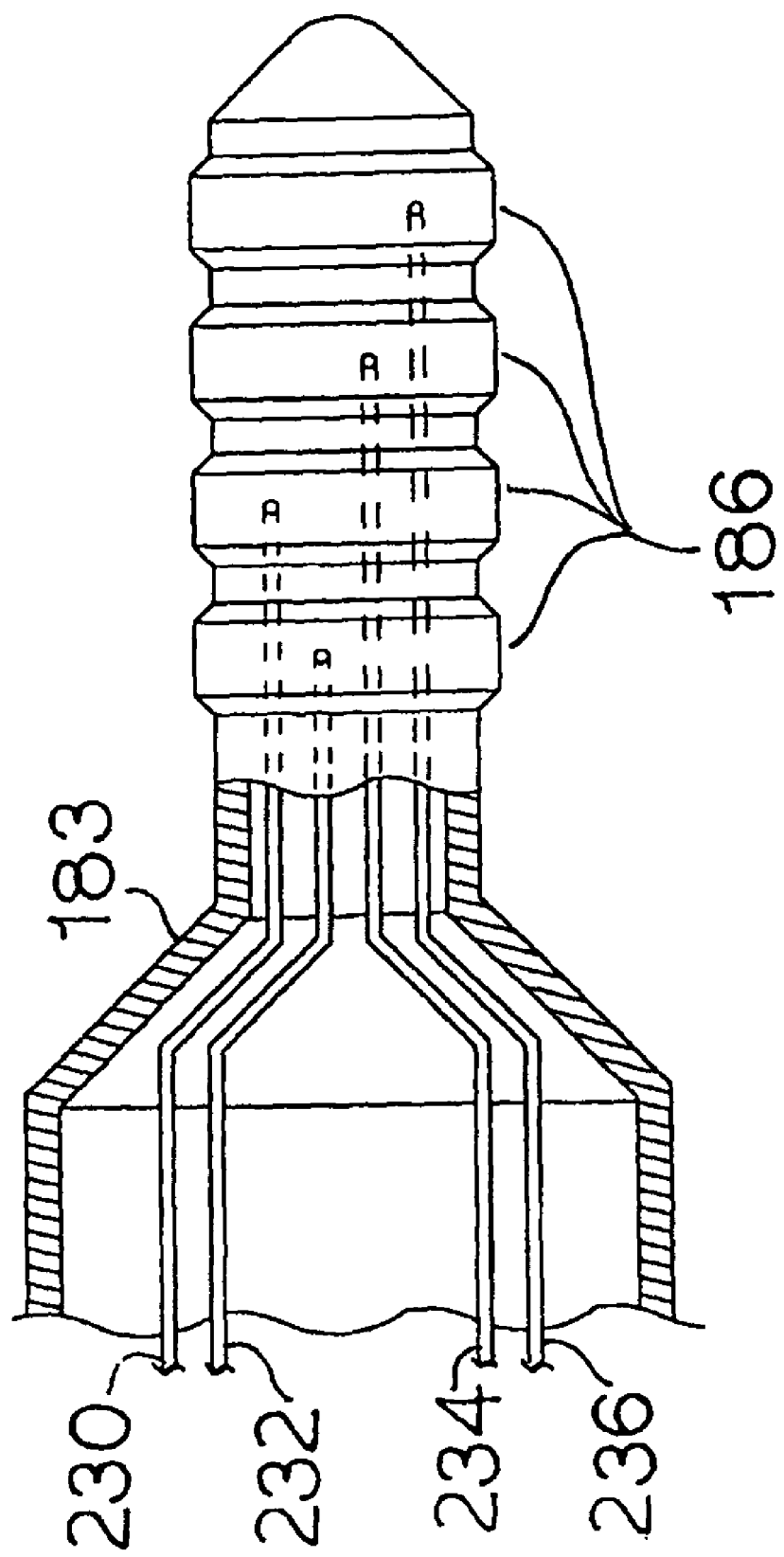
FIG. 21 is an enlarged view of the electrical connector of handle 182 of FIGS. 20b and 20c.

Referring to FIG. 21 the external electrical connector 186 of actuator handle sub-assembly 182 of FIGS. 20b, 20c, and 20d is shown where each of the electrical connector 186 has an end of one of the lead wires 230, 232, 234, 236, attached thereto. It will be understood tat each of the leads 230-236 has its opposite end connected to one of the connectors 184 externally of handle 182.

Figure 22:
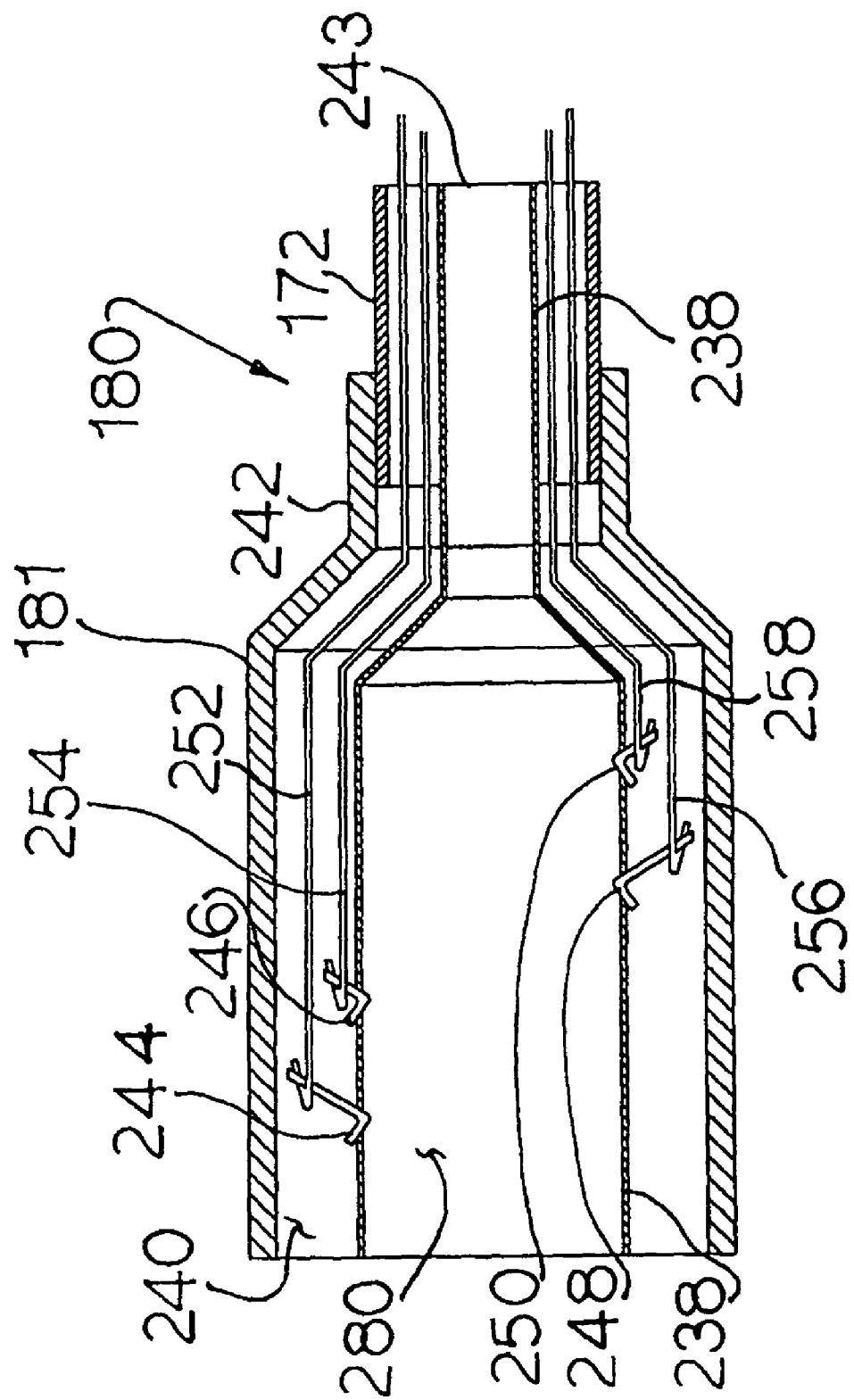
FIG. 22 is an enlarged view of the electrical connector of the disposable blood contacting portion 166 of FIGS. 20a, 20c, and 20d.

Referring to FIG. 22 the electrical connector 181 of disposable blood contacting subassembly 180 of FIGS. 20a, 20c, and 20d is shown enlarged with an internal tubular sheath or liner 238 defining an annular space 240 between liner 238 and the body of connector 181. The proximal end of the main exterior tube 172 is received and retained, as for example by weldment into a reduced diameter neck 242 formed on connector body 181, Liner 238 has a reduced diameter neck 243 which extends a predetermined distance into main exterior tube 172. A plurality of axially spaced electrical terminals 244, 246, 248, 250 are disposed on the inner periphery of liner 238 with each of its terminals 244-250 having portions thereof extending outwardly through the wall of liner 238 and into the annular space 240. A plurality of electrical leads 252, 254, 256, 258 is received in the annular space 240 and each has respectively one end thereof connected to one of the terminals 244-250. Each of the leads 252-258 extends through annular space between liner 238 and the inner periphery of main exterior tube 172 and continues to the distal portion of tube 172. It will be understood that each of the leads 252-258 is respectively connected to one of the electrodes 174, 176 on the blood contacting sub-assembly 166.

Figure 23:
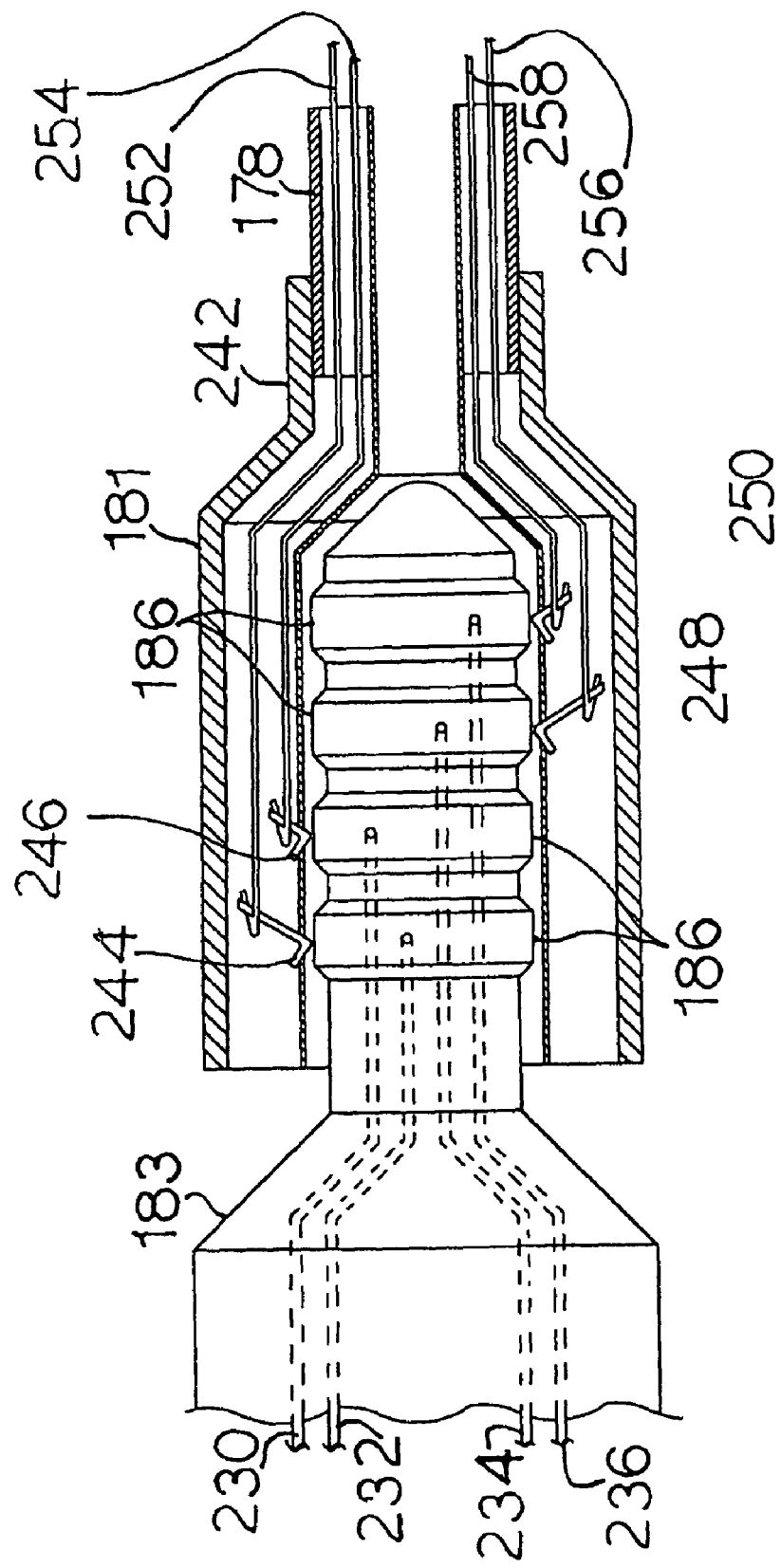
FIG. 23 is an enlarged view of the assembly of the connectors of FIGS. 21 and 22.

Referring to FIG. 23, connectors 181, 183 are shown assembled with the ring electrical connectors 186 of connector 183 each making contact with one of the connector terminals 244-250 for providing electrical continuity between electrical leads pairs 230 and 254, 232 and 252, 234 and 256, 236 and 258 thereby connecting each of the external connectors 184 with one of the electrodes 176 174 on the distal portion of the disposable blood contacting subassembly 166.

Figure 26:
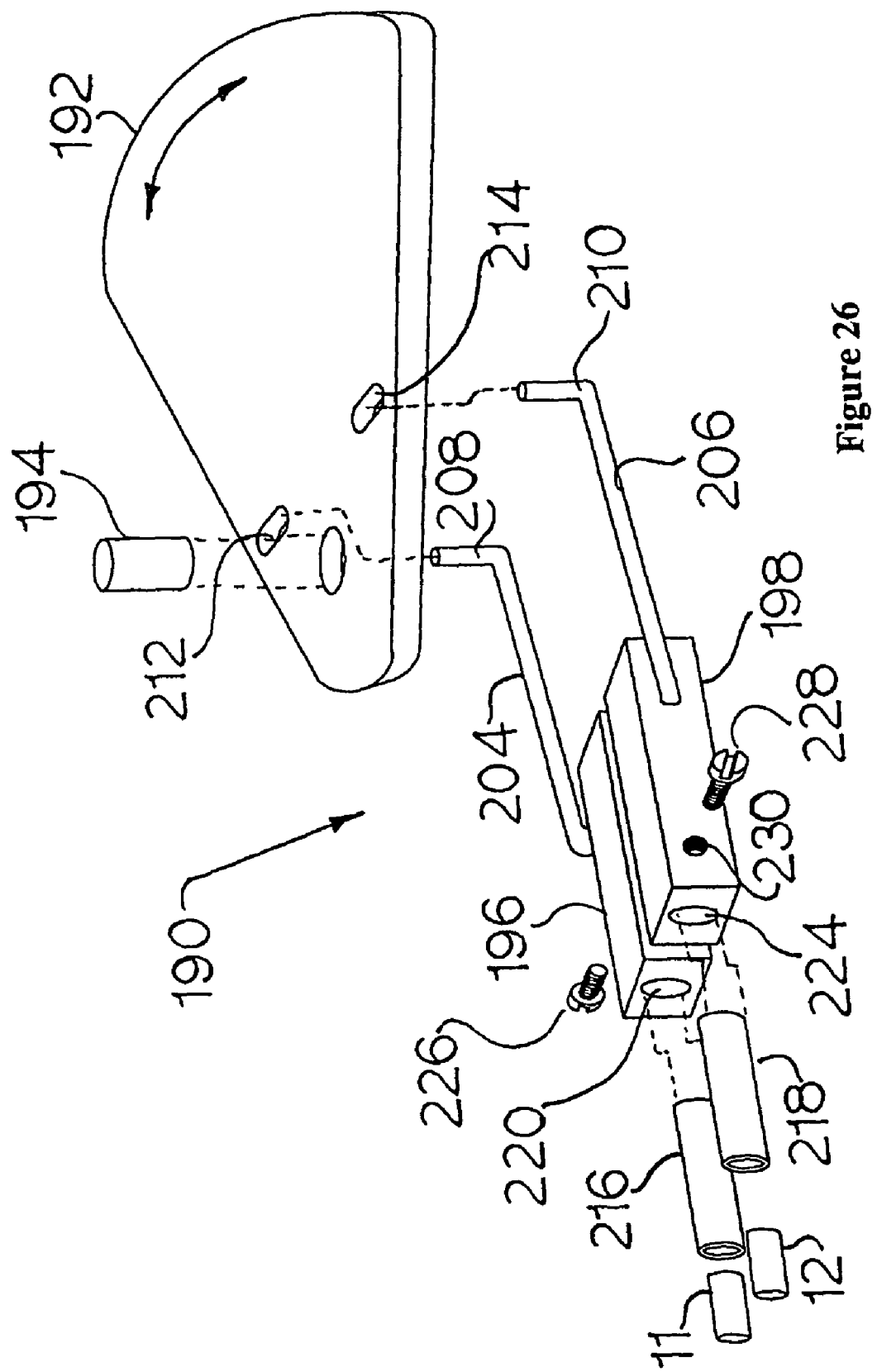
FIG. 26 is an exploded view of another embodiment of the catheter handle with a Scotch-Yoke mechanism for moving the tension/compression members.

Referring to FIG. 26 an alternative embodiment indicated generally at 190 of the catheter handle sub-assembly is shown in exploded view without the handle body with a Scotch-Yoke type pull/push mechanism for affecting formation of curvature at the distal portion of the catheter upon movement of the actuator member 192. The preferably delta shaped actuator 192 is disposed to pivot freely about pin 194 within the handle's body (not shown). It will be understood that member 192 may be disposed for pivoting in a handle slot in a manner similar to actuator member 18 of FIG. 1.

Figure 27:
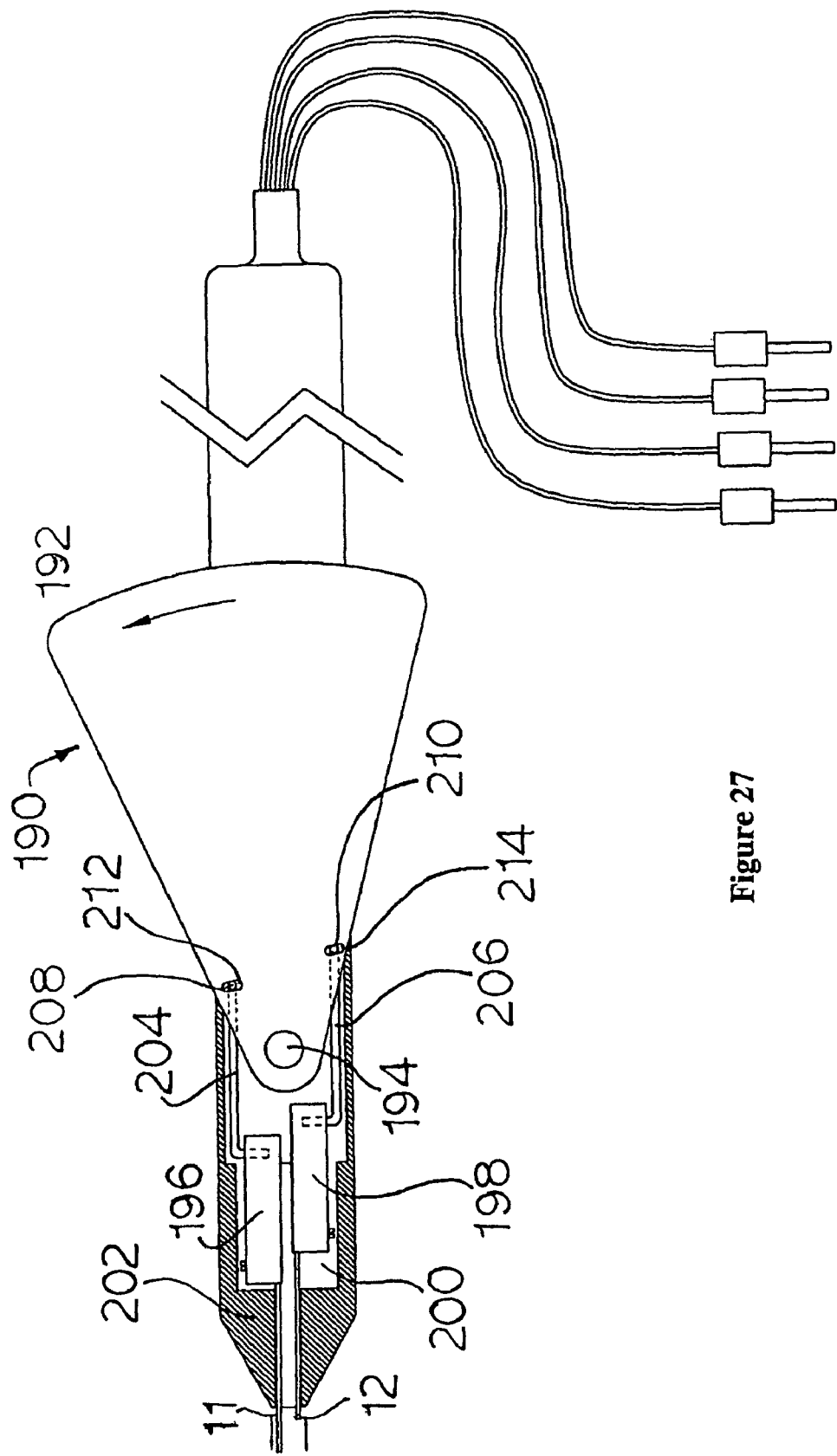
FIG. 27 is a section view of the assembled mechanism of FIG. 26.

Referring to FIGS. 26 and 27, the mechanism of handle 190 comprises two symmetrically coupled sliders 196 and 198 disposed for sliding movement in groove 200 formed in handle body 202 and with the single rotating actuator 192 as the driver thereof. The sliders 196 and 198 are linked to the delta-shaped actuator 192 by non-articulating pins or links 204 and 206.

Referring to FIG. 26 pins or links 204, 206 are formed generally at a right angle at one end, with the ends each received in a transverse bore provided in the side of sliders 196, 198 with links 204, 206 extending from sliders 196, 198 outwardly in the direction of sliding movement. The opposite or free ends of links 204, 206 are also formed at right angles in a common direction orthogonal to the links-receiving bores in the sliders 196, 198 and as denoted by reference numerals 208, 210. The links 204, 206 are thus non-articulatable in a center plane passing through both sliders 196, 198.

The actuator 192 has a pair of spaced slots 212, 214 elongated in a direction transverse to delta-shaped actuator 192. Link end 208 is received in slot 212; and, link end 210 is received in slot 214. It will be understood that user movement of the actuator 192 in the direction of the block arrows in FIG. 26 will cause relative movement of the link ends into slots 212, 214 and will result in pulling one and pushing the other of the sliders 196, 198 in groove 200 of body 202.

The proximal ends of tension/compression (pull/push) members 11 and 12 are individually received in a closely fitting tubular sleeve denoted respectively 216, 218 which are in turn received individually in a longitudinal bore denoted respectively 220, 224 provided in each of the sliders 196, 198. The sleeves 216, 218 may be secured to pull/push members 11, 12 respectively by weldment if desired, as, for example by soldering or brazing. The sleeves 216, 218 and the proximal ends of members 11, 12 are secured respectively in slider bores 220, 224 by engagement with set screws torqued into threaded cross holes provided in sliders 196, 198, one such cross hole is visible in FIG. 26 at 230.

Each of the two sliders 196 and 198 slides freely, in the straight groove 200 provided in the catheter handle 202.

Referring to FIG. 27 the actuator member is shown rotated counterclockwise from the position shown in FIG. 26, wherein actuator 192 has caused rectilinear displacements of the two sliders 196 and 198 in opposite directions. Slider 196 has been moved leftward pushing member 11; and slider 198 has been moved rightward pulling member 12. This movement of sliders 196, 198 results in formation of a curvature, in a counterclockwise direction, at the distal portion of the catheter. It will be understood that a clockwise curvature formation can be achieved at the distal portion of the catheter when the manual actuator 192 is rotated in a clockwise direction to the position shown in dashed outline in FIG. 27.

Figure 28:
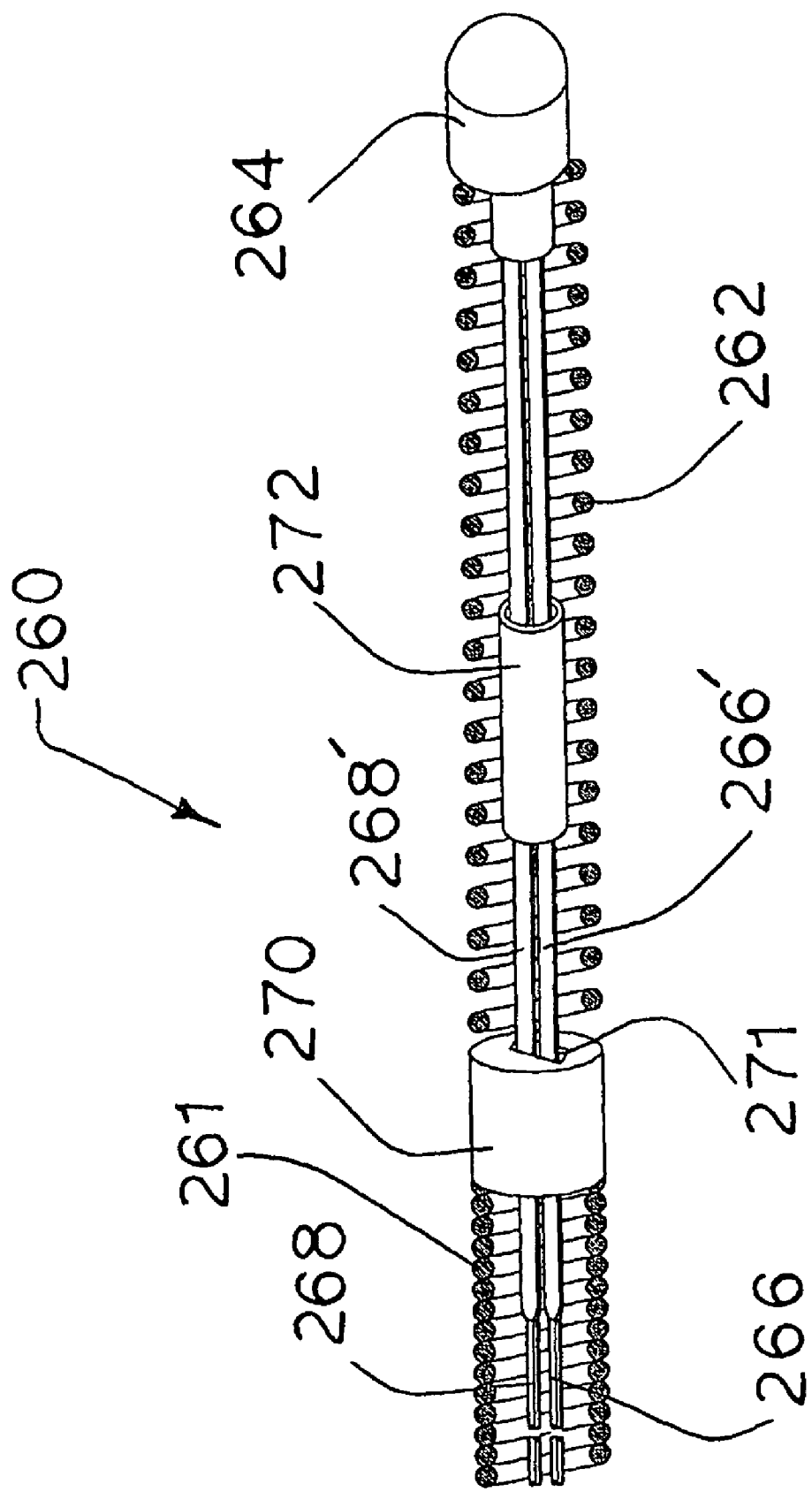
FIG. 28 is a cross-section similar to FIG. 2b of an alternate embodiment of the non-blood contacting inner guide tube and its associated components.
Figure 29:
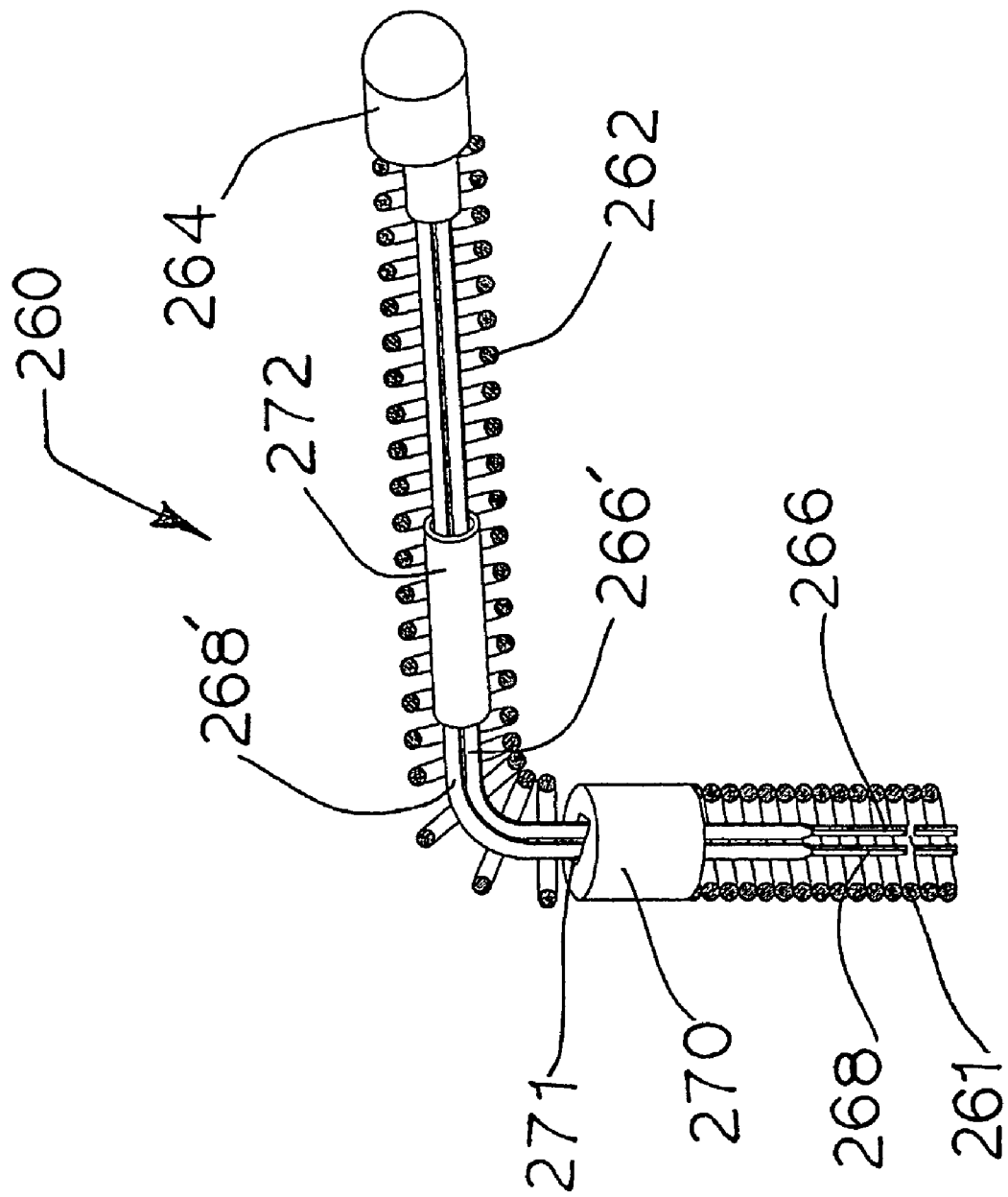
FIG. 29 is a view showing the embodiment of FIG. 28 in the deflected condition; and, FIG. 30 is a view showing the actuator handle assembly as grasped by the user's hand.

Referring to FIGS. 28 and 29, an alternative preferred embodiment of the non-blood contacting actuator 168 of FIG. 20b is shown generally at 260 with an inner guide tube 262 formed of helically wound wire similar to inner guide tube 178 of FIG. 20b. The distal end of inner guide tube 262 has a tip plug or member 264 attached securely thereto, such as by weldment. A pair of pull/push or tension/compression members 268, 266 are received in tube 260, with a portion of each denoted 266', 268' integrally flattened to a ribbon-like configuration, with the end of each ribbon secured to tip 264 as by weldment. A guide bushing 270 has a rectangular through bore 271 formed therein has the ribbons 266', 268' slidably received therein, with guide bushing 270 adjacent to the proximal end of ribbon-like portions 266', 268'. The guide bushing 270 is secured, such as by weldment, to the distal end of the inner guide tube 261 with contacting coils (closed windings).

An annular collar or sleeve member 272 is received over ribbon-like portions 266', 268' and serves as a kinematic junction of the ends of 266', 268'. The collar 272 is secured, such as by weldment, to both ribbons 266', 268' at a predetermined distance between the guide bushing 270 and tip plug 264. The actuator 260 is shown in relaxed or neutral condition in FIG. 28.

Referring to FIG. 29, tension has been applied to member 266 causing ribbon 266' to pull on collar 272 bending the 262 between guide bushing 270 and collar 272; however the portion of tube 262 between collar 272 and tip 264 remains straight or un-deflected.

Figure 9:
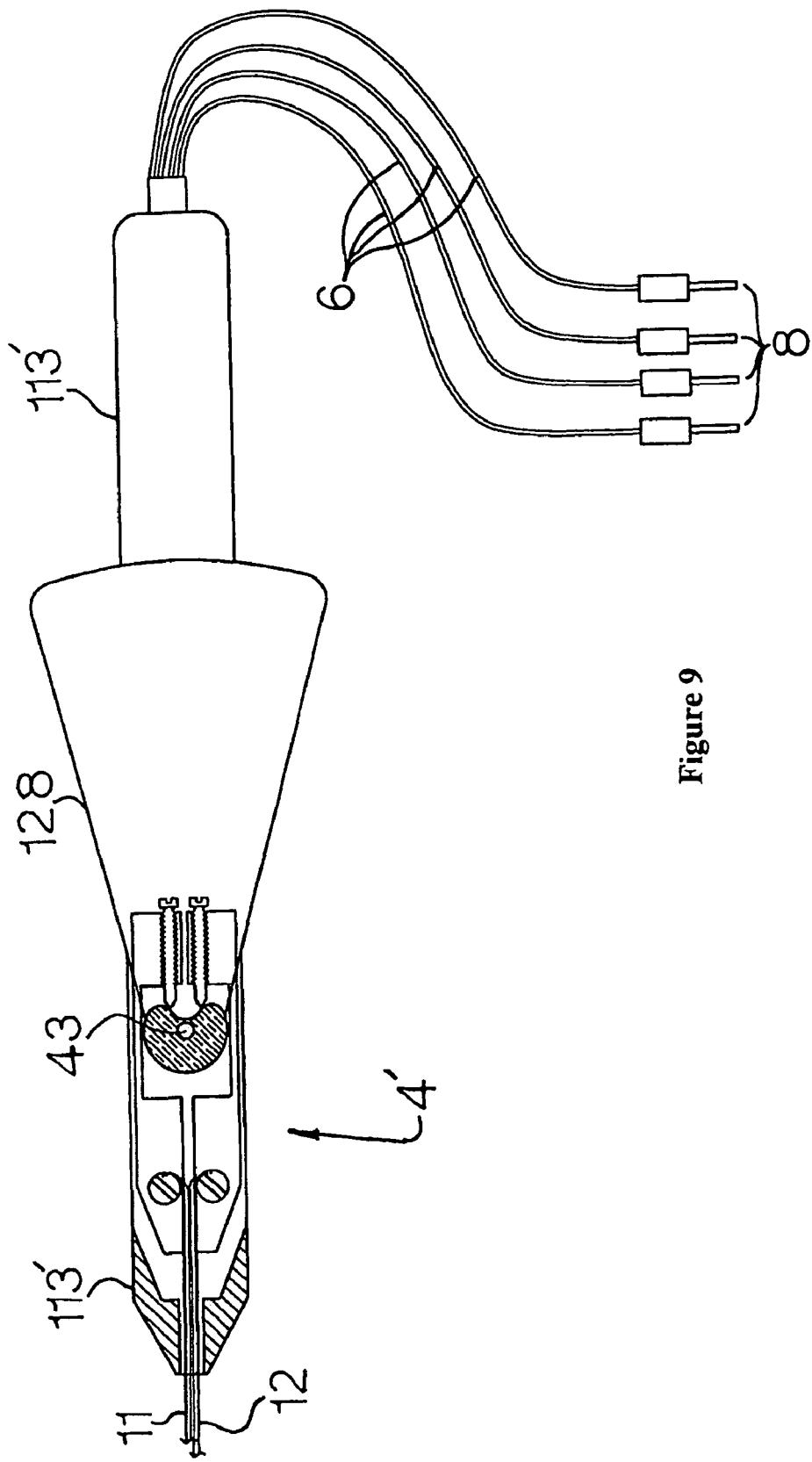
FIG. 9 Shows a plan sectional view of an alternative embodiment for the catheter handle with a cam-follower mechanism.

It will be understood that the inner guide tube 261 of FIG. 29 or 9 of FIG. 3a of the present invention is not loaded in compression when one of the members 266, 268 of FIG. 29 or 11, 12 of FIG. 3a is tensioned. Unlike the known catheters, the catheter of the present invention transmits the compression loading of the kinematic junction directly to the one of push/pull members 266, 268 of FIG. 29 that is not being tensioned by the manual actuator and does not use a separate compression strut member to transmit compression load to the inner guide tube as in the case of known catheters. It will be understood that in the embodiment of FIGS. 28 and 29 the kinematic junction comprises of the weldment of collar 272 to 266', 268'; and in the embodiment of FIG. 3 a the kinematic junction comprises the attachment of the pull/push or tension/compression members 11', 12' to the distal end of portion 10 of inner guide tube 9.

The present invention thus provides a low cost cardiac catheter which has a disposable blood-contacting segment removable from the actuator assembly which is re-useable. The actuator utilizes a pair of tension/compression members which are flattened integrally at the distal end region for improved deflection characteristics. The actuator handle is grasped in the user's hand and catheter distal region deflection in one direction is affected by movement of a handle actuator member in one direction by the user's thumb; and catheter deflection in the opposite direction is affected by movement of the handle actuator member in the opposite direction by the other finger(s) of the same hand.

Figure 30:
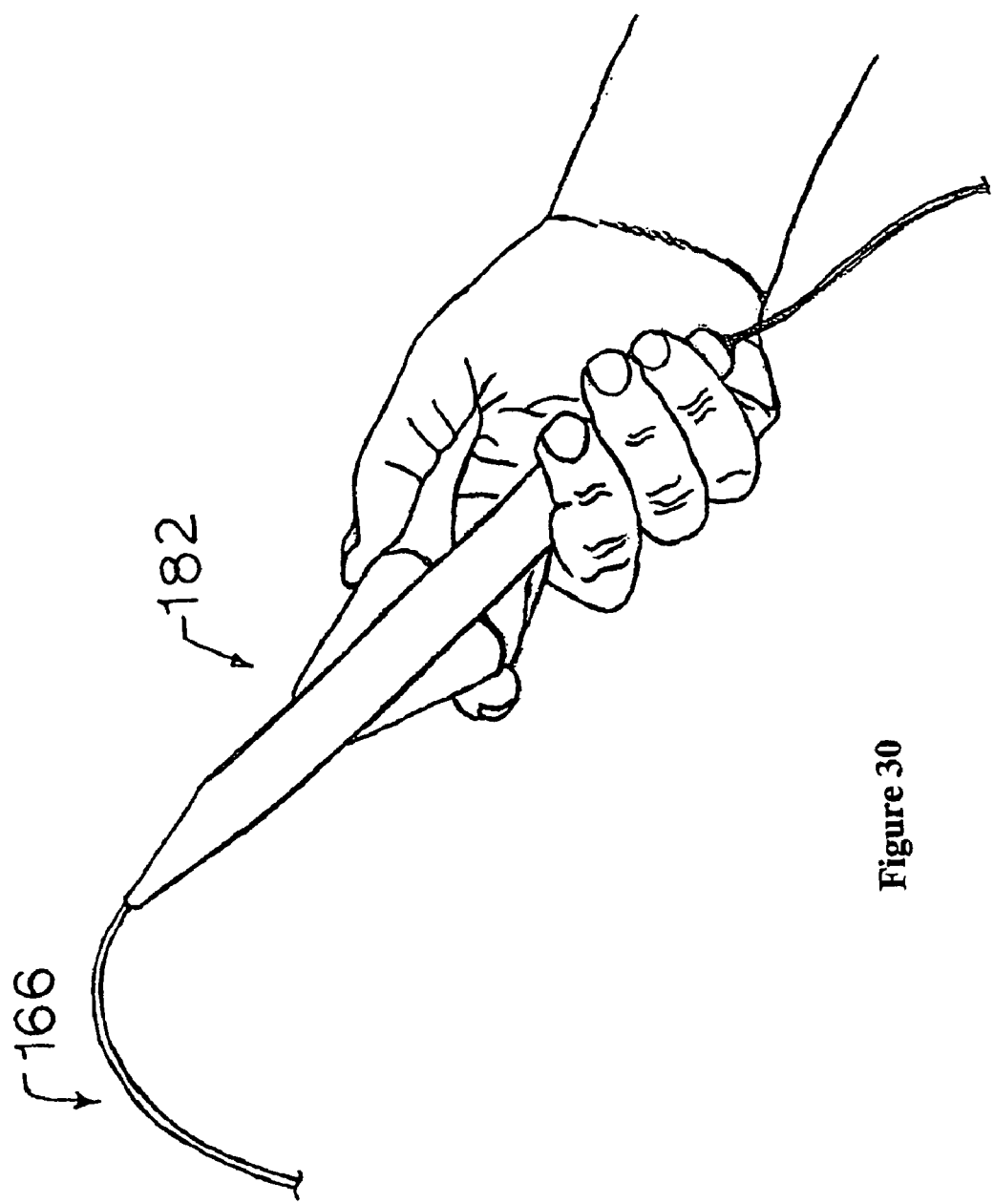
Figure 35:
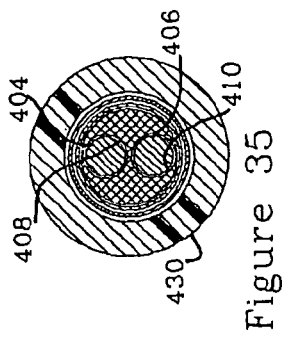
FIG. 35 is a section view taken along section indicating lines 35-35 of FIG. 33.

FIG. 30 is a view showing the actuator handle assembly as grasped by the user's hand.

Referring to FIGS. 31 and 32, another embodiment of the catheter of thee invention is indicated generally at 300 and has a solid distal electrode that in the present practice of the invention has been formed satisfactorily from platinum material and is denoted by reference numeral 302. The electrode 302 has the distal ends of a pair of tension/compression members 304, 306 secured therein as for example by weldment which in the present practice of the invention comprises a brazed joint 308. It will be understood that the distal portions of the tension/compression members 304, 306 have a generally flattened rectangular transverse cross-sections as illustrated in FIG. 32.

A spacer means 310 is disposed between the flattened ends of tension/compression members 304, 306 in the present practice of the invention. The spacer means 310 comprises a wave-shaped flat spring having a generally rectangular transverse cross-section with an end thereof secured between the tension/compression members 304, 306 in a kinematic junction indicated generally at 312. The kinematic junction 312 is formed by a sleeve 314 which in the present practice of the invention is formed of stainless steel tubing received over the tension/compression members at the kinematic junction having the end of the wave-shaped spring 310 and is secured and formed by weldment which in the present practice of the invention comprises brazing as denoted by reference numeral 316. It will be understood that the spacer 310 serves only to maintain the transverse or lateral spacing of the tension/compression members 304,306 on the side of kinematic junction 312 away from the distal electrode 302. It will be understood that except for the end of spacer 310 which is brazed into sleeve 314, the wave-shaped flat spring 310 is otherwise free-floating between the tension/compression members 304, 306.

It will be understood that the tension/compression members' transition to a round or wire-like configuration is denoted by reference numerals 304' 306' in a manner similar to the embodiment of FIGS. 2b and 3a of the present invention. In the embodiment of FIGS. 31 and 32, a thin wall plastic tubing 318 is received over the distal flattened portions of the tension/compression members 304, 306 and the plastic tube is received over, in closely fitting engagement, an annular sleeve or collar 320 secured to the weldment or brazed joint of the distal electrode. In the present practice of the invention, the collar 320 is formed of stainless steel material. The plastic tube 318 extends over the round cross-section portions 304', 306' of the tension/compression members; and, the tube 318 also extends over the distal end of an inner guide tube 322 which in the present practice of the invention comprises a closed coil stacked helical spring member.

A thin wall preferably stainless steel tubular member 324 is received over the tension/compression members 304', 306' and the tube 324 has one end thereof crimped to a flattened cross-section as denoted by reference numeral 326 and the member 324 serves to constrain the tension/compression members from twisting or rotation with respect to the outer casings 325 and 330 during flexing of distal portion of the catheter. An outer blood-contacting casing comprising a tubular flexible plastic member 325 has the distal end thereof is attached to a reduced diameter portion distal electrode 302 and extends over the tube 318 and has the opposite end thereof received over a thin-wall short annular sleeve member 328 which serves to join the outer casing member 325 with the outer casing 330 which is re-enforced with braided material as denoted by reference numeral 332. With reference to FIG. 31, a plurality of annular electrodes are received over the outer periphery of the casing member 325 and are disposed in spaced arrangement therealong with each of the electrodes having an electrical wire lead member connected thereto as denoted by reference numeral 334,336 for the electrodes and 338,340 for the wire leads in FIG. 31.

It will be understood that the catheter 300 is intended to be operated by the handle mechanism illustrated in FIG. 1 wherein the slider members are connected to the tension/compression members 304, 306 such that movement of the actuator causes one slider to tension one of the members 304, 306 and the other of the members is placed in compression; and, reversed movement of the actuator wherein the handle causes the other of the tension/compression members to be tensioned and the one to be placed in compression.

Referring to FIGS. 33 through 37, another embodiment of the electrophysiology/ablation catheter of the present invention is indicated generally at 400 and has a construction generally identical to tat of the catheter 300 of FIG. 31 with the exception that the inner guide tube 302 is formed of plastic material and has two generally circular longitudinally extending lumens 404, 406 formed thereto to which are received the tension/compression members 408, 410.

Figure 37:
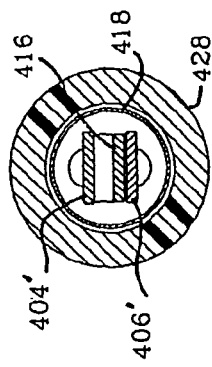
FIG. 37 is a section view taken along section indicating lines 37-37 of FIG. 33.
Figure 34:
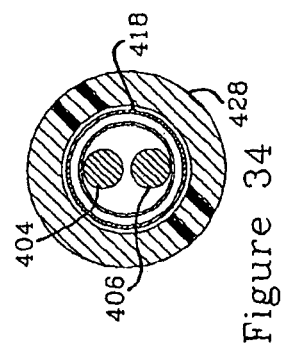
FIG. 34 is a section view taken along section indicating lines 34-34 of FIG. 33.
Figure 36:
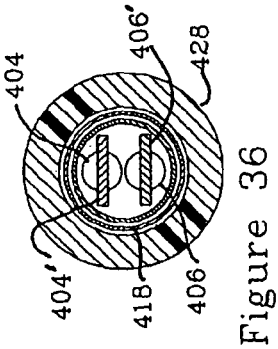
FIG. 36 is a section view taken along section indicating lines 36-36 of FIG. 33.

It will be understood that in the embodiment 400, a tension/compression members 404, 406 have flattened distal portions 404' and 406' as illustrated in detain in FIGS. 36 and 37; and, the embodiment 400 also employs the spacer means comprising a wave-shaped flat spring 416 with one end thereof secured in a kinematic junction 426 in a manner identical to that of embodiment 300 of FIG. 31.

It will be understood that in the embodiment 400, the inner guide tube is received in the end of the thin wall plastic tube 418 which corresponds to the tube 318 in the embodiment of FIG. 31.

Figure 39:
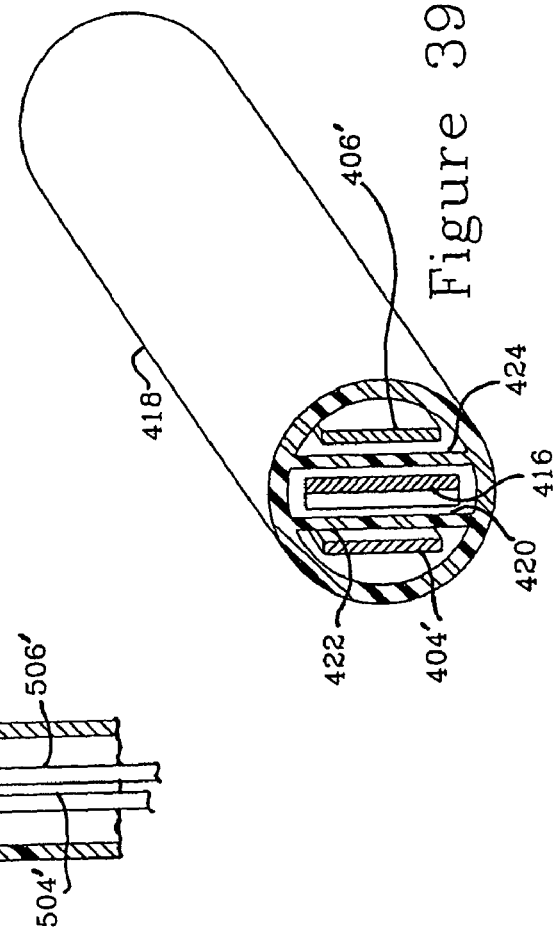
FIG. 39 is an enlarged view of the distal guide tube of the embodiment of FIGS. 33 and 38.
Figure 58:
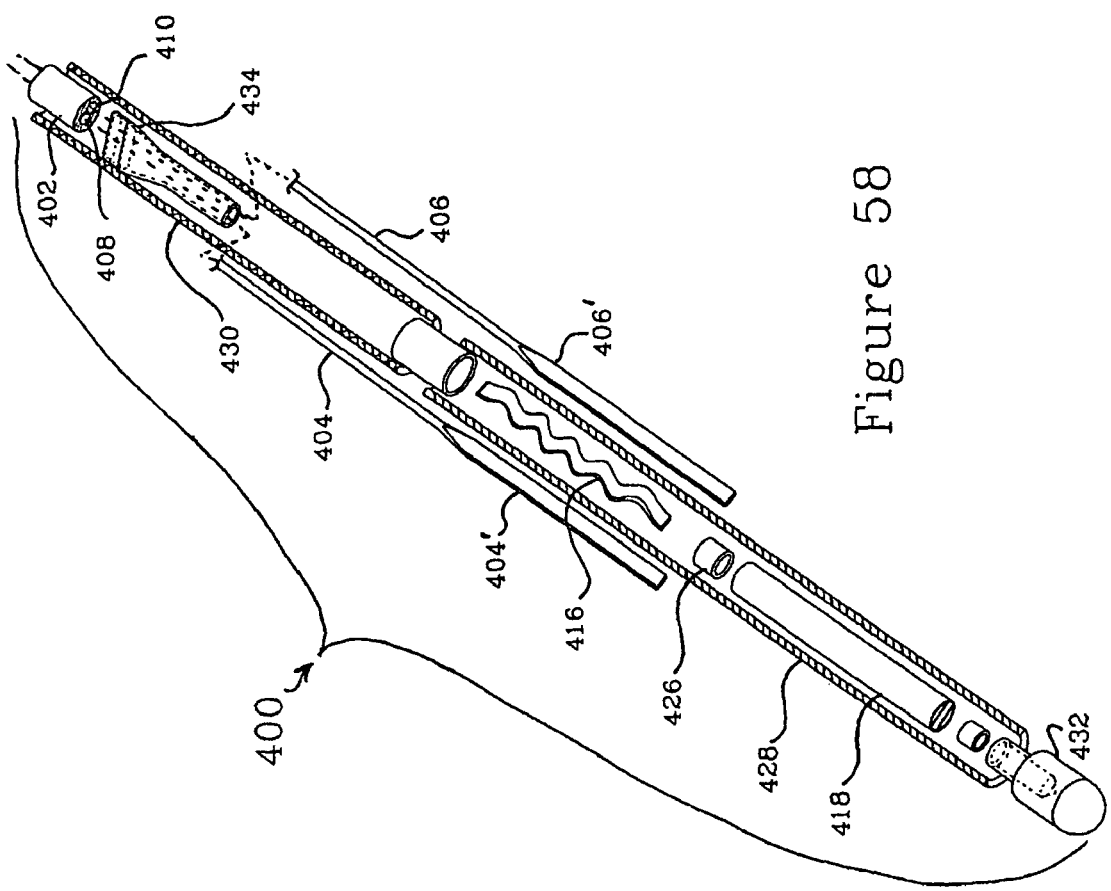
FIG. 58 is an exploded view of the embodiment of FIG. 33.

Referring to FIGS. 39 and 58, the embodiment 400 of the present invention is illustrated in exploded view in the preferred form wherein the flexible plastic tube 418 has three (3) lumens formed therethrough with wave-shaped flat spring spacer 416 received through the central lumen and each of the tension/compression members' flattened portions 404', 406' received through a lumen disposed respectively on opposite sides of the central lumen.

Referring to FIG. 39, the central lumen is denoted by reference numeral 420 and the side lumens are denoted by reference numerals 422 and 424. In the embodiment 400, the annular tube member forming the kinematic junction is denoted by reference numeral 426; and, the outer casing portion having the electrodes thereon is denoted by reference numeral 428 and the braided portion of the outer casing is denoted by reference numeral 430 and the distal electrode is denoted by reference numeral 432.

In the embodiment 400, the flattened tube portion denoted by reference numeral 434 is optional in as much as the construction of the inner guide tube 402 is operative to prevent twisting of the tension/compression members with respect to the outer casings 428 and 430.

Figure 33:
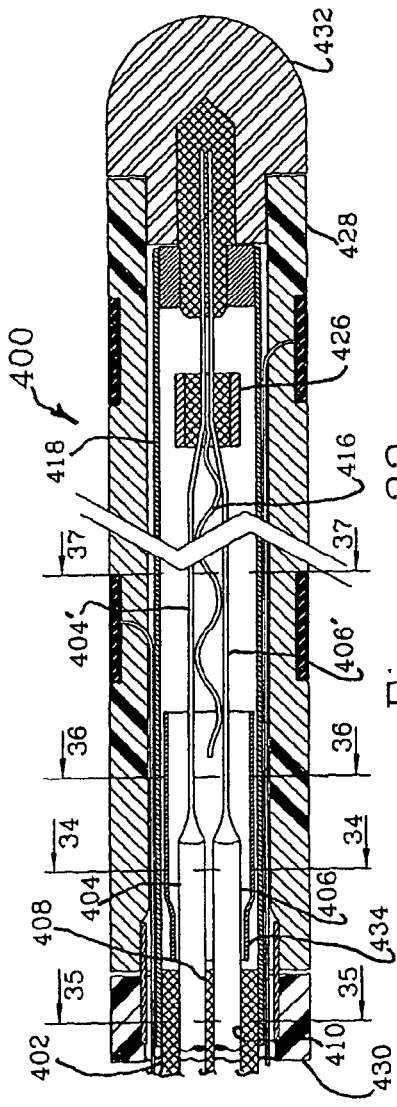
FIG. 33 is a longitudinal section view similar to FIG. 31 of an alternate embodiment of the invention of FIG. 31.
Figure 38:
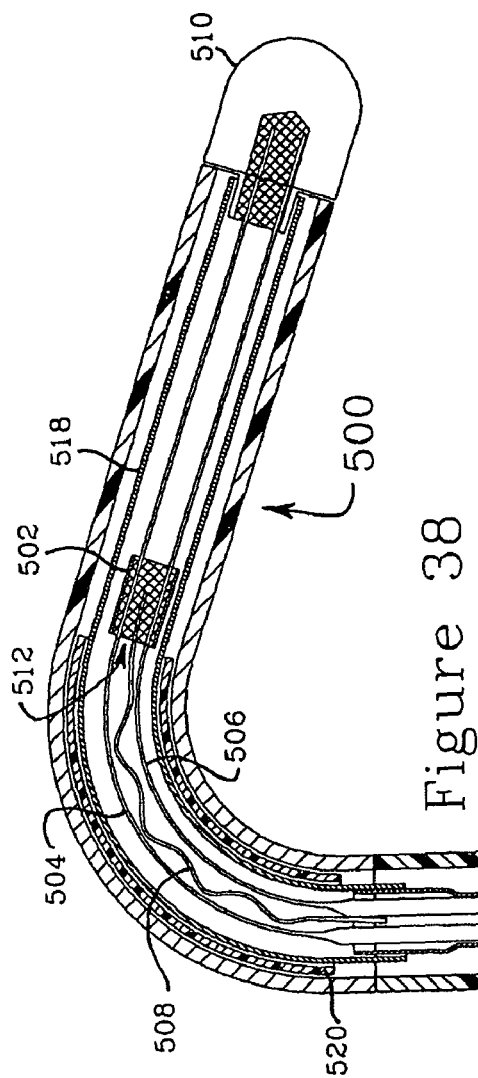
FIG. 38 is a longitudinal section view of the catheter of FIG. 33 in a modified embodiment with the distal portion thereof undeformed during curvature.

Referring to FIG. 38, another embodiment of the catheter of FIG. 33 is illustrated in longitudinal cross-section in its distal portion and denoted generally at 500. The catheter 500 is identical to the catheter 400 of FIG. 33 with the exception that sleeve or annular member 502 forming the kinematic junction of the ends 504, 506 of the tension/compression members 505', 506' and the end of the wave-shaped flat spring spacer 508 is spaced a distance further from the distal electrode 510.

The kinematic junction 512 is formed by brazing in distal ends of the tension/compression members 504, 506 and the distal end of the wave shaped flat spring spacer 508 in the annular member 502. By virtue of the distance between the distal electrode 510, and the kinematic junction 512 a region is created, between the electrode 510 and kinematic junction 512, which remains un-deformed during lateral deflection of the catheter by operation of the actuator for pulling and pushing on the tension/compression members 504' and 506'. In the embodiment 500, an additional flexible tube is inserted over the flexible tube 518 (which corresponds to the tube 418) and the additional tube denoted by reference numeral 520 which provides additional stiffness to the region of the catheter between kinematic junction 512 and the end of the tube 518 remote from electrode 510.

Figure 40:
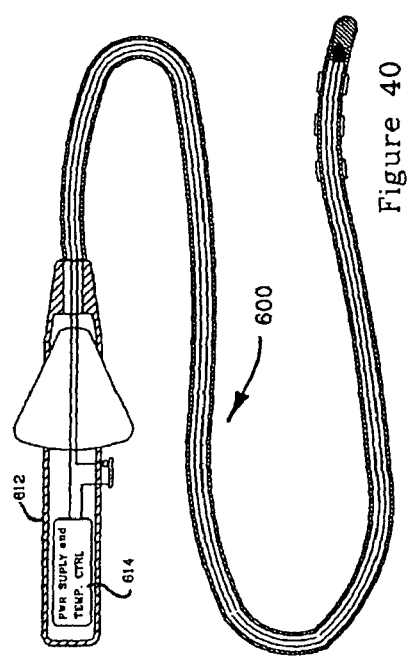
FIG. 40 is a longitudinal section of an ablation catheter embodying the present invention and having a self contained power source and temperature control in the handle.
Figure 41:
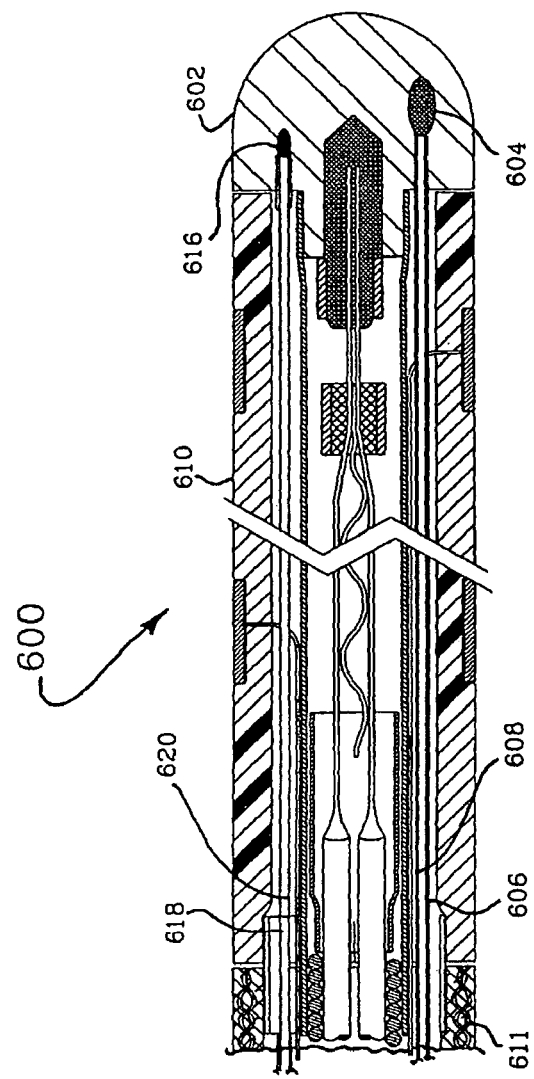
FIG. 41 is an enlarged detail section view of the distal end of the ablation catheter of FIG. 40.

Referring to FIGS. 40 and 41, another embodiment of the invention is indicated generally at 600; and, the distal portion of the catheter 600 is identical to the embodiment 300, 400 as described hereinabove except the distal electrode of the catheter 600, denoted by reference numeral 602, has embedded therein a heating element 604 to enable the catheter to be employed as an ablation catheter. It will be understood that the heating element 604 has a pair of electrical power leads 606, 608 attached thereto and which extend within the outer casing 610 to the proximal end of the catheter and into the handle 612 for connection to a power supply and temperature control module provided therein and denoted by reference numeral 614 in FIG. 40.

The embodiment 600 of FIG. 41 also includes a temperature sensor 616 embedded in the distal electrode 602, which is the present practice of the invention may be a solid state junction device which has leads 618, 620 extending within the casing 610 to the proximal end of the catheter. The sensor 616 is intended for use in remote monitoring of the temperature of the distal electrode 602 during ablation procedures.

Figure 42:
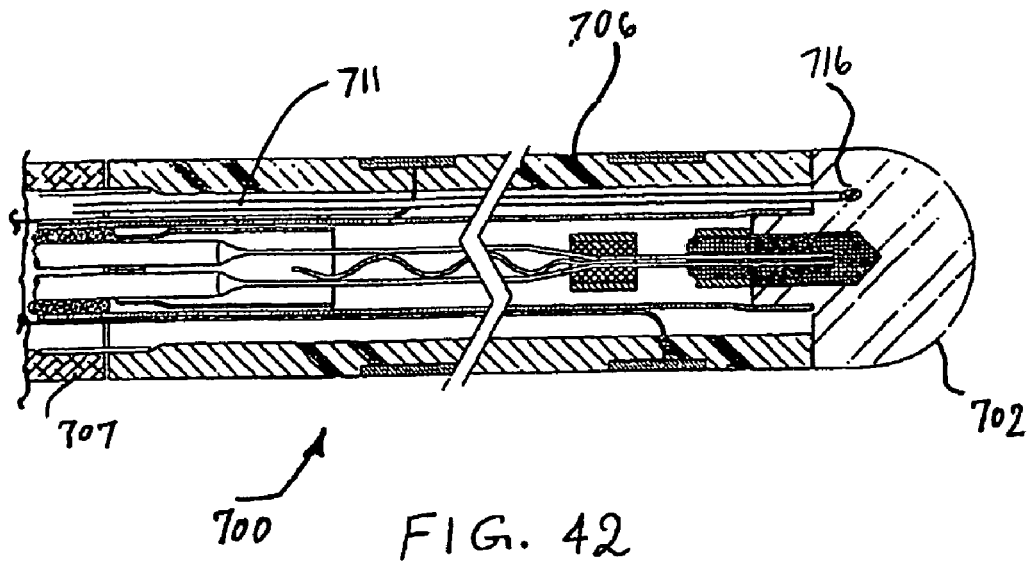
FIG. 42 is a view similar to FIG. 40 showing an alternate embodiment of the distal end of the ablation catheter of FIG. 40.
Figure 43:
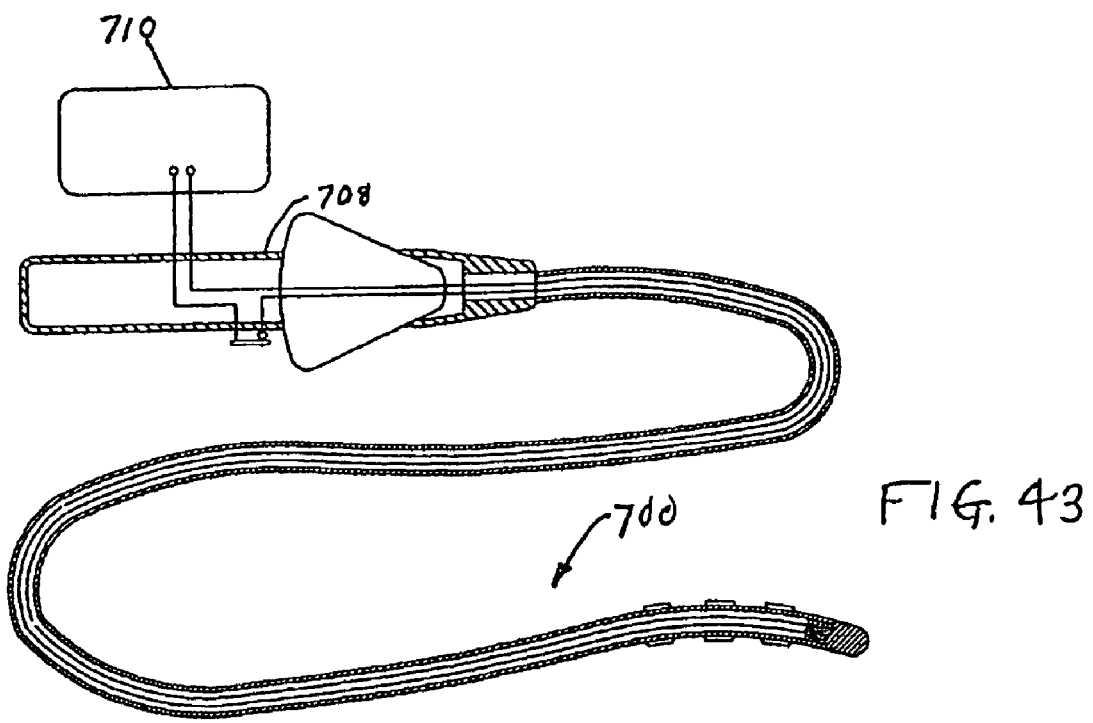
FIG. 43 is a longitudinal section view of an alternate embodiment of the ablation catheter of FIG. 40.

Referring to FIGS. 42 and 43, an alternate version of the embodiment 600 is illustrated wherein the catheter assembly indicated generally at 700 as the construction thereof, identical to the embodiment 600 with the exception that catheter of 700 does not include a heating element in its distal electrode 702; and instead, the temperature of the distal electrode 702 is controlled by a radio-frequency power supply/control module that is external to the catheter of 700.

It will be understood that a fiber optic temperature sensor can be used instead of the solid state junction 716 in an alternate embodiment of catheter 700; and, a fiber optic cable extends within outer casings 706 and 707 to the proximal end of the catheter.

Figures 44, 45:
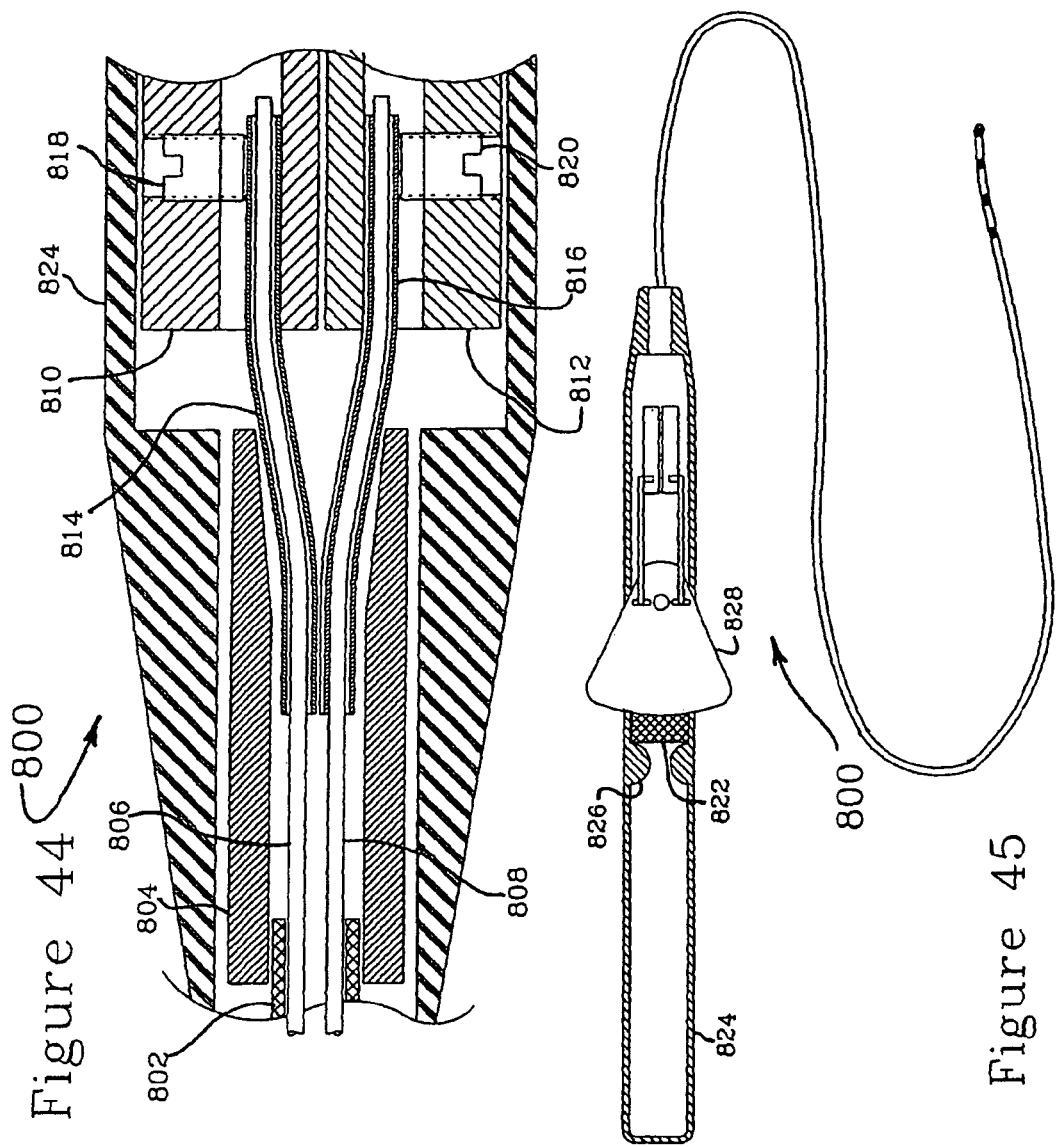
FIG. 44 is an enlarged section view of the proximal end of the catheter of the present invention illustrating the attachment of the tension/compression members to the sliders.
FIG. 45 is a longitudinal section view of an embodiment of the invention employing a self positioning friction brake for the actuator of the handle.

Referring to FIG. 44, another embodiment of catheter handle is indicated generally at 800 and has the proximal end of the guide tube 802 received in a tubular member 804 in a closely fitting arrangement with the tension/compression members 806, 808 extending from the proximal end of he guide tube 802 and through the tube member 804 for connection to a pair of slider blocks 810 and 812 which corresponds in shape and function to the sliders 16 and 17 of FIG. 5. The proximal ends of each of the tension/compression members 806, 808 each have a closely fitting thin wall preferably stainless steel tube 814, 816 received respectively thereover.

The proximal ends of the tension/compression members 806, 808 with their respective tubes 814, 816 are each secured in one of the slider blocks 810, 812 by a set screw 818, 820 respectively which deforms the thin wall of tubing 814, 816 and clamps the tubing and the respective tension/compression members 806, 808 to the slider blocks 810, 812.

Referring to FIG. 45, the embodiment 800 of catheter embodies a friction brake member 822 contained in the handle 824 by interior projection 826 which maintains the member 822 in frictional contact wit the curved edge of the actuator 828 which corresponds in shape and function to actuator 18 of embodiment of FIG. 1. In the present practice of the invention the member 822 is formed of elastomeric material to provide inherent spring compression of the material against the curved edge of the actuator 828; and, the member 822 by virtue of the sliding friction on the curved edge of the actuator 828 serves to retain the actuator 828 in its user selected position after movement from the neutral position shown in FIG. 45.

Figure 46:
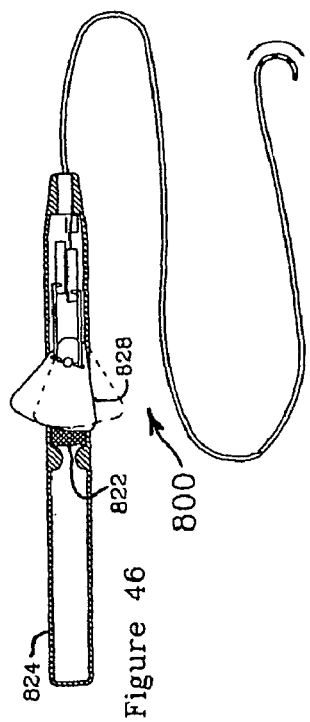
FIG. 46 is a view similar to FIG. 45 showing the actuator in a position for causing curvature at the distal portion of the catheter.

Referring to FIG. 46, the embodiment of catheter 800 illustrated in FIG. 45 is shown with the actuator moved to a user selected position for curving the distal portion of the catheter wherein the member 822 has deformed resiliently to the position of the curved edge of the actuator 828 but is maintaining frictional contact therewith.

Figure 56:
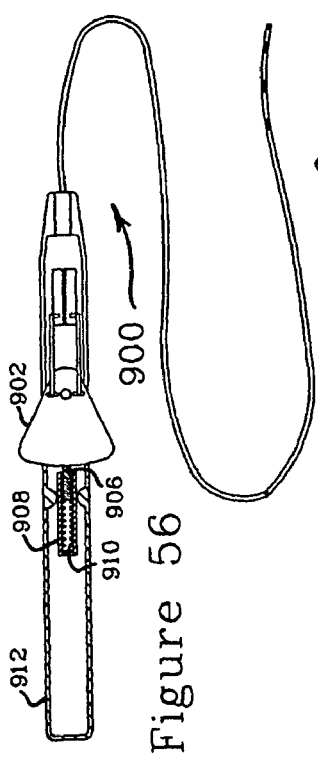
FIG. 56 is a longitudinal section view of the positioning brake for the actuator of the handle of the catheter.
Figure 57:
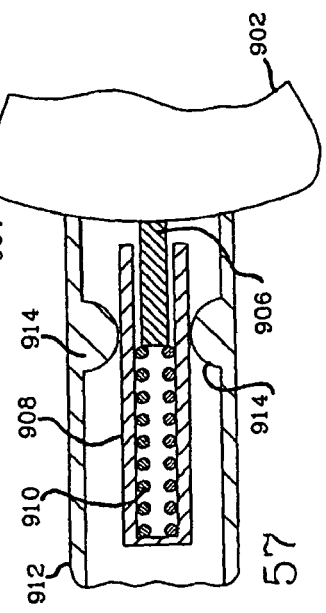
FIG. 57 is an enlarged view of a portion of FIG. 56.

Referring to FIGS. 56 and 57, another version of the frictional retaining member is illustrated in the embodiment indicated generally at 900 wherein the actuator 902 corresponds to the actuator member 828 of the embodiment 800; and, the curved edge portion 904 of the actuator 902 has engaged therewith the end of a spring loaded plunger 906 which is received in a tubular housing 908 which in turn has a compression spring 910 received therein for biasing the plunger 906 in contact with the curved edge 904 of the actuator 902. The tubular member 908 is disposed in the handle 912 between guide projections 914. It will be understood that the plunger 906 serves the same function as the member 822 of the embodiment 800 of FIG. 45.

Figure 47:
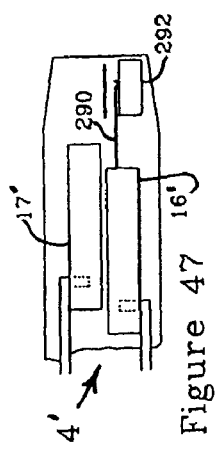
FIG. 47 is a schematic view of the sliders of the handle of he present invention showing a displacement transducer.

Referring to FIG. 47, another embodiment of the catheter handle is indicated generally at 4' wherein the slider 16' and 17' have a wiper tube 290 attached thereto which is operative to vary the electrical resistance in a potentiometer 292 for providing an electrical indicator signal corresponding to the position of the sliders 16', 17' from which the curvature of the distal portion of the catheter may be calibrated for a catheter of known parameters.

Figure 48:
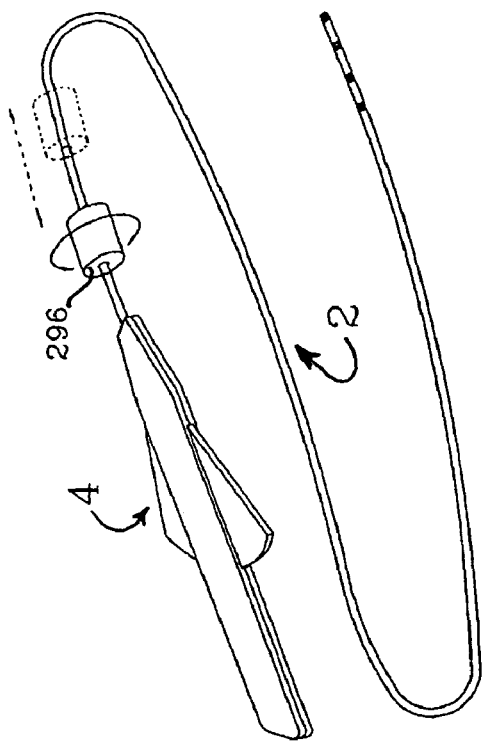
FIG. 48 is a perspective view of the catheter of the present invention employing a collar thereon for enabling user to apply torque to the braided outer casing tube of the catheter.

Referring to FIG. 48, a compressible collar or spool 296 is received over the proximal portion of the braided exterior casing 2 wherein the collar 296 is in frictional sliding engagement with braided exterior casing 2. The collar 296 is preferably formed of soft elastomeric or spongy material. The user may press the collar 296 onto the braided outer casing for readily applying torque thereon for twisting the braided outer casing. As shown by the dashed outlines of FIG. 48, the member 296 may be moved by the user longitudinally along the braided outer casing tube 2 of the catheter for selecting the point of application of the user's applied torque to the catheter's braided outer casing tube.

Figure 49:
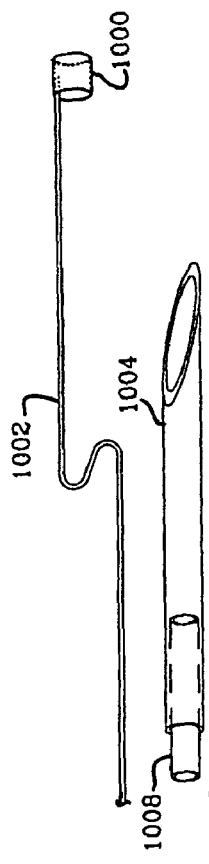
FIG. 49 is a view of the components prior to commencing assembly of the annular electrodes at the distal portion of the catheter.
Figure 50:
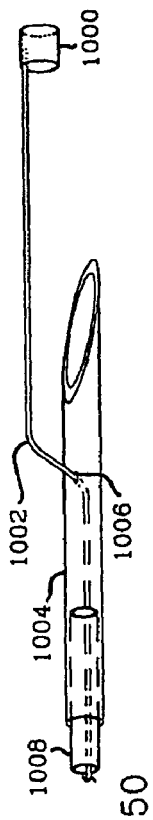
FIG. 50 is a view of the first step of assembly of the annular electrodes.

Referring to FIGS. 48 through 54, the technique for installing one of the annular electrodes over the outer casing at the distal portion of catheter is illustrated and will be described hereinafter with respect to FIGS. 49 through 54. Referring to FIG. 49, an annular electrode 1000 has an electrical conductive lead 1002 attached to the interior periphery thereof and extending outwardly therefrom. The flexible outer casing tubing 1004 has an end thereof received over a rigid tubing such as 1008 which serves as a part of a holding vise for the tubing 1004. The free end of the electrical lead 1002 is then passed through an aperture 1006 on the flexible outer casing tube 1004 and then is passed outwardly through the end of the tubing 1008 as shown in FIG. 50.

Figure 51:
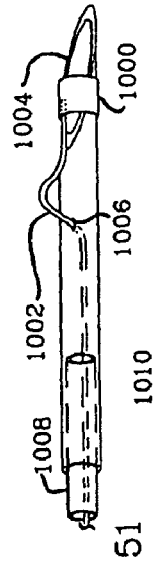
FIG. 51 is a view of the step subsequent to the step of FIG. 50.

Referring to FIG. 51, the electrode 1000 is then assembled over the end of tube 1004 over a tapered portion as shown in FIG. 51.

Figure 52:
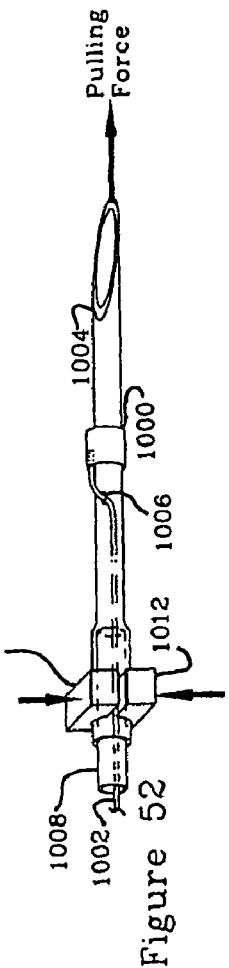
FIG. 52 indicates a further step from the assembly of FIG. 51.
Figure 53:
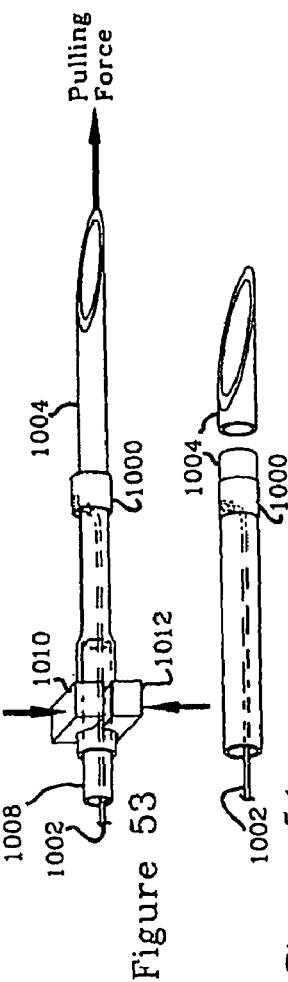
FIG. 53 indicates a subsequent step from FIG. 52.
Figure 54:
FIG. 54 indicates the final step in assembling annular electrodes onto the catheter casing.

The end of the tube 1004 received over tube 1008 is then clamped and secured thereon by suitable clamping fixtures 1010, 1012 as shown in FIG. 52. The tube 1004 is then stretched such that the electrode 1000 may be passed thereover and located over aperture 1006 with the lead 1002 being fed through the end of tubing 1008. It will be understood that the stretching or pulling of tube 1004 as indicated by the arrow in FIG. 52 causes a reduction in diameter of the tube 1004 which permits the electrode 1000 to be slipped thereover and be positioned over the aperture 1006. When the electrode 1000 is located at the desired position over the aperture 1006, the electrical lead 1002 is pulled through the end of the tube 1008 as shown in FIG. 53. When the electrode 1000 has been positioned at the desired position the pulling force on the tubing 1004 is then released, the tubing 1004 expands to engage the interior of the annular electrode 1000 and maintains the electrode 1000 in a desired position on the tube 1004. The clamping load of members 1010, 1012 are then released; the excess material on the end of tube 1004 is then removed as shown in FIG. 54.

Figure 55:
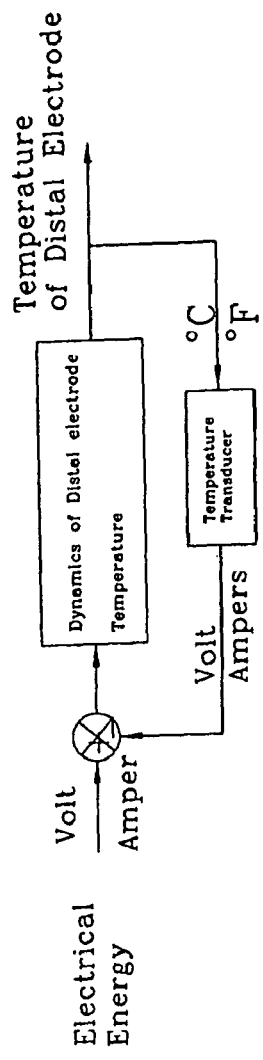
FIG. 55 is a schematic for the temperature control of the ablation catheter of FIG. 40.

Referring to FIG. 55, a schematic view of the temperature control of the distal electrode of the ablation catheter 600 of FIG. 40 is illustrated in a standard feedback control flowchart.

Referring to FIG. 31, all electrodes disposed on the distal portion of the catheter of this invention may be formed of electrically conductive elastomeric material(s)

Although the present invention has been described hereinabove with respect to the illustrated embodiments, it will be understood that the invention is capable of modification and variation and is limited only by the scope of the following claims.

What is claimed is:

1. An electrophysiology/ablation catheter, comprising:
an elongated flexible hollow tubular casing having a proximal end, a distal end, and a plurality of spaced electrodes disposed at the distal end thereof;
a pair of flexible tension/compression members disposed in side-by-side relationship and extending in the hollow of said casing from a point of attachment adjacent said distal end to said proximal end of said tubular casing, wherein each one of said pair of tension/compression members has a portion thereof adjacent said distal end with a flattened transverse cross-section;
an electrical lead connected to each of said electrodes and extending through the hollow of said tubular casing to the proximal end thereof, said lead adapted for external connections thereto;
spacer means disposed between said pair of flexible tension/compression members at said distal end for maintaining lateral spacing between said members, said spacer means being flexible;
a handle including an actuator moveable in opposite directions and operative for effecting upon movement in one direction longitudinal tensioning of a first of said tension/compression members and simultaneous longitudinal compressing of the second of said tension/compression members with respect to said casing which effects lateral displacement of said distal end of said casing in one direction and upon movement in a direction opposite said one direction operative for effecting longitudinal tensioning of the said second of tension/compression members with respect to said casing which effects lateral displacement of said distal end of said casing in a direction opposite said one direction; and
a sleeve received over said flattened portion of said tension/compression members and spaced a preselected distance from said distal end, said tension/compression members secured therein and forming a kinematic junction at said sleeve, wherein the portion of said tubular casing distal said sleeve remains substantially undeformed upon simultaneous tensioning and compressing of said tension/compression members.

2. The catheter as defined in claim 1, wherein said spacer means has an end thereof secured in said sleeve with the other end of said spacer floating in the space between said tension/compression members.

3. An electrophysiology/ablation catheter, comprising:
an elongated flexible hollow tubular casing having a proximal end, a distal end, and a plurality of spaced electrodes disposed at the distal end thereof;
a pair of flexible tension/compression members disposed in side-by-side relationship and extending in the hollow of said casing from a point of attachment adjacent said distal end to said proximal end of said tubular casing;
an electrical lead connected to each of said electrodes and extending through the hollow of said tubular casing to the proximal end thereof, said lead adapted for external connections thereto;
spacer means disposed between said pair of flexible tension/compression members at said distal end for maintaining lateral spacing between said members, said spacer means being flexible;
a handle including an actuator moveable in opposite directions and operative for effecting upon movement in one direction longitudinal tensioning of a first of said tension/compression members and simultaneous longitudinal compressing of the second of said tension/compression members with respect to said casing which effects lateral displacement of said distal end of said casing in one direction and upon movement in a direction opposite said one direction operative for effecting longitudinal tensioning of the said second of tension/compression members with respect to said casing which effects lateral displacement of said distal end of said casing in a direction opposite said one direction;
an elongated flexible tubular guide member disposed in said casing with said tension/compression members received therethrough; and
a rigid collar attached to the distal end of said guide member and extending over a portion of said tension/compression members having said spacer means therebetween.

4. The catheter as defined in claim 3, wherein said rigid collar has a flatted cross-section on one end and a generally circular cross-section on an end opposite said one end.

5. An electrophysiology/ablation catheter, comprising:
an elongated flexible hollow tubular casing having a proximal end, a distal end, and a plurality of spaced electrodes disposed at the distal end thereof;
a pair of flexible tension/compression members disposed in side-by-side relationship and extending in the hollow of said casing from a point of attachment adjacent said distal end to said proximal end of said tubular casing;
an electrical lead connected to each of said electrodes and extending through the hollow of said tubular casing to the proximal end thereof, said lead adapted for external connections thereto;
spacer means disposed between said pair of flexible tension/compression members at said distal end for maintaining lateral spacing between said members, said spacer means being flexible;
a handle including an actuator moveable in opposite directions and operative for effecting upon movement in one direction longitudinal tensioning of a first of said tension/compression members and simultaneous longitudinal compressing of the second of said tension/compression members with respect to said casing which effects lateral displacement of said distal end of said casing in one direction and upon movement in a direction opposite said one direction operative for effecting longitudinal tensioning of the said second of tension/compression members with respect to said casing which effects lateral displacement of said distal end of said casing in a direction opposite said one direction; and an annular reference electrode disposed on said tubular casing at a station therealong remote from said plurality of spaced electrodes, wherein said reference electrode is located such that it remains exterior to the heart cavity upon insertion of the said plurality of spaced electrodes into a heart cavity.

6. An electrophysiology/ablation catheter, comprising:
an elongated flexible hollow casing having a proximal end and a distal end and a plurality of spaced electrodes disposed at the distal end thereof;
first and second flexible tension/compression members disposed and extending in the hollow of said casing from a point of attachment adjacent said distal end to said proximal end of said casing, wherein the first and second flexible tension/compression members each have a substantially rectangular transverse cross-section adjacent the distal end, and wherein the first and second flexible tension/compression members are secured to one another and form a kinematic junction adjacent the substantially rectangular transverse sections;
an electrical lead connected to each of said electrodes and extending through the hollow of said casing to the proximal end thereof, said lead adapted for external connections thereto;
a flexible spacer disposed between the first and second flexible tension/compression members at said distal end for maintaining lateral spacing between said members, wherein the flexible spacer has a first end secured to the first and second flexible tension/compression members at the kinematic junction; and
a handle including an actuator movable in opposite directions and operative for effecting upon movement longitudinal tensioning of the first tension/compression member and simultaneous longitudinal compressing of the second tension/compression member with respect to the casing which effects lateral displacement of the distal end of the casing in a desired direction.

7. The catheter defined in claim 6 wherein the flexible spacer has a second end floating in space between the first and second flexible tension/compression members.

8. An articulated catheter, comprising:
an elongated flexible hollow tubular casing having a proximal end and a distal end;
a pair of flexible tension/compression members disposed substantially side-by-side within the hollow of said casing and extending from a point of attachment adjacent said distal end to said proximal end;
a spacer disposed between said pair of flexible tension/compression members and configured to maintain lateral spacing therebetween, a proximal end of said spacer floating freely between said pair of flexible tension/compression members, wherein said spacer comprises a wave-shaped spring; and
a handle including an actuator movable in opposite directions and coupled to said pair of flexible tension/compression members for effecting, upon actuation, longitudinal tensioning of one of said tension/compression members and longitudinal compression of another of said tension/compression members with respect to said casing, thereby effecting lateral displacement of said distal end of said casing.

9. A method of manufacturing a steerable catheter, comprising:
providing an elongated flexible hollow tubular casing having a proximal end and a distal end;
disposing a plurality of electrodes on the distal end of the casing;
connecting an electrical lead to each of the plurality of electrodes;
installing a pair of flexible deflection members within the casing, the pair of flexible deflection members being attached to the casing at an attachment point adjacent the distal end of the casing and extending substantially side-by-side along the casing towards the proximal end thereof;
installing a flexible spacer between the pair of flexible deflection members such that one end of the spacer floats freely between the pair of deflection members, wherein the flexible spacer sustains a bending moment about only a single axis; and
coupling the deflection members to an actuator.

10. The method according to claim 9, further comprising securing a second, opposite end of the flexible spacer between the pair of flexible deflection members.

11. The method according to claim 10, wherein securing the second, opposite end of the flexible spacer between the pair of flexible deflection members comprises securing the pair of flexible deflection members and the second end of the flexible spacer in a kinematic junction.

12. The method according to claim 11, wherein the securing step comprises receiving the pair of flexible deflection members and the second end of the flexible spacer in a sleeve.

13. The method according to claim 11, wherein the securing step comprises welding the pair of flexible deflection members and the second end of the flexible spacer.

14. An electrophysiology/ablation catheter, comprising:
an elongated flexible hollow tubular casing having a proximal end, a distal end, and a plurality of spaced electrodes disposed at said distal end thereof;
a pair of flexible deflection members disposed in substantially side-by-side relationship and extending in the hollow of said casing from a point of attachment adjacent said distal end to said proximal end of said tubular casing;
an electrical lead connected to each of said electrodes;
a spacer disposed between said pair of flexible deflection members at said distal end, wherein said spacer sustains a bending moment about only a single axis; and
a handle including an actuator movable in opposite directions and coupled to said pair of flexible deflection members for effecting, upon actuation, longitudinal tensioning of one of said deflection members with respect to said casing, thereby effecting lateral displacement of said distal end of said casing.

15. The catheter according to claim 14, wherein said spacer has a substantially flat cross-section.

16. The catheter according to claim 15, wherein said spacer comprises a wave-shaped flat spring.

17. The catheter according to claim 14, wherein said pair of deflection members are kinematically joined at a kinematic junction.

18. The catheter according to claim 17, wherein said kinematic junction is spaced apart from said distal end, said kinematic junction and said distal end defining therebetween a substantially undeflecting portion of said casing.

19. The catheter according to claim 17, wherein a distal end of said spacer is kinematically joined with said pair of deflection members within said kinematic junction.

20. The catheter according to claim 17, wherein said kinematic junction comprises a sleeve received over said pair of deflection members.

21. The catheter according to claim 14, wherein a proximal end of said spacer floats freely between said pair of deflection members.

22. The catheter according to claim 21, wherein said proximal end of said spacer terminates distally of said proximal end of said casing.

23. The catheter according to claim 14, wherein a distal portion of each of said tension/compression members sustains a bending moment about only a single axis.

24. An articulated catheter, comprising:
  an elongated flexible hollow tubular casing having a proximal end and a distal end;
  first and second flexible members disposed substantially side-by-side within said casing and extending from a point of attachment adjacent said distal end towards said proximal end;
  a flexible spacer disposed between said first and second flexible members, at least a first end of said flexible spacer floating freely between said first and second flexible members, the flexible spacer comprising a wave-shaped flat spring; and
  a handle including an actuator movable in opposite directions and coupled to said first and second flexible members for effecting, upon actuation, lateral displacement of said distal end of said casing.

25. The catheter according to claim 24, wherein a second end of said flexible spacer opposite said first end is secured between said first and second flexible members.

26. The catheter according to claim 25, wherein said second end of said flexible spacer is kinematically joined to said first and second flexible members.

27. The catheter according to claim 26, further comprising a sleeve received over said second end of said flexible spacer and said flexible members.

28. The catheter according to claim 24, wherein said flexible spacer is configured to laterally separate said first and second flexible members while permitting relative sliding therebetween.

29. An articulated catheter, comprising:
  an elongated flexible hollow tubular casing having a proximal end and a distal end;
  a pair of flexible tension/compression members disposed substantially side-by-side within the hollow of said casing and extending from a point of attachment adjacent said distal end to said proximal end;
  a spacer disposed between said pair of flexible tension/compression members and configured to maintain lateral spacing therebetween, a proximal end of said spacer floating freely between said pair of flexible tension/compression members, wherein a distal end of said spacer and said flexible tension/compression members are joined in a kinematic junction, and wherein said kinematic junction is spaced a predetermined distance from said distal end of said casing, defining a substantially undeflecting portion of said catheter between said kinematic junction and said distal end of said casing; and
  a handle including an actuator movable in opposite directions and coupled to said pair of flexible tension/compression members for effecting, upon actuation, longitudinal tensioning of one of said tension/compression members and longitudinal compression of another of said tension/compression members with respect to said casing, thereby effecting lateral displacement of said distal end of said casing.

\* \* \* \* \*